US010234449B2

(12) United States Patent
Danino et al.

(10) Patent No.: US 10,234,449 B2
(45) Date of Patent: Mar. 19, 2019

(54) COMPOSITIONS AND METHODS FOR CANCER DIAGNOSIS

(71) Applicants: Massachusetts Institute of Technology, Cambridge, MA (US); The Regents Of The University Of California, Oakland, CA (US)

(72) Inventors: Tal Danino, Cambridge, MA (US); Sangeeta N. Bhatia, Lexington, MA (US); Arthur Prindle, San Diego, CA (US); Jeff Hasty, Encinitas, CA (US)

(73) Assignees: Massachusetts Institute of Technology, Cambridge, MA (US); The Regents of The University of California, Oakland, CA (US)

( * ) Notice: Subject to any disclaimer, the term of this patent is extended or adjusted under 35 U.S.C. 154(b) by 0 days.

(21) Appl. No.: 14/776,689

(22) PCT Filed: Mar. 17, 2014

(86) PCT No.: PCT/US2014/030908
§ 371 (c)(1),
(2) Date: Sep. 14, 2015

(87) PCT Pub. No.: WO2014/146035
PCT Pub. Date: Sep. 18, 2014

(65) Prior Publication Data
US 2016/0033485 A1 Feb. 4, 2016

Related U.S. Application Data

(60) Provisional application No. 61/802,352, filed on Mar. 15, 2013, provisional application No. 61/832,147, filed on Jun. 13, 2013.

(51) Int. Cl.
*C12P 21/06* (2006.01)
*G01N 33/52* (2006.01)
*G01N 33/574* (2006.01)
*A23L 29/00* (2016.01)

(52) U.S. Cl.
CPC ............ *G01N 33/52* (2013.01); *A23L 29/065* (2016.08); *G01N 33/574* (2013.01); *A23V 2002/00* (2013.01); *G01N 2800/7028* (2013.01)

(58) Field of Classification Search
None
See application file for complete search history.

(56) References Cited

U.S. PATENT DOCUMENTS 6,406,724 B1 6/2002 Reddy et al.
2012/0184019 A1 7/2012 Pogliano et al.

OTHER PUBLICATIONS

Mikayama et al. (Nov.1993. Proc.Natl.Acad.Sci. USA, vol. 90 : 10056-10060).*
Rudinger et al. (Jun. 1976. Peptide Hormones. Biol.Council. pp. 5-7).*
Brader et al., Escherichia coli Nissle 1917 facilitates tumor detection by positron emission tomography and optical imaging, Clin Cancer Res 2008 14(8):2295-2302.
Broome et al., Expanding the utility of beta-galactosidase complementation: peice by peice, Mol Pharm 2010 7 (1):60-74.
Cronin et al., High resolution in vivo bioluminescent imaging for the study of bacterial tumour targeting, PLoS One 2012 7(1):e30940.
Cronin et al., Orally administered bifidobacteria as wehicles for delivery of agents to systemic tumors, Mol Ther 2010 18(7):1397-1407.
Danino et al., A synchronized quorum of genetic clocks, Nature 2010 263(7279):326-330.
Danino et al., A synchronized quorum of genetic clocks, Nature 2010 463(7279):326-330.
Danino et al., In vivo gene expression dynamics of tumor-targeted bacteria, ACS Synth Biol 2012 1(10):465-470.
Danino et al., In vivo gene expression dynamics of tumor-targeted bacteria, ACS Synth Biol 2012 1:465-470.
Danino et al., Measuring growth and gene expression dynamics of tumor-targeted S. typhimurium bacteria, J Vis Exp 2013 77:e50540.
Derman et al., Phylogenetic analysis identifies many uncharacterized actin-like proteins (Alps) in bacteria: regulated polymerization, dynamic instability and treadmilling in Alp74, Mol Microbial 2009 73(4):534-52.
Forbes, Engineering the perfect (bacterial) cancer therapy, Nat Rev Cancer 2010 10(11):785-794.
Gerdes et al., mechanism of postsegregational killing by the hok gene product of the parB system of plasmid R1 and its homology with the relF gene product of the E coli relB operon, EMBO J 1986 5(8):2023-2029.
Gerdes et al., Unique type of plasmid maintenance function: postsegregational killing of plasmid-free cells, PNAS 1986 33(10):3116-3120.
Humaran et al., Lactococci and lactobacilli as mucosal delivery vectors for therapeutic proteins and DNA vaccines, Microb Cell Fact 2011 10(Suppl 1):S4.
Kwong et al., Mass-encoded synthetic biomarkers for muyltiplexed urinary monitoring of disease, Nat Biotechnol 2013 31(1):63-70.
Lane et al., Expression of flagella is coincident with uropathogenic Escherichia coli ascension to the upper urinary tract, PNAS 2007 104(42)16669-16674.
Lu and Collins, Engineered bacteriophage targeting gene networks as adjuvants for antibiotic therapy, PNAS 2009 106(12):4629-4634.
Prindle et al., A sensing array of radically coupled genetic 'biopixels', Nature 2011 481(7379):39-44.
Prindle et al., Genetic circuits in Salmonella typhimurium, ACS Synth Biol 2012 1(10):458-464.
Reticker-Flynn et al., A combinatorial extracellular matrix platform identifies cell-extracellular matrix interactions that correlate with metastasis, Nat Commun 2012 3:1122.

(Continued)

Primary Examiner — Jennifer E Graser
(74) Attorney, Agent, or Firm — McCarter & English, LLP; Maria Laccotripe Zacharakis; Joseph Ciardi

(57) ABSTRACT

The present disclosure provides compositions comprising a food product, non-pathogenic microorganism, kits, methods of diagnosing a tumor in a subject, methods of quantifying the number of cancer cells in a cell sample, and methods of detecting a cancer cell, cancer tissue, or cell associated with a hyperproliferative disorder. In some embodiments, the method comprises a step of detecting the presence or absence of a modified substrate or portion thereof in urine of an animal without an instrument and solely by visual inspection of the urine.

26 Claims, 32 Drawing Sheets
Specification includes a Sequence Listing.

(56) References Cited

OTHER PUBLICATIONS

Riedel et al., Contruction of p16Slux, a novel vector for improved bioluminescent labeling of gram-negative bacteria, Appl Environ Microbiol 2007 73(21):7092-7095.
Ruoslahti et al., Targeting of drugs and nanoparticles to tumors, J Cell Biol 2010 188(6):759-768.
Shrivastava et al., Identification and functional characterization of gene components of Type VI Secretion system in bacterial genomes, PLoS One 2008 3(8):e2955.
Toso et al., Phase I study of the intravenous administration of attenuated *Salmonella typhimurium* to patients with metastatic melanoma, J Clin Oncol 2002 20(1):142-152.
Vaupel et al., Blood flow, oxygen and nutrient supply, and metabolic microenvironment of human tumors: a review, Cancer Res 1989 49(23):6449-65.
Nei et al., Bacterial virulence proteins as tools to rewire kinase pathways in yeast and immune cells, Nature 2012 488(7411):384-388.
Winslow et al., Supression of lung adenocarcinoma progression by Nkx2-1, Nature 2011 473(7345):101-104.
Wu et al., Autonomous bacterial localization and gene expression based on nearby cell receptor density, Mol Syst Biol 2013 9:636.
Ye et al., Pharmaceutically controlled designer circuit for the treatment of the metabolic syndrome, PNAS 2013 110(1):141-146.
Zhao et al., Tumor-tegeting bacterial therapy with amino acid auzotrphs of GFP-expressing *Salmonella typhimurium*, PNAS 2005 102(3):755-760.

\* cited by examiner

Hok/sok method:

parM partitioning mechanism:

COMPOSITIONS AND METHODS FOR CANCER DIAGNOSIS

CROSS-REFERENCE TO RELATED APPLICATIONS

This application is an international application designating the United States of America, which claims priority to U.S. Provisional Ser. Nos. 61/802,352, filed Mar. 15, 2013 and 61/832,147, filed Jun. 6, 2013, each of which are herein incorporated by reference in their entirety.

FIELD

The present disclosure is directed, in part, to compositions comprising a non-pathogenic microorganism, kits, methods of diagnosing a tumor in a subject, methods of quantifying the number of cancer cells in a cell sample, and methods of detecting a cancer cell, cancer tissue, or cell associated with a hyperproliferative disorder.

BACKGROUND

Current diagnosis of cancer typically requires instrumentation and costly technology involving expensive reagents and long wait times to obtain results. The expanding field of synthetic biology has yet to be fully leveraged for clinical applications, primarily due to safety concerns and a difficulty in engineering robust circuits in vivo. Accelerating high impact medical applications require utilizing methods that interface directly with medical infrastructure, genetic circuits that function outside of the controlled lab setting, and safe and clinically-accepted microbial hosts. Bacteria have been genetically engineered to participate in luminescence-, PET-, and MRI-based imaging modalities for tumor detection [CITES]. Although these diagnostics each have specific utility, they have required intravenous or intratumoral delivery and expensive equipment, limiting their application to select cases. Strategies to employ quick and non-invasive diagnostic methods for cancer detection are desirable.

SUMMARY

The present disclosure provides compositions comprising a non-pathogenic microorganism comprising: a first nucleic acid sequence encoding an enzyme, or functional fragment thereof; a second nucleic acid sequence encoding an polarization protein or proteins, or functional fragments thereof; and a third nucleic acid sequence encoding a toxin/antidote combination; wherein the enzyme, or functional fragment thereof, catalyzes excitation of a portion of a substrate or the release of a portion of a substrate when the substrate is present in the blood of a subject; and wherein the polarization protein or proteins facilitates the inclusion of both the first and second nucleic acid sequences in the non-pathogenic microorganism and its progeny upon cellular division.

The present disclosure also provides kits comprising the non-pathogenic microorganism compositions described herein.

The present disclosure provides methods of diagnosing a tumor in a subject comprising: i) administering a non-pathogenic microorganism composition described herein to a subject; ii) administering a substrate for the enzyme, or functional fragment thereof, to the subject; and iii) detecting the presence or absence of the released or excited portion of the substrate in the urine of the subject.

The present disclosure also provides methods of quantifying the number of cancer cells in a cell sample comprising: i) contacting the cell sample with a non-pathogenic microorganism composition described herein to form a mixture; ii) exposing the mixture to a substrate for the enzyme, or functional fragment thereof; and iii) measuring the amount of the released or excited portion of the substrate in the mixture.

The present disclosure also provides methods of detecting a cancer cell, cancer tissue, or cell associated with a hyperproliferative disorder in a subject comprising: i) administering non-pathogenic microorganism composition described herein to the subject; ii) administering a substrate for the enzyme, or functional fragment thereof, to the subject; and iii) detecting the presence or absence of the released portion of the substrate.

The present disclosure also provides any one or more of the foregoing non-pathogenic microorganism compositions described herein for detecting the presence of a tumor in a subject.

The present disclosure also provides any one or more of the foregoing non-pathogenic microorganism compositions described herein for use in the manufacture of a product for detecting the presence of a tumor in a subject.

The present disclosure also provides uses of any one or more of the foregoing non-pathogenic microorganism compositions described herein for detecting the presence of a tumor in a subject.

The present invention also provides uses of any one or more of the foregoing non-pathogenic microorganism compositions described herein in the manufacture of a medicament for detecting the presence of a tumor in a subject.

The present invention also provides a composition comprising a non-pathogenic microorganism comprising: one or more plasmids that comprise: a first nucleic acid sequence encoding an enzyme, or functional fragment thereof; a second nucleic acid sequence encoding at least one polarization protein, or functional fragment thereof; and a third nucleic acid sequence encoding a combination of a toxin and an antidote; wherein the enzyme, or functional fragment thereof, processes a substrate into one or more detectable products when the substrate is present in the blood of a subject; and wherein the polarization protein (or, optionally, the combination of the polarization protein, toxin and an antidote) facilitates the inclusion of both the first and second nucleic acid sequences in the non-pathogenic microorganism and its progeny upon cellular division. In some embodiments, the one or more plasmids comprise the first nucleic acid sequence, the second nucleic acid sequence and the third nucleic acid sequence. In some embodiments, the invention relates to any of the compositions disclosed herein, wherein the enzyme, or functional fragment thereof, catalyzes excitation of a portion of a substrate or the release of a portion of a substrate when the substrate is present in the blood of a subject.

In some embodiments, any of the compositions disclosed herein comprise a non-pathogenic microorganism that is a bacterium.

In some embodiments, any of the compositions disclosed herein comprise a non-pathogenic microorganism that is a Gram-negative bacterium.

In some embodiments, any of the compositions disclosed herein comprise a non-pathogenic microorganism that is chosen from: *Escherichia* spp., *Firmicutes* spp., *Bacteroidetes* spp., *Lactobacillus* spp., *Bifidobacteria* spp., or *Acidopholus* spp.

In some embodiments, any of the compositions disclosed herein comprise a non-pathogenic microorganism that is *E. coli* Nissle 1917 (EcN).

In some embodiments, any of the compositions disclosed herein comprise a non-pathogenic microorganism that is harvested from a human or animal sample.

In some embodiments, any of the compositions disclosed herein comprise a non-pathogenic microorganism that comprises a first nucleic acid sequence encoding an enzyme, or functional fragment thereof, wherein the enzyme, or functional fragment thereof, cleaves a portion of a substrate. In some embodiments, the enzyme, or functional fragment thereof, is beta-galactosidase or a functional fragment of beta-galactosidase.

In some embodiments, any of the compositions disclosed herein comprise a non-pathogenic microorganism that comprises a first nucleic acid sequence encoding an enzyme, or functional fragment thereof, wherein the enzyme, or functional fragment thereof excites a substrate thereby emitting a detectable wavelength of light. In some embodiments, the enzyme, or functional fragment thereof processes a substrate into a reaction product capable of emitting a detectable wavelength of light upon exposure to a wavelength of light sufficient for excitation of the reaction product. In some embodiments, the reaction product of the enzyme processing the substrate is capable of being excreted in urine when the substrate and enzyme are administered to animal. In some embodiments, the reaction product of the enzyme processing the substrate is capable of being excreted in urine when the substrate and enzyme are administered to animal per os. In some embodiments, the reaction product of the enzyme processing the substrate is capable of being excreted in urine when either the substrate or the enzyme are administered to animal per os. In some embodiments, the reaction product of the enzyme processing the substrate is capable of being excreted in urine when the substrate is administered intravenously and the enzyme are administered to animal per os as a nucleic acid sequence.

The invention relates to any of the compositions disclosed herein comprising any of the non-pathogenic microorganism disclosed herein wherein the substrate, portion of substrate or the reaction product emits a visible wavelength of light when exposed to white light.

The invention relates to any of the compositions disclosed herein comprising any of the non-pathogenic microorganism disclosed herein, wherein the polarization protein is a cytoplasmic microtubule associated protein. In some embodiments, the nucleic acid that encodes a polarization protein encodes AlpA or a functional fragment thereof. In some embodiments, the nucleic acid that encodes a polarization protein encodes an actin-like protein A (AlpA) family member or a functional fragment thereof. In some embodiments, the nucleic acid that encodes a polarization protein encodes AlpA7 or a functional fragment thereof that has at least 75%, at least 80%, at least 85%, at least 90%, at least 95%, at least 96%, at least 97%, at least 98%, or at least 99% sequence identify to AlpA7. The invention relates to any of the compositions disclosed herein comprising any of the non-pathogenic microorganism disclosed herein, wherein the non-pathogenic microorganism is lyophilized, dried in a powder, or other solid dosage form. In some embodiments, the non-pathogenic microorganism is in a liquid dosage form.

The present invention also relates to kits comprising any of the composition disclosed herein. In some embodiments, the kits further comprise a substrate in place of an enzyme, or functional fragment thereof. In some embodiments, the kits further comprise at least a first container comprising a rehydration solution and, optionally, a syringe and/or needle.

The invention further provides a method of diagnosing or detecting the presence of a tumor in a subject comprising: i) administering any composition disclosed herein, ii) administering a substrate, or functional fragment thereof, for the enzyme, or functional fragment thereof, to the subject wherein the enzyme produced by the microorganism in or on a tumor cell converts the substrate into one or more products that are excreted in urine; iii) detecting in the urine of the subject, the presence or absence of one or more products produced by the processing of the substrate by the enzyme. The invention further provides any of the methods disclosed herein, wherein one or more products produced by the processing of the substrate by the enzyme (each a reaction product) can be visually detected by color in the urine of the subject.

The invention further provides any of the methods disclosed herein, wherein the one or more products produced by the processing of the substrate by the enzyme can be detected in the urine of the subject by combining a sample of the urine with a reactant to produce a detectable result not produced when a sample of urine free of the product is combined with the reactant.

The invention further provides any of the methods disclosed herein, wherein the one or more products produced by the processing of the substrate by the enzyme is the released or excited portion of the substrate.

The invention further provides any of the methods disclosed herein, wherein any of the compositions disclosed herein is or are administered to the subject per os. In some embodiments, the compositions disclosed herein are not administered to the subject per intravenous injection, per subcutaneous injection, or per intramuscular injection. In some embodiments, the compositions disclosed herein are not administered to the subject per injection. The invention further provides any of the methods disclosed herein, wherein any of the compositions disclosed herein is or are administered to the subject per intravenous injection.

The invention further provides any of the methods disclosed herein, wherein the presence or absence of the one or more released or excited portions of the substrate (or one or more reaction products) is determined by identifying a change in the color of the urine.

The invention further provides any of the methods disclosed herein, wherein the substrate is chosen from S-Gal, Ch-Red, and LuGal.

The invention further provides any of the methods disclosed herein, further comprising allowing a period of time to elapse after step i) sufficient for colonization of the microorganism in a tumor cell, tumor tissue, or a cell associated with a hyperproliferative disorder. In some embodiments, the period of time to elapse after step (i) is no more than about 72 hours. In some embodiments, the period of time to elapse after step (i) is no more than about 48 hours. In some embodiments, the period of time to elapse after step (i) is no more than about 36 hours. In some embodiments, the period of time to elapse after step (i) is no more than about 24 hours.

The invention further provides any of the methods disclosed herein, wherein, when the substrate is SGal, the presence or absence of the released or excited portion of the substrate is determined by contacting a urine sample from the subject to iron ions.

The invention further provides any of the methods disclosed herein, wherein when the substrate is D-luciferin-O-β-galactopyranoside (LuGal), the presence or absence of the released or excited portion of the substrate is determined by quantifying the amount of luciferin in the urine sample of the subject.

The invention further provides any of the methods disclosed herein, wherein the tumor is derived from the gastrointestinal tract or urinary system of the subject.

The invention further provides any of the methods disclosed herein, wherein the one or more products produced by the processing of the substrate by the enzyme is detected by comparing the amount of product in the urine of the subject to a background level, wherein a background level is the amount of product that would be found in the urine of a tumor free control subject undergoing the method.

The invention also provides a method of quantifying the number of cancer cells in a cell sample comprising: i) contacting the cell sample with any of the compositions disclosed herein to form a mixture; ii) exposing the mixture to a substrate for the enzyme, or functional fragment thereof; and iii) measuring the amount of the released or excited portion of the substrate in the mixture, or the amount of one or more reaction products.

The invention also provides any of the methods disclosed herein, wherein the quantity of the one or more released or excited portions of the substrate or the one or more reaction products is determined by measuring luminescence, fluorescence or emission of visible wavelengths of light when exposed to white light. The invention also provides any of the methods disclosed herein, wherein the quantity of the one or more released or excited portions of the substrate or the one or more reaction products is determined by colorimetric analysis.

The invention also provides a method of detecting a cancer cell, cancer tissue, or cell associated with a hyperproliferative disorder in a subject comprising: i) administering any the compositions disclosed herein to a subject; ii) administering a substrate for the enzyme, or functional fragment thereof, to the subject; iii) detecting the presence or absence of one or more released or excited portions of the substrate or one or more reaction products, wherein the reaction is the reaction between the enzyme and the substrate.

The invention also provides a method of detecting a cancer cell, cancer tissue, or cell associated with a hyperproliferative disorder in a subject comprising: i) administering any the compositions disclosed herein to a subject; ii) administering a substrate for the enzyme, or functional fragment thereof, to the subject; iii) detecting the presence or absence of one or more released or excited portions of the substrate or one or more reaction products. In some embodiments, the invention provides a method of detecting a cancer cell, cancer tissue, or cell associated with a hyperproliferative disorder in a subject comprising: i) administering any the compositions disclosed herein to a subject; ii) administering a substrate for the enzyme, or functional fragment thereof, to the subject; iii) detecting the presence or absence of one or more released or excited portions of the substrate or one or more reaction products, wherein the composition is administered to the subject per os. In some embodiments, the invention provides a method of detecting a cancer cell, cancer tissue, or cell associated with a hyperproliferative disorder in a subject comprising: i) administering any the compositions disclosed herein to a subject; ii) administering a substrate for the enzyme, or functional fragment thereof, to the subject; iii) detecting the presence or absence of one or more released or excited portions of the substrate or one or more reaction products, wherein the composition is administered to the subject per intravenous injection. In some embodiments, the invention provides a method of detecting a cancer cell, cancer tissue, or cell associated with a hyperproliferative disorder in a subject comprising: i) administering any the compositions disclosed herein to a subject; ii) administering a substrate for the enzyme, or functional fragment thereof, to the subject; iii) detecting the presence or absence of one or more released or excited portions of the substrate or one or more reaction products, wherein the composition is administered to the subject per os and the substrate is administered per os. In some embodiments, the invention provides a method of detecting a cancer cell, cancer tissue, or cell associated with a hyperproliferative disorder in a subject comprising: i) administering any the compositions disclosed herein to a subject; ii) administering a substrate for the enzyme, or functional fragment thereof, to the subject; iii) detecting the presence or absence of one or more released or excited portions of the substrate or one or more reaction products, wherein the composition is administered to the subject per os and the substrate is administered per intravenous injection. In some embodiments, the invention provides a method of detecting a cancer cell, cancer tissue, or cell associated with a hyperproliferative disorder in a subject comprising: i) administering any the compositions disclosed herein to a subject; ii) administering a substrate for the enzyme, or functional fragment thereof, to the subject; iii) detecting the presence or absence of one or more released or excited portions of the substrate or one or more reaction products, wherein the presence or absence of the one or more released or excited portions of the substrate or the one or more reaction products is determined by quantifying the amount of released or excited portion of the substrate present in the subject at one or a plurality of sites in the subject or by quantifying the amount of one or more reaction products present in the subject at one or a plurality of sites in the subject.

In some embodiments, the invention provides a method of detecting a cancer cell, cancer tissue, or cell associated with a hyperproliferative disorder in a subject comprising: i) administering any the compositions disclosed herein to a subject; ii) administering a substrate for the enzyme, or functional fragment thereof, to the subject; iii) detecting the presence or absence of one or more released or excited portions of the substrate or one or more reaction products, wherein the method further comprises allowing a period of time to elapse after step i) sufficient for colonization of the microorganism in a cancer cell, cancer tissue, or a cell associated with hyperproliferative disorder. In some embodiments, the invention provides a method of detecting a cancer cell, cancer tissue, or cell associated with a hyperproliferative disorder in a subject comprising: i) administering any the compositions disclosed herein to a subject; ii) administering a substrate for the enzyme, or functional fragment thereof, to the subject; iii) detecting the presence or absence of one or more released or excited portions of the substrate or one or more reaction products, wherein the method further comprises allowing a period of time to elapse after step i) sufficient for exponential growth of the microorganism in a cancer cell, cancer tissue, or a cell associated with hyperproliferative disorder.

In some embodiments, the invention provides a method of detecting a cancer cell, cancer tissue, or cell associated with a hyperproliferative disorder in a subject comprising: i) administering any the compositions disclosed herein to a subject; ii) administering a substrate for the enzyme, or functional fragment thereof, to the subject; iii) detecting the presence or absence of one or more released or excited portions of the substrate or one or more reaction products, and optionally further comprising allowing a period of time to elapse after step i) sufficient for colonization of the microorganism in a cancer cell, cancer tissue, or a cell associated with hyperproliferative disorder; wherein, when the substrate is SGal, the presence or absence of one or more released or excited portions of the substrate is determined after administration of a composition comprising iron ions.

In some embodiments, the invention provides a method of detecting a cancer cell, cancer tissue, or cell associated with a hyperproliferative disorder in a subject comprising: i) administering any the compositions disclosed herein to a subject; ii) administering a substrate for the enzyme, or functional fragment thereof, to the subject; iii) detecting the presence or absence of one or more released or excited portions of the substrate or one or more reaction products, and optionally further comprising allowing a period of time to elapse after step i) sufficient for colonization of the microorganism in a cancer cell, cancer tissue, or a cell associated with hyperproliferative disorder; wherein the cancer cell, cancer tissue or cell associated with a hyperproliferative disorder is a cancer cell or tissue derived from the gastrointestinal tract or urinary system of a subject. In some embodiments, the invention provides any of the methods disclosed herein, wherein the step of detecting the presence or absence of one or more released or excited portions of the substrate or one or more reaction products is determined without the assistance or reliance or use of an instrument. In some embodiments, the invention provides any of the methods disclosed herein, wherein the step of detecting the presence or absence of one or more released or excited portions of the substrate or one or more reaction products is determined by visual colorimetric analysis of the human eye.

In some embodiments, the invention provides any of the methods disclosed herein, wherein the cancer cell, cancer tissue or cell associated with a hyperproliferative disorder is a metastatic cancer cell or cancer tissue.

In some embodiments, the invention provides any of the methods disclosed herein, wherein the cancer cell, cancer tissue or cell associated with a hyperproliferative disorder is a metastatic cancer cell or cancer tissue present in the liver.

BRIEF DESCRIPTION OF DRAWINGS

FIG. 3 depicts a set of experiments using ECN bacterial strains comprising lacZ fed to mice.

FIG. 5 lower panel also depicts an alternative system for plasmid pairing is used for increased stability of plasmid in transformed bacterial strains. The parA locus of plasmid R1 encodes a prokaryotic centromere-like system that mediates genetic stabilization of plasmids by an unknown mechanism. The locus codes for two proteins, ParM and ParR, and a centromere-like DNA region (parC) to which the ParR protein binds. ParR mediates specific pairing of parC-containing DNA molecules in vitro. ParM forms discrete foci that localize to specific cellular regions in a simple, yet dynamic pattern. In newborn cells, ParM foci were present close to both cell poles. Concomitant with cell growth, new foci formed at mid-cell. A point mutation that abolished the ATPase activity of ParM simultaneously prevented cellular localization and plasmid partitioning. A parA-containing plasmid localized to similar sites, i.e. close to the poles and at mid-cell, thus indicating that the plasmid co-localizes with ParM. Previous data show that plasmid DNA and ParM co-localize and that parA is a true partitioning system that mediates pairing of plasmids at mid-cell and subsequently moves them to the cell poles before cell division.

DETAILED DESCRIPTION OF EMBODIMENTS

Figure 1:
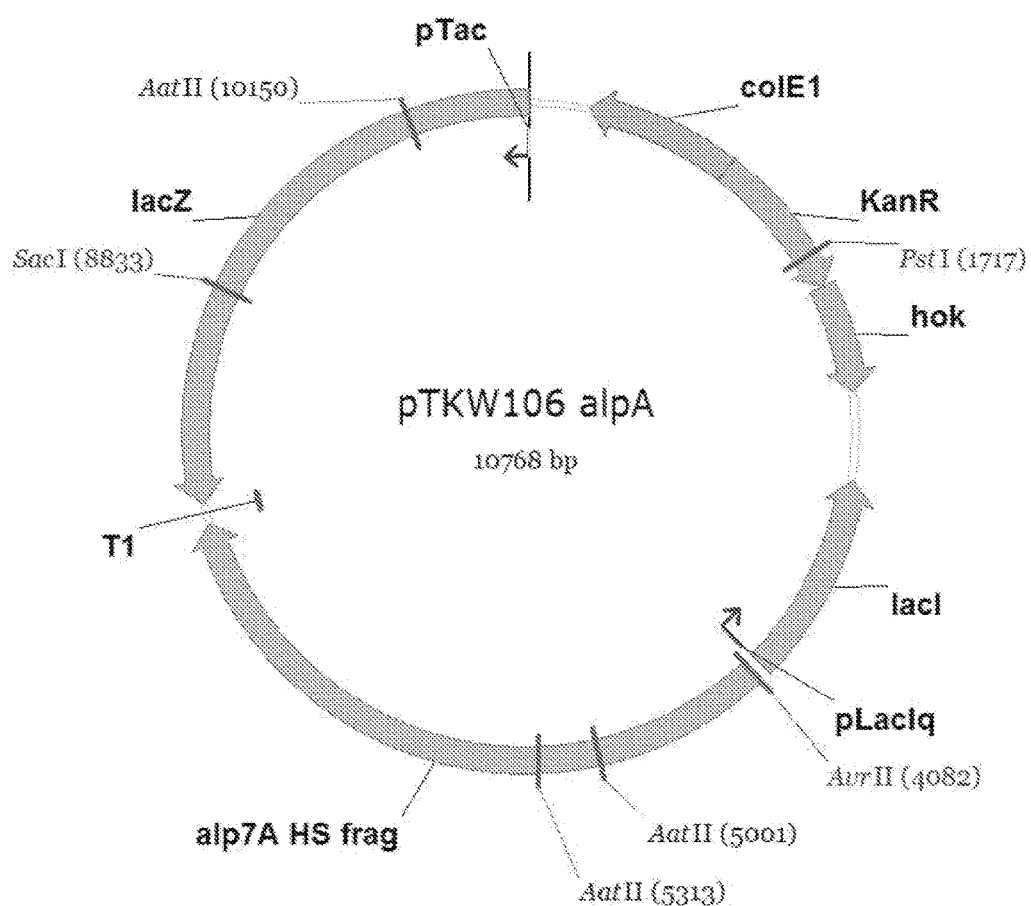
FIG. 1 depicts a non-limiting example of a plasmid containing the nucleic acid sequence encoding the enzyme (LacZ), the nucleic acid sequence encoding the polarization protein (AlpA), and the nucleic acid encoding the toxin-antidote combination (hok/sok).

Some embodiments relate to non-pathogenic microorganisms which comprise heterologous nucleic acid sequences. The non-pathogenic microorganisms colonize tumors. In some embodiments, the non-pathogenic microorganisms are non-pathogenic bacteria.

Some embodiments provide compositions comprising a non-pathogenic microorganism that comprise one or more plasmids, a nucleic acid sequence that encode a polarization protein, or functional fragment thereof and a nucleic acid sequence that encode a combination of a toxin and an antidote. When such microorganism reproduce in vivo, such as when they are colonizing a tumor in an animal, a greater proportion of the resulting progeny remain plasmid-bearing compared to the proportion of resulting progeny from microorganisms which do not comprise a nucleic acid sequence that encodes a polarization protein, or functional fragment thereof and/or a nucleic acid sequence that encode a combination of a toxin and an antidote. The polarization protein, or optionally, the combination of the polarization protein and a toxin and an antidote, reduces plasmid loss that occurs during cell division and facilitates the inclusion of both the plasmids in the non-pathogenic microorganism and its progeny upon cellular division. This feature of improves diagnostics and therapeutics that use microorganisms that target and colonize tumors and release therapeutics or products involved in tumor detection. In some embodiments, the microorganisms further comprise a nucleic acid sequence that encode a protein used in therapeutic methods that cause slowed or inhibit tumor growth or reduce or eliminate tumors. In some embodiments, the microorganisms further comprise a nucleic acid sequence that encode a protein used in diagnostic methods. The protein may be a marker which can be detected directly or indirectly. In some embodiments, the marker is an enzyme which when produced by the microorganism can process a substrate such as a substrate delivered to the animal by injection. In some embodiments, the marker is an substrate which, when produced by the microorganism, can be processed by an enzyme such as an enzyme delivered to the animal by injection. In some embodiments, the marker is a protein which can be detected directly.

Some embodiments provide compositions comprising a non-pathogenic microorganism that comprise one or more plasmids, and a nucleic acid sequence that encode a protein which is used to produce a detectable indicator in the urine of an animal. In some embodiments, the protein is an enzyme which can convert a substrate into detectable products. In some embodiments, substrate is injected in the animal such as by injection into the circulatory system (intrarterial or Intravenously (IV)), subcutaneous (SC) injection or intramuscular (IM) injection or other parenteral injection or by oral administration. In some embodiments, the protein is an enzyme which can convert a substrate into detectable products that are excreted in the urine of the animal. In some embodiments, the protein is an enzyme which can convert a substrate into colored products that are excreted in the urine of the animal and can be detected by visual inspection of the animal's urine. In some embodiments, the protein is an enzyme which can convert a detectable substrate into undetectable products. In some embodiments, enzyme is injected in the animal such as by injection into the circulatory system (intrarterial or IV), SC injection or IM injection or other parenteral injection or by oral administration. In some embodiments, the protein is an substrate which can be converted into a detectable product or a reaction product. In some embodiments, the protein is an substrate which can be converted by an enzyme into a detectable product that is excreted in the urine of the animal. In some embodiments, the protein is a substrate that can be converted by an enzyme into colored products that are excreted in the urine of the animal and can be detected by visual inspection of the animal's urine. In some embodiments, the microorganisms further comprise a nucleic acid sequence that encodes a polarization protein, or functional fragment thereof, and a nucleic acid sequence that encodes a combination of a toxin and an antidote, or functional fragments thereof.

Some embodiments provide methods of detecting tumors in an subject. The non-pathogenic microorganisms which comprise a nucleic acid sequence that encodes a protein which is used to produce a detectable indicator in the urine of an animal as administered to the animal. The non-pathogenic microorganisms may be bacteria. The non-pathogenic microorganisms may be Gram-negative bacteria. The non-pathogenic microorganisms may be administered orally. The non-pathogenic microorganisms may be administered orally. by solid dosage form or liquid dosage form, in either case, optionally as part of a food product. The non-pathogenic microorganisms colonize tumors, or groups of cancer cells. In some embodiments, the tumors or groups of cancer cells are of the gastrointestinal (GI) track. In some embodiments, the tumors or groups of cancer cells are GI-derived tumors. In some embodiments, the tumors or groups of cancer cells are primary non-GI derived tumors. In some embodiments, the tumors or groups of cancer cells are metastatic non-GI derived tumors.

After a sufficient amount of time elapses for colonization to proceed, the urine of the subject is analyzed to determine the present of the detectable indicator in the urine of a subject. In some embodiments, the detectable indicator is a detectable product produced by processing of the substrate by an enzyme encoded by nucleic acid sequences in the microorganism. In such instances, the unprocessed substrate is administered to the subject prior to collecting urine from the subject.

There are several advantages of current technology compared to existing diagnostic agents: (1) in some embodiments, color changes are readily observable to the eye so no instrumentation is required, thus enabling rapid-response and field applications; and (2) Since administration is done with a probiotic that naturally colonizes human gut flora, safety has already been well established. Additionally, probiotics are routinely sold to the public for consumption, opening the possibility for wider applicability in home use. (3) Bacteria, unlike nanoparticle agents, replicate to levels of $10^6$-$10^9$ rapidly over the course of 2 days leading to amplification of signal. Additionally production of an enzyme which can cleave multiple substrates leads to an added level of amplification. (4) To date, no technologies exist that attempt to detect tumors via urine. Substantial existing medical infrastructure for urinalysis could therefore be blended with this technology. (5) The system is essentially free to produce, as bacterial media is the only necessary material. The probiotic compositions are useful for methods for detection of solid tumors in a variety of subtypes. These can be GI tract tumors that bacteria have easy access to or remote metastases that have been shown to be colonizable. In addition, this platform allows for many imaging modalities including PET, MRI, and luminescent detection to be used simultaneously. This work provides a significant decrease in cost with a simultaneous increase in flexibility in terms of diagnostic capabilities.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

As used in this specification and the appended claims, the singular forms "a," "an," and "the" include plural referents unless the content clearly dictates otherwise.

The term "about" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "active state" refers to the conformation or set of conformations of a polypeptide that allows functional domain or domains of the polypeptide to associate or disassociate with another compound, macromolecule, or ligand. In some embodiments, the association or disassociation of the polypeptide with another compound, macromolecule, or ligand may propagate or inhibit a biological signal. In some embodiments, the polypeptide is an enzyme with a catalytic site or functional domain that binds or associates to a substrate upon adopting a conformation or set of conformations in the enzyme's one or more active states.

The terms "amino acid" refer to a molecule containing both an amino group and a carboxyl group bound to a carbon which is designated the α-carbon. Suitable amino acids include, without limitation, both the D- and L-isomers of the naturally-occurring amino acids, as well as non-naturally occurring amino acids prepared by organic synthesis or other metabolic routes. In some embodiments, a single "amino acid" might have multiple sidechain moieties, as available per an extended aliphatic or aromatic backbone scaffold. Unless the context specifically indicates otherwise, the term amino acid, as used herein, is intended to include amino acid analogs including non-natural analogs.

The terms "functional fragment" means any portion of a polypeptide or nucleic acid sequence from which the respective full-length polypeptide or nucleic acid relates that is of a sufficient length and has a sufficient structure to confer a biological affect that is similar or substantially similar to the full-length polypeptide or nucleic acid upon which the fragment is based. In some embodiments, a functional fragment is a portion of a full-length or wild-type nucleic acid sequence that encodes any one of the nucleic acid sequences disclosed herein, and said portion encodes a polypeptide of a certain length and/or structure that is less than full-length but encodes a domain that still biologically functional as compared to the full-length or wild-type protein. In some embodiments, the functional fragment may have a reduced biological activity, about equivalent biological activity, or an enhanced biological activity as compared to the wild-type or full-length polypeptide sequence upon which the fragment is based. In some embodiments, the functional fragment is derived from the sequence of an organism, such as a human. In such embodiments, the functional fragment may retain 99%, 98%, 97%, 96%, 95%, 94%, 93%, 92%, 91%, or 90% sequence identity to the wild-type human sequence upon which the sequence is derived. In some embodiments, the functional fragment may retain 85%, 80%, 75%, 70%, 65%, or 60% sequence homology to the wild-type sequence upon which the sequence is derived. The present invention also comprises functional fragments nucleotide sequences that encode a polypeptide capable of enzymatic activity, substrate activity, polarization activity, toxin activity, or antidote to toxin activity as disclosed herein in an animal. In some embodiments, the functional fragment are DNA fragments selected from at least one of the various nucleotide sequences disclosed herein, including SEQ ID NO: 1 and can be any of the following described DNA fragments, as it applies to the specific encoding nucleic acid sequence provided herein. In some embodiments, DNA fragments can comprise 30 or more, 45 or more, 60 or more, 75 or more, 90 or more, 120 or more, 150 or more, 180 or more, 210 or more, 240 or more, 270 or more, 300 or more, 360 or more, 420 or more, 480 or more, 540 or more, 600 or more, 660 or more, 720 or more, 780 or more, 840 or more, 900 or more, 960 or more, 1020 or more, 1080 or more, 1140 or more, 1200 or more, 1260 or more, 1320 or more, 1380 or more, 1440 or more, 1500 or more, 1560 or more, 1620 or more, 1680 or more, or 1740 or more, 1800 or more, 2000 or more, 2100 or more, 2200 or more, 2300 or more, 2400 or more, 2500 or more, 2600 or more, 2700 or more, 2800 or more, 2900 or more, 3000 or more, 4000 or more, 4500 or more, 5000 or more, 5500 or more, 6000 or more, 6500 or more, 7000 or more, 7500 or more, 8000 or more, 8500 or more, 9000 or more, 9500 or more, 10000 or more, 10100 or more nucleotides. In some embodiments, DNA fragments can comprise coding sequences for partitioning proteins, toxin/antidote combinations, and enzymes disclosed herein. In some embodiments, DNA fragments can comprise fewer than 60, fewer than 75, fewer than 90, fewer than 120, fewer than 150, fewer than 180, fewer than 210, fewer than 240, fewer than 270, fewer than 300, fewer than 360, fewer than 420, fewer than 480, fewer than 540, fewer than 600, fewer than 660, fewer than 720, fewer than 780, fewer than 840, fewer than 900, fewer than 960, fewer than 1020, fewer than 1080, fewer than 1140, fewer than 1200, fewer than 1260, fewer than 1320, fewer than 1380, fewer than 1440, fewer than 1500, fewer than 1560, fewer than 1620, fewer than 1680, or fewer than 1740, fewer than 1800, fewer than 1900, fewer than 2000, fewer than 2100, fewer than 2200, fewer than 2300, fewer than 2400, fewer than 2500, fewer than 2600, fewer than 2700, fewer than 2800, fewer than 2900, fewer than 3000, fewer than 4000, fewer than 5000, fewer than 6000, fewer than 7000, fewer than 8000, fewer than 9000, or fewer than 10000 nucleotides. In some embodiments, the functional fragments are nucleic acid fragments of SEQ ID NO:1 and include one or more nucleic acid derivatives. In some embodiments, the functional fragments are nucleic acid fragments of SEQ ID NO:1 and include more than 5, 10, 15, 20, 25, or 30 nucleic acid derivatives. In some embodiments, the functional fragments are nucleic acid fragments of SEQ ID NO:1 and include one or more conservative substitutions. In some embodiments, the fragments of the present invention comprise or possess at least 70%, at least 75%, at least 80%, at least 85%, at least 90%, at least 91%, at least 92%, at least 93%, at least 94%, at least 95%, at least 96%, at least 97%, at least 98%, or at least 99% homology to SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, or SEQ ID NO:11. In some embodiments, plasmids of the invention comprise at least one or a combination of fragments of at least 70%, at least 75%, at least 80%, at least 85%, at least 90%, at least 91%, at least 92%, at least 93%, at least 94%, at least 95%, at least 96%, at least 97%, at least 98%, or at least 99% homology to SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, or SEQ ID NO:11, each of which possess the function of the full-length SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, or SEQ ID NO:11 respectively.

In some embodiments, the nucleic acid or genetic construct comprises a nucleotide sequence at least 70% sequence identity to SEQ ID NO:1. In some embodiments, the nucleic acid or genetic construct comprises a nucleotide sequence at least 75% sequence identity to SEQ ID NO:1. In some embodiments, the nucleic acid or genetic construct comprises a nucleotide sequence at least 80% sequence identity to SEQ ID NO:1. In some embodiments, the nucleic acid or genetic construct comprises a nucleotide sequence at least 85% sequence identity to SEQ ID NO:1. In some embodiments, the nucleic acid or genetic construct comprises a nucleotide sequence at least 90% sequence identity to SEQ ID NO:1. In some embodiments, the nucleic acid or genetic construct comprises a nucleotide sequence at least 91% sequence identity to SEQ ID NO:1. In some embodiments, the nucleic acid or genetic construct comprises a nucleotide sequence at least 92% sequence identity to SEQ ID NO:1. In some embodiments, the nucleic acid or genetic construct comprises a nucleotide sequence at least 93% sequence identity to SEQ ID NO:1. In some embodiments, the nucleic acid or genetic construct comprises a nucleotide sequence at least 94% sequence identity to SEQ ID NO:1. In some embodiments, the nucleic acid or genetic construct comprises a nucleotide sequence at least 95% sequence identity to SEQ ID NO:1. In some embodiments, the nucleic acid or genetic construct comprises a nucleotide sequence at least 96% sequence identity to SEQ ID NO:1. In some embodiments, the nucleic acid or genetic construct comprises a nucleotide sequence at least 97% sequence identity to SEQ ID NO:1. In some embodiments, the nucleic acid or genetic construct comprises a nucleotide sequence at least 98% sequence identity to SEQ ID NO:1. In some embodiments, the nucleic acid or genetic construct comprises a nucleotide sequence at least 99% sequence identity to SEQ ID NO:1. In some embodiments, the compositions disclosed herein comprise a nucleic acid or genetic construct consisting of SEQ ID NO:1.

In some embodiments, the nucleic acid or genetic construct comprises a nucleotide sequence at least 70% sequence identity to SEQ ID NO:2. In some embodiments, the nucleic acid or genetic construct comprises a nucleotide sequence at least 75% sequence identity to SEQ ID NO:2. In some embodiments, the nucleic acid or genetic construct comprises a nucleotide sequence at least 80% sequence identity to SEQ ID NO:2. In some embodiments, the nucleic acid or genetic construct comprises a nucleotide sequence at least 85% sequence identity to SEQ ID NO:2. In some embodiments, the nucleic acid or genetic construct comprises a nucleotide sequence at least 90% sequence identity to SEQ ID NO:2. In some embodiments, the nucleic acid or genetic construct comprises a nucleotide sequence at least 91% sequence identity to SEQ ID NO:2. In some embodiments, the nucleic acid or genetic construct comprises a nucleotide sequence at least 92% sequence identity to SEQ ID NO:2. In some embodiments, the nucleic acid or genetic construct comprises a nucleotide sequence at least 93% sequence identity to SEQ ID NO:2. In some embodiments, the nucleic acid or genetic construct comprises a nucleotide sequence at least 94% sequence identity to SEQ ID NO:2. In some embodiments, the nucleic acid or genetic construct comprises a nucleotide sequence at least 95% sequence identity to SEQ ID NO:2. In some embodiments, the nucleic acid or genetic construct comprises a nucleotide sequence at least 96% sequence identity to SEQ ID NO:2. In some embodiments, the nucleic acid or genetic construct comprises a nucleotide sequence at least 97% sequence identity to SEQ ID NO:2. In some embodiments, the nucleic acid or genetic construct comprises a nucleotide sequence at least 98% sequence identity to SEQ ID NO:2. In some embodiments, the nucleic acid or genetic construct comprises a nucleotide sequence at least 99% sequence identity to SEQ ID NO:2. In some embodiments, the compositions disclosed herein comprise a nucleic acid or genetic construct consisting of SEQ ID NO:2.

In some embodiments, the nucleic acid or genetic construct comprises a nucleotide sequence at least 70% sequence identity to SEQ ID NO:3. In some embodiments, the nucleic acid or genetic construct comprises a nucleotide sequence at least 75% sequence identity to SEQ ID NO:3. In some embodiments, the nucleic acid or genetic construct comprises a nucleotide sequence at least 80% sequence identity to SEQ ID NO:3. In some embodiments, the nucleic acid or genetic construct comprises a nucleotide sequence at least 85% sequence identity to SEQ ID NO:3. In some embodiments, the nucleic acid or genetic construct comprises a nucleotide sequence at least 90% sequence identity to SEQ ID NO:3. In some embodiments, the nucleic acid or genetic construct comprises a nucleotide sequence at least 91% sequence identity to SEQ ID NO:3. In some embodiments, the nucleic acid or genetic construct comprises a nucleotide sequence at least 92% sequence identity to SEQ ID NO:3. In some embodiments, the nucleic acid or genetic construct comprises a nucleotide sequence at least 93% sequence identity to SEQ ID NO:3. In some embodiments, the nucleic acid or genetic construct comprises a nucleotide sequence at least 94% sequence identity to SEQ ID NO:3. In some embodiments, the nucleic acid or genetic construct comprises a nucleotide sequence at least 95% sequence identity to SEQ ID NO:3. In some embodiments, the nucleic acid or genetic construct comprises a nucleotide sequence at least 96% sequence identity to SEQ ID NO:3. In some embodiments, the nucleic acid or genetic construct comprises a nucleotide sequence at least 97% sequence identity to SEQ ID NO:3. In some embodiments, the nucleic acid or genetic construct comprises a nucleotide sequence at least 98% sequence identity to SEQ ID NO:3. In some embodiments, the nucleic acid or genetic construct comprises a nucleotide sequence at least 99% sequence identity to SEQ ID NO:3. In some embodiments, the compositions disclosed herein comprise a nucleic acid or genetic construct consisting of SEQ ID NO:3.

In some embodiments, the nucleic acid or genetic construct comprises a nucleotide sequence at least 70% sequence identity to SEQ ID NO:4. In some embodiments, the nucleic acid or genetic construct comprises a nucleotide sequence at least 75% sequence identity to SEQ ID NO:4. In some embodiments, the nucleic acid or genetic construct comprises a nucleotide sequence at least 80% sequence identity to SEQ ID NO:4. In some embodiments, the nucleic acid or genetic construct comprises a nucleotide sequence at least 85% sequence identity to SEQ ID NO:4. In some embodiments, the nucleic acid or genetic construct comprises a nucleotide sequence at least 90% sequence identity to SEQ ID NO:4. In some embodiments, the nucleic acid or genetic construct comprises a nucleotide sequence at least 91% sequence identity to SEQ ID NO:4. In some embodiments, the nucleic acid or genetic construct comprises a nucleotide sequence at least 92% sequence identity to SEQ ID NO:4. In some embodiments, the nucleic acid or genetic construct comprises a nucleotide sequence at least 93% sequence identity to SEQ ID NO:4. In some embodiments, the nucleic acid or genetic construct comprises a nucleotide sequence at least 94% sequence identity to SEQ ID NO:4. In some embodiments, the nucleic acid or genetic construct comprises a nucleotide sequence at least 95% sequence identity to SEQ ID NO:4. In some embodiments, the nucleic acid or genetic construct comprises a nucleotide sequence at least 96% sequence identity to SEQ ID NO:4. In some embodiments, the nucleic acid or genetic construct comprises a nucleotide sequence at least 97% sequence identity to SEQ ID NO:4. In some embodiments, the nucleic acid or genetic construct comprises a nucleotide sequence at least 98% sequence identity to SEQ ID NO:4. In some embodiments, the nucleic acid or genetic construct comprises a nucleotide sequence at least 99% sequence identity to SEQ ID NO:4. In some embodiments, the compositions disclosed herein comprise a nucleic acid or genetic construct consisting of SEQ ID NO:4.

In some embodiments, the nucleic acid or genetic construct comprises a nucleotide sequence at least 70% sequence identity to SEQ ID NO:5. In some embodiments, the nucleic acid or genetic construct comprises a nucleotide sequence at least 75% sequence identity to SEQ ID NO:5. In some embodiments, the nucleic acid or genetic construct comprises a nucleotide sequence at least 80% sequence identity to SEQ ID NO:5. In some embodiments, the nucleic acid or genetic construct comprises a nucleotide sequence at least 85% sequence identity to SEQ ID NO:5. In some embodiments, the nucleic acid or genetic construct comprises a nucleotide sequence at least 90% sequence identity to SEQ ID NO:5. In some embodiments, the nucleic acid or genetic construct comprises a nucleotide sequence at least 91% sequence identity to SEQ ID NO:5. In some embodiments, the nucleic acid or genetic construct comprises a nucleotide sequence at least 92% sequence identity to SEQ ID NO:5. In some embodiments, the nucleic acid or genetic construct comprises a nucleotide sequence at least 93% sequence identity to SEQ ID NO:5. In some embodiments, the nucleic acid or genetic construct comprises a nucleotide sequence at least 94% sequence identity to SEQ ID NO:5. In some embodiments, the nucleic acid or genetic construct comprises a nucleotide sequence at least 95% sequence identity to SEQ ID NO:5. In some embodiments, the nucleic acid or genetic construct comprises a nucleotide sequence at least 96% sequence identity to SEQ ID NO:5. In some embodiments, the nucleic acid or genetic construct comprises a nucleotide sequence at least 97% sequence identity to SEQ ID NO:5. In some embodiments, the nucleic acid or genetic construct comprises a nucleotide sequence at least 98% sequence identity to SEQ ID NO:5. In some embodiments, the nucleic acid or genetic construct comprises a nucleotide sequence at least 99% sequence identity to SEQ ID NO:5. In some embodiments, the compositions disclosed herein comprise a nucleic acid or genetic construct consisting of SEQ ID NO:5.

In some embodiments, the nucleic acid or genetic construct comprises a nucleotide sequence at least 70% sequence identity to SEQ ID NO:6. In some embodiments, the nucleic acid or genetic construct comprises a nucleotide sequence at least 75% sequence identity to SEQ ID NO:6. In some embodiments, the nucleic acid or genetic construct comprises a nucleotide sequence at least 80% sequence identity to SEQ ID NO:6. In some embodiments, the nucleic acid or genetic construct comprises a nucleotide sequence at least 85% sequence identity to SEQ ID NO:6. In some embodiments, the nucleic acid or genetic construct comprises a nucleotide sequence at least 90% sequence identity to SEQ ID NO:6. In some embodiments, the nucleic acid or genetic construct comprises a nucleotide sequence at least 91% sequence identity to SEQ ID NO:6. In some embodiments, the nucleic acid or genetic construct comprises a nucleotide sequence at least 92% sequence identity to SEQ ID NO:6. In some embodiments, the nucleic acid or genetic construct comprises a nucleotide sequence at least 93% sequence identity to SEQ ID NO:6. In some embodiments, the nucleic acid or genetic construct comprises a nucleotide sequence at least 94% sequence identity to SEQ ID NO:6. In some embodiments, the nucleic acid or genetic construct comprises a nucleotide sequence at least 95% sequence identity to SEQ ID NO:6. In some embodiments, the nucleic acid or genetic construct comprises a nucleotide sequence at least 96% sequence identity to SEQ ID NO:6. In some embodiments, the nucleic acid or genetic construct comprises a nucleotide sequence at least 97% sequence identity to SEQ ID NO:6. In some embodiments, the nucleic acid or genetic construct comprises a nucleotide sequence at least 98% sequence identity to SEQ ID NO:6. In some embodiments, the nucleic acid or genetic construct comprises a nucleotide sequence at least 99% sequence identity to SEQ ID NO:6. In some embodiments, the compositions disclosed herein comprise a nucleic acid or genetic construct consisting of SEQ ID NO:6.

In some embodiments, the nucleic acid or genetic construct comprises a nucleotide sequence at least 70% sequence identity to SEQ ID NO:7. In some embodiments, the nucleic acid or genetic construct comprises a nucleotide sequence at least 75% sequence identity to SEQ ID NO:7. In some embodiments, the nucleic acid or genetic construct comprises a nucleotide sequence at least 80% sequence identity to SEQ ID NO:7. In some embodiments, the nucleic acid or genetic construct comprises a nucleotide sequence at least 85% sequence identity to SEQ ID NO:7. In some embodiments, the nucleic acid or genetic construct comprises a nucleotide sequence at least 90% sequence identity to SEQ ID NO:7. In some embodiments, the nucleic acid or genetic construct comprises a nucleotide sequence at least 91% sequence identity to SEQ ID NO:7. In some embodiments, the nucleic acid or genetic construct comprises a nucleotide sequence at least 92% sequence identity to SEQ ID NO:7. In some embodiments, the nucleic acid or genetic construct comprises a nucleotide sequence at least 93% sequence identity to SEQ ID NO:7. In some embodiments, the nucleic acid or genetic construct comprises a nucleotide sequence at least 94% sequence identity to SEQ ID NO:7. In some embodiments, the nucleic acid or genetic construct comprises a nucleotide sequence at least 95% sequence identity to SEQ ID NO:7. In some embodiments, the nucleic acid or genetic construct comprises a nucleotide sequence at least 96% sequence identity to SEQ ID NO:7. In some embodiments, the nucleic acid or genetic construct comprises a nucleotide sequence at least 97% sequence identity to SEQ ID NO:7. In some embodiments, the nucleic acid or genetic construct comprises a nucleotide sequence at least 98% sequence identity to SEQ ID NO:7. In some embodiments, the nucleic acid or genetic construct comprises a nucleotide sequence at least 99% sequence identity to SEQ ID NO:7. In some embodiments, the compositions disclosed herein comprise a nucleic acid or genetic construct consisting of SEQ ID NO:7.

In some embodiments, the nucleic acid or genetic construct comprises a nucleotide sequence at least 70% sequence identity to SEQ ID NO:8. In some embodiments, the nucleic acid or genetic construct comprises a nucleotide sequence at least 75% sequence identity to SEQ ID NO:8. In some embodiments, the nucleic acid or genetic construct comprises a nucleotide sequence at least 80% sequence identity to SEQ ID NO:8. In some embodiments, the nucleic acid or genetic construct comprises a nucleotide sequence at least 85% sequence identity to SEQ ID NO:8. In some embodiments, the nucleic acid or genetic construct comprises a nucleotide sequence at least 90% sequence identity to SEQ ID NO:8. In some embodiments, the nucleic acid or genetic construct comprises a nucleotide sequence at least 91% sequence identity to SEQ ID NO:8. In some embodiments, the nucleic acid or genetic construct comprises a nucleotide sequence at least 92% sequence identity to SEQ ID NO:8. In some embodiments, the nucleic acid or genetic construct comprises a nucleotide sequence at least 93% sequence identity to SEQ ID NO:8. In some embodiments, the nucleic acid or genetic construct comprises a nucleotide sequence at least 94% sequence identity to SEQ ID NO:8. In some embodiments, the nucleic acid or genetic construct comprises a nucleotide sequence at least 95% sequence identity to SEQ ID NO:8. In some embodiments, the nucleic acid or genetic construct comprises a nucleotide sequence at least 96% sequence identity to SEQ ID NO:8. In some embodiments, the nucleic acid or genetic construct comprises a nucleotide sequence at least 97% sequence identity to SEQ ID NO:8. In some embodiments, the nucleic acid or genetic construct comprises a nucleotide sequence at least 98% sequence identity to SEQ ID NO:8. In some embodiments, the nucleic acid or genetic construct comprises a nucleotide sequence at least 99% sequence identity to SEQ ID NO:8. In some embodiments, the compositions disclosed herein comprise a nucleic acid or genetic construct consisting of SEQ ID NO:8.

In some embodiments, the nucleic acid or genetic construct comprises a nucleotide sequence at least 70% sequence identity to SEQ ID NO:9. In some embodiments, the nucleic acid or genetic construct comprises a nucleotide sequence at least 75% sequence identity to SEQ ID NO:9. In some embodiments, the nucleic acid or genetic construct comprises a nucleotide sequence at least 80% sequence identity to SEQ ID NO:9. In some embodiments, the nucleic acid or genetic construct comprises a nucleotide sequence at least 85% sequence identity to SEQ ID NO:9. In some embodiments, the nucleic acid or genetic construct comprises a nucleotide sequence at least 90% sequence identity to SEQ ID NO:9. In some embodiments, the nucleic acid or genetic construct comprises a nucleotide sequence at least 91% sequence identity to SEQ ID NO:9. In some embodiments, the nucleic acid or genetic construct comprises a nucleotide sequence at least 92% sequence identity to SEQ ID NO:9. In some embodiments, the nucleic acid or genetic construct comprises a nucleotide sequence at least 93% sequence identity to SEQ ID NO:9. In some embodiments, the nucleic acid or genetic construct comprises a nucleotide sequence at least 94% sequence identity to SEQ ID NO:9. In some embodiments, the nucleic acid or genetic construct comprises a nucleotide sequence at least 95% sequence identity to SEQ ID NO:9. In some embodiments, the nucleic acid or genetic construct comprises a nucleotide sequence at least 96% sequence identity to SEQ ID NO:9. In some embodiments, the nucleic acid or genetic construct comprises a nucleotide sequence at least 97% sequence identity to SEQ ID NO:9. In some embodiments, the nucleic acid or genetic construct comprises a nucleotide sequence at least 98% sequence identity to SEQ ID NO:9. In some embodiments, the nucleic acid or genetic construct comprises a nucleotide sequence at least 99% sequence identity to SEQ ID NO:9. In some embodiments, the compositions disclosed herein comprise a nucleic acid or genetic construct consisting of SEQ ID NO:9.

In some embodiments, the nucleic acid or genetic construct comprises a nucleotide sequence at least 70% sequence identity to SEQ ID NO:10. In some embodiments, the nucleic acid or genetic construct comprises a nucleotide sequence at least 75% sequence identity to SEQ ID NO:10. In some embodiments, the nucleic acid or genetic construct comprises a nucleotide sequence at least 80% sequence identity to SEQ ID NO:10. In some embodiments, the nucleic acid or genetic construct comprises a nucleotide sequence at least 85% sequence identity to SEQ ID NO:10. In some embodiments, the nucleic acid or genetic construct comprises a nucleotide sequence at least 90% sequence identity to SEQ ID NO:10. In some embodiments, the nucleic acid or genetic construct comprises a nucleotide sequence at least 91% sequence identity to SEQ ID NO:10. In some embodiments, the nucleic acid or genetic construct comprises a nucleotide sequence at least 92% sequence identity to SEQ ID NO:10. In some embodiments, the nucleic acid or genetic construct comprises a nucleotide sequence at least 93% sequence identity to SEQ ID NO:10. In some embodiments, the nucleic acid or genetic construct comprises a nucleotide sequence at least 94% sequence identity to SEQ ID NO:10. In some embodiments, the nucleic acid or genetic construct comprises a nucleotide sequence at least 95% sequence identity to SEQ ID NO:01. In some embodiments, the nucleic acid or genetic construct comprises a nucleotide sequence at least 96% sequence identity to SEQ ID NO:10. In some embodiments, the nucleic acid or genetic construct comprises a nucleotide sequence at least 97% sequence identity to SEQ ID NO:10. In some embodiments, the nucleic acid or genetic construct comprises a nucleotide sequence at least 98% sequence identity to SEQ ID NO:10. In some embodiments, the nucleic acid or genetic construct comprises a nucleotide sequence at least 99% sequence identity to SEQ ID NO:10. In some embodiments, the compositions disclosed herein comprise a nucleic acid or genetic construct consisting of SEQ ID NO:10.

In some embodiments, the nucleic acid or genetic construct comprises a nucleotide sequence at least 70% sequence identity to SEQ ID NO:11. In some embodiments, the nucleic acid or genetic construct comprises a nucleotide sequence at least 75% sequence identity to SEQ ID NO:11. In some embodiments, the nucleic acid or genetic construct comprises a nucleotide sequence at least 80% sequence identity to SEQ ID NO:11. In some embodiments, the nucleic acid or genetic construct comprises a nucleotide sequence at least 85% sequence identity to SEQ ID NO:11. In some embodiments, the nucleic acid or genetic construct comprises a nucleotide sequence at least 90% sequence identity to SEQ ID NO:11. In some embodiments, the nucleic acid or genetic construct comprises a nucleotide sequence at least 91% sequence identity to SEQ ID NO:11. In some embodiments, the nucleic acid or genetic construct comprises a nucleotide sequence at least 92% sequence identity to SEQ ID NO:11. In some embodiments, the nucleic acid or genetic construct comprises a nucleotide sequence at least 93% sequence identity to SEQ ID NO:11. In some embodiments, the nucleic acid or genetic construct comprises a nucleotide sequence at least 94% sequence identity to SEQ ID NO:11. In some embodiments, the nucleic acid or genetic construct comprises a nucleotide sequence at least 95% sequence identity to SEQ ID NO:11. In some embodiments, the nucleic acid or genetic construct comprises a nucleotide sequence at least 96% sequence identity to SEQ ID NO:11. In some embodiments, the nucleic acid or genetic construct comprises a nucleotide sequence at least 97% sequence identity to SEQ ID NO:11. In some embodiments, the nucleic acid or genetic construct comprises a nucleotide sequence at least 98% sequence identity to SEQ ID NO:11. In some embodiments, the nucleic acid or genetic construct comprises a nucleotide sequence at least 99% sequence identity to SEQ ID NO:11. In some embodiments, the compositions disclosed herein comprise a nucleic acid or genetic construct consisting of SEQ ID NO:11.

In some embodiments, the nucleic acid or genetic construct comprises a nucleotide sequence at least 70% sequence identity to SEQ ID NO:12. In some embodiments, the nucleic acid or genetic construct comprises a nucleotide sequence at least 75% sequence identity to SEQ ID NO:12. In some embodiments, the nucleic acid or genetic construct comprises a nucleotide sequence at least 80% sequence identity to SEQ ID NO:12. In some embodiments, the nucleic acid or genetic construct comprises a nucleotide sequence at least 85% sequence identity to SEQ ID NO:12. In some embodiments, the nucleic acid or genetic construct comprises a nucleotide sequence at least 90% sequence identity to SEQ ID NO:12. In some embodiments, the nucleic acid or genetic construct comprises a nucleotide sequence at least 91% sequence identity to SEQ ID NO:12. In some embodiments, the nucleic acid or genetic construct comprises a nucleotide sequence at least 92% sequence identity to SEQ ID NO:12. In some embodiments, the nucleic acid or genetic construct comprises a nucleotide sequence at least 93% sequence identity to SEQ ID NO:12. In some embodiments, the nucleic acid or genetic construct comprises a nucleotide sequence at least 94% sequence identity to SEQ ID NO:12. In some embodiments, the nucleic acid or genetic construct comprises a nucleotide sequence at least 95% sequence identity to SEQ ID NO:12. In some embodiments, the nucleic acid or genetic construct comprises a nucleotide sequence at least 96% sequence identity to SEQ ID NO:12. In some embodiments, the nucleic acid or genetic construct comprises a nucleotide sequence at least 97% sequence identity to SEQ ID NO:12. In some embodiments, the nucleic acid or genetic construct comprises a nucleotide sequence at least 98% sequence identity to SEQ ID NO:12. In some embodiments, the nucleic acid or genetic construct comprises a nucleotide sequence at least 99% sequence identity to SEQ ID NO:12. In some embodiments, the compositions disclosed herein comprise a nucleic acid or genetic construct consisting of SEQ ID NO:12.

The terms "hyperproliferative disorder" refer to a disorder characterized by abnormal proliferation, abnormal growth, abnormal senescence, abnormal quiescence, or abnormal removal of cells any or in an organism, and includes include hyperplasias, neoplasias, cancer, fibroproliferative disorders (such as involving connective tissues, as well as other disorders characterized by fibrosis, including for example, rheumatoid arthritis, insulin dependent diabetes mellitus, glomerulonephritis, cirrhosis, and scleroderma), smooth muscle proliferative disorders (such as atherosclerosis and restinosis), chronic inflammation, and epithelial cell proliferative disorders (for example, psoriasis; keratosis; acne; comedogenic lesions; verracous lesions such as verruca plana, plantar warts, verruca acuminata, and other verruciform lesions marked by proliferation of epithelial cells; folliculitis and pseudofolliculitis; keratoacanthoma; callosities; Darier's disease; ichfhyosis; lichen planus; molluscous contagiosum; melasma; Fordyce disease; and keloids or hypertrophic scars). In some embodiments, the hyperproliferative disease is a cancer derived from the gastrointestinal tract or urinary system. In some embodiments, a hyperproliferative disease is a cancer of the adrenal gland, bladder, bone, bone marrow, brain, spine, breast, cervix, gall bladder, ganglia, gastrointestinal tract, stomach, colon, heart, kidney, liver, lung, muscle, ovary, pancreas, parathyroid, penis, prostate, salivary glands, skin, spleen, testis, thymus, thyroid, or uterus. In some embodiments, the term hyperproliferative disease is a cancer chosen from: lung cancer, bone cancer, CMML, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, testicular, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

As used herein, the term "genetic construct" refers to the DNA or RNA molecules that comprise a nucleotide sequence that encodes one or more of the polypeptides. In some embodiments, the genetic construct encodes one or more of the polypeptides described herein. In some embodiments, the nucleotide sequence that encodes a one or more of the polypeptides described herein, or coding sequence, includes initiation and termination signals operably linked to regulatory elements including a bacterial promoter and polyadenylation signal capable of directing expression in the cells of the bacteria in which the nucleic acid molecule is transformed. In some embodiments, the composition or pharmaceutical compositions, kits or nucleic acids comprises at least one genetic construct comprising at least one or combination of: SEQ ID NO:2, SEQ ID NO:3, SEQ ID NO:4, SEQ ID NO:6, SEQ ID NO:7, SEQ ID NO:8, SEQ ID NO:9 or functional fragments of any disclosed percent homology disclosed herein. In some embodiments, the composition or pharmaceutical compositions, kits or nucleic acids comprises at least one genetic construct comprising at least one or combination of: SEQ ID NO:4, SEQ ID NO:6, SEQ ID NO:7, SEQ ID NO:8, SEQ ID NO:10, and SEQ ID NO:11 or functional fragments of any disclosed percent homology disclosed herein. In some embodiments, the composition or pharmaceutical compositions, kits or nucleic acids comprises at least one genetic construct comprising at least one or combination of: SEQ ID NO:4, SEQ ID NO:6, SEQ ID NO:7, SEQ ID NO:8, SEQ ID NO:10, and SEQ ID NO:11 or functional fragments thereof with any disclosed percent homology disclosed herein, optionally comprising at least one or a combination of: SEQ ID NO: 2, SEQ ID NO: 3, SEQ ID NO:9, or functional fragments thereof with any disclosed percent homology disclosed herein. In some embodiments, the composition or pharmaceutical compositions, kits or nucleic acids comprises at least one genetic construct comprising SEQ ID NO:5 or any functional fragment thereof with any disclosed percent homology disclosed herein.

The terms "effective amount" refers to an amount of a compound, material, or composition, as described herein effective to achieve a particular biological result such as, but not limited to, biological results disclosed, described, or exemplified herein. Such results may include, but are not limited to colonization of a tumor by administration of a composition disclosed herein, or production of an amount of a substrate, portion thereof, or a reaction product after exposure of the substrate with an enzyme such that the presence, absence or quantity of substrate, portion thereof, or a reaction product determined by any means suitable in the art. In some embodiments, the biological result is an amount of a substrate, portion thereof, or a reaction product after exposure of the substrate with an enzyme such that the presence, absence or quantity of substrate, portion thereof, or a reaction product determined by visual inspection of urine excreted by a subject administered any one or more compositions disclosed herein. The effective amount of the composition may be dependent on any number of variables, including without limitation, the species, breed, size, height, weight, age, overall health of the subject, the type of formulation, the mode or manner of administration, the type and/or severity of the particular condition being treated.

The terms "electroporation," "electro-permeabilization," or "electro-kinetic enhancement" ("EP") as used interchangeably herein refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

As used herein, the term "expressible form" refers to gene constructs that contain the necessary regulatory elements operable linked to a coding sequence that encodes one or more proteins described herein, such that, when present in a transformed or transfected cell, the coding sequence will be expressed.

As used herein, the term "non-pathogenic microorganism" refers to a microorganism that is not capable of causing a disease or disorder when administered to an animal, including a human. In some embodiments, the microorganism is incapable of causing a disease or disorder when administered to a mammal. In some embodiments, the microorganism is a non-pathogenic microorganism incapable of causing a disease or disorder when administered to a human or domesticated animal (such as a dog, cat, horse, sheep, cow, goat, pig, etc.). In some embodiments, the microorganism is non-pathogenic microorganism incapable of causing a disease or disorder when administered to a human. In some embodiments, the microorganism is non-pathogenic microorganism is chosen from any one of the bacterial species identified in Table 1. In some embodiments, the non-pathogenic microorganism is not one of species listed on Table 1. In some embodiments, the non-pathogenic microorganism is an attenuated bacterial strain. In some embodiments, the non-pathogenic microorganism is an attenuated bacterial strain listed on Table 1. In some embodiments, the non-pathogenic microorganism is an attenuated bacterial strain genetically modified to silence, remove, or mutate a virulence factor.

The term "nucleic acid" refers to a molecule comprising two or more linked nucleotides. "Nucleic acid" and "nucleic acid molecule" are used interchangeably and refer to oligoribonucleotides as well as oligodeoxyribonucleotides. The terms also include polynucleosides (i.e., a polynucleotide minus a phosphate) and any other organic base containing nucleic acid. The organic bases include adenine, uracil, guanine, thymine, cytosine and inosine. The nucleic acids may be single or double stranded. The nucleic acid may be naturally or non-naturally occurring. Nucleic acids can be obtained from natural sources, or can be synthesized using a nucleic acid synthesizer (i.e., synthetic). Isolation of nucleic acids are routinely performed in the art and suitable methods can be found in standard molecular biology textbooks. (See, for example, Maniatis' Handbook of Molecular Biology.) The nucleic acid may be DNA or RNA, such as genomic DNA, mitochondrial DNA, mRNA, cDNA, rRNA, miRNA, PNA or LNA, or a combination thereof, as described herein. Non-naturally occurring nucleic acids such as bacterial artificial chromosomes (BACs) can also be used in accordance with some aspects of this invention.

Some aspects of this invention relate to the use of nucleic acid derivatives. The use of certain nucleic acid derivatives may increase the stability of the nucleic acids of the invention by preventing their digestion, particularly when they are exposed to biological samples that may contain nucleases. As used herein, a nucleic acid derivative is a non-naturally occurring nucleic acid or a unit thereof. Nucleic acid derivatives may contain non-naturally occurring elements such as non-naturally occurring nucleotides and non-naturally occurring backbone linkages. Nucleic acid derivatives according to some aspects of this invention may contain backbone modifications such as but not limited to phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof. The backbone composition of the nucleic acids may be homogeneous or heterogeneous. Nucleic acid derivatives according to some aspects of this invention may contain substitutions or modifications in the sugars and/or bases. For example, some nucleic acid derivatives may include nucleic acids having backbone sugars which are covalently attached to low molecular weight organic groups other than a hydroxyl group at the 3' position and other than a phosphate group at the 5' position (e.g., an 2'-0-alkylated ribose group). Nucleic acid derivatives may include non-ribose sugars such as arabinose. Nucleic acid derivatives may contain substituted purines and pyrimidines such as C-5 propyne modified bases, 5-methylcytosine, 2-aminopurine, 2-amino-6-chloropurine, 2,6-diaminopurine, hypoxanthine, 2-thiouracil and pseudoisocytosine. In some embodiments, a nucleic acid may comprise a peptide nucleic acid (PNA), a locked nucleic acid (LNA), DNA, RNA, or a co-nucleic acids of the above such as DNA-LNA co-nucleic acid.

As used herein the term "isolated nucleic acid molecule" refers to a nucleic acid that is not in its natural environment, for example a nucleic acid that has been (i) extracted and/or purified from a cell or microbe, for example, a bacteria or yeast, by methods known in the art, for example, by alkaline lysis of the host cell and subsequent purification of the nucleic acid, for example, by a silica adsorption procedure; (ii) amplified in vitro, for example, by polymerase chain reaction (PCR); (iii) recombinantly produced by cloning, for example, a nucleic acid cloned into an expression vector; (iv) fragmented and size separated, for example, by enzymatic digest in vitro or by shearing and subsequent gel separation; or (v) synthesized by, for example, chemical synthesis. In some embodiments, the term "isolated nucleic acid molecule" refers to (vi) an nucleic acid that is chemically markedly different from any naturally occurring nucleic acid. In some embodiments, an isolated nucleic acid can readily be manipulated by recombinant DNA techniques well known in the art. Accordingly, a nucleic acid cloned into a vector, or a nucleic acid delivered to a host cell and integrated into the host genome is considered isolated but a nucleic acid in its native state in its natural host, for example, in the genome of the host, is not. An isolated nucleic acid may be substantially purified, but need not be. For example, a nucleic acid that is isolated within a cloning or expression vector is not pure in that it may comprise only a small percentage of the material in the cell in which it resides. Such a nucleic acid is isolated, however, as the term is used herein.

"Sequence homology" or "sequence identity" are used herein interchangeably for nucleotides and amino acids sequences determined using FASTA, BLAST and Gapped BLAST (Altschul et al., Nuc. Acids Res., 1997, 25, 3389, which is incorporated herein by reference in its entirety) and PAUP* 4.ObIO software (D. L. Swofford, Sinauer Associates, Massachusetts). Briefly, the BLAST algorithm, which stands for Basic Local Alignment Search Tool is suitable for determining sequence similarity (Altschul et al., J. MoI. Biol, 1990, 215, 403-410, which is incorporated herein by reference in its entirety). Software for performing BLAST analyses is publicly available through the National Center for Biotechnology Information (http://www.ncbi.nlm.nih.gov). One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001. "Percentage of similarity" or percentage of sequence identity" can be calculated using PAUP* 4.ObIO software (D. L. Swofford, Sinauer Associates, Massachusetts). The average similarity of the consensus sequence is calculated compared to all sequences in the phylogenic tree.

The term "subject" is used throughout the specification to describe an animal to whom treatment with the compositions according to the present invention is provided or administered. For treatment of those conditions which are specific for a specific subject, such as a human being or such as a mammal, the term "patient" may be interchangeably used. In some instances in the description of the present invention, the term "patient" will refer to human patients. In some embodiments, the subject may be a mammal to whom the present invention is provided or administered. In some embodiments, the subject may be a domesticated mammal to whom the present invention is provided or administered such as a horse, dog, cat, pig, cow, goat, sheep, llama, or other non-human animal. In some embodiments, the subject is non-human. In some embodiments, the subject is a mammal suspected of having a hyperproliferative disorder. In some embodiments, the subject is an animal diagnosed with malignant cancer and suspected of having metastatic cancer.

Isolated Nucleic Acid Sequences and Genetic Constructs

The invention provides for compositions comprising isolated nucleic acid molecules and nucleic acid sequences disclosed herein. The invention also provides for kits comprising isolated nucleic acid molecules and nucleic acid sequences disclosed herein. The invention also provides for kits comprising isolated nucleic acid molecules and nucleic acid sequences disclosed herein.

In some embodiments, expressible forms of sequences that encode the one or more polypeptides disclosed herein are found on the same nucleic acid molecule that is transformed into one or more non-pathogenic microorganisms disclosed herein. In some embodiments, expressible forms of sequences that encode the one or more enzymes disclosed herein occur on a separate nucleic acid molecule from the nucleic acid molecules that contain expressible forms of sequences that encode one or more toxin/antidote proteins. In. some embodiments, expressible forms of sequences that encode the one or more enzymes and expressible forms of sequences that encode one or more of the toxin/antidote proteins occur on one nucleic acid molecule that is separate from the nucleic acid molecule that contain expressible forms of sequences that encode one or more of the polarization proteins described herein. Multiple different nucleic acid molecules can be produced and delivered according to the present invention and transformed into the non-pathogenic bacterium described herein. For example, in some embodiments, expressible forms of sequences that encode one or more enzymes described herein occur on separate nucleic acid molecule from the nucleic acid molecules that contain expressible forms of sequences that encode one or more of the polarization proteins which occur on separate nucleic acid molecule from the nucleic acid molecules that contain expressible forms of sequences that encode the toxin/antidote proteins. In such cases, all three molecules are delivered to the individual.

The nucleic acid molecule(s) may be provided as plasmid DNA, the nucleic acid molecules of recombinant vectors or as part of a full or partial artificial bacterial chromosome. In some embodiments, the genetic construct or artificial bacterial chromosome is no more than about 50 kilobases (kb) in nucleic acid base pair length. In some embodiments, the genetic construct or artificial bacterial chromosome is no more than about 45 kb in length. In some embodiments, the genetic construct or artificial bacterial chromosome is no more than about 40 kb in length. In some embodiments, the genetic construct or artificial bacterial chromosome is no more than about 35 kb in length. In some embodiments, the genetic construct or artificial bacterial chromosome is no more than about 30 kb in length. In some embodiments, the genetic construct or artificial bacterial chromosome is no more than about 25 kb in length. In some embodiments, the genetic construct or artificial bacterial chromosome is no more than about 20 kb in length. In some embodiments, the genetic construct or artificial bacterial chromosome is no more than about 15 kb in length. In some embodiments, the genetic construct or artificial bacterial chromosome is no more than about 10 kb in length. In some embodiments, the genetic construct or artificial bacterial chromosome is no more than about 5 kb in length. In some embodiments, the genetic construct or artificial bacterial chromosome is no more than about 2.5 kb in length.

Alternatively, in some embodiments, the nucleic acids that encode the one or more polypeptides and/or one or more proteins described herein may be transformed into any one or more non-pathogenic microorganisms disclosed herein lie on only one plasmid. In some embodiments the non-pathogenic microorganism or organisms do not comprise more than one plasmid that encodes the one or more polypeptides and/or one or more proteins described herein.

Genetic constructs may comprise a nucleotide sequence that encodes one or more of the polypeptides or proteins described herein operably linked to regulatory elements needed for gene expression. According to the invention, combinations of gene constructs that include one that comprises an expressible form of the nucleotide sequence that encodes a the one or more polypeptides disclosed herein and one that includes an expressible form of the nucleotide sequence that encodes are provided. Incorporation into a living cell of the DNA or RNA molecule(s) that include the one or combination of genetic constructs results in the expression of the DNA or RNA and production of the polypeptides or proteins described herein. Incorporation into one or more non-pathogenic microorganisms results in a composition comprising the genetic construct or isolated nucleic acid sequences disclosed herein.

In order to maximize protein production of any of the one or more polypeptides disclosed herein, regulatory sequences may be selected which are well suited for gene expression in the cells the construct is administered into. Moreover, codons may be selected which are most efficiently transcribed in the cell. One having ordinary skill in the art can produce DNA constructs that are functional in the cells.

The present invention provides for a genetic construct that comprises: a first nucleic acid sequence encoding an enzyme, or functional fragment thereof; a second nucleic acid sequence encoding a polarization protein, or functional fragment thereof; and a third nucleic acid sequence encoding a combination of a toxin and an antidote. In some embodiments, the present invention relates to a composition comprising a genetic construct that comprises: a first nucleic acid sequence encoding an enzyme, or functional fragment thereof; a second nucleic acid sequence encoding a polarization protein, or functional fragment thereof; and a third nucleic acid sequence encoding a combination of a toxin and an antidote. In some embodiments, the present invention relates to a composition comprising a genetic construct that comprises: a first nucleic acid sequence encoding an enzyme, or functional fragment thereof; a second nucleic acid sequence encoding a polarization protein, or functional fragment thereof; and a third nucleic acid sequence encoding a combination of a toxin and an antidote wherein the enzyme, or functional fragment thereof, catalyzes excitation of a portion of a substrate or the release of a portion of a substrate when the substrate is present in the blood of a subject. In some embodiments, the present invention relates to a composition comprising a genetic construct that comprises: a first nucleic acid sequence encoding an enzyme, or functional fragment thereof; a second nucleic acid sequence encoding a polarization protein, or functional fragment thereof; and a third nucleic acid sequence encoding a combination of a toxin and an antidote wherein the enzyme, or functional fragment thereof, catalyzes excitation of a portion of a substrate or the release of a portion of a substrate when the substrate is exposed to the enzyme or functional fragment thereof. In some embodiments, the genetic construct is modified so that, upon introduction or transformation into a cellular host (such as one or more of the non-pathogenic microorganisms disclosed herein, expression of the one or more first, second, or third nucleic acids is sufficient to allow maximum protein expression of the nucleic acids without compromising the metabolic pathways of the microorganism that allow growth of the microorganism in a certain microenvironment. A modification of gene expression, also referred to herein as a modulation of gene expression, can be a disruption or inhibition of the natural regulation of expression, an overexpression, an inhibition of expression, or a complete abolishment of expression of a given gene. The insertion of a heterologous promoter upstream of a native gene sequence, for example the consensus TATAAT or TTGACA sequences, or the deletion of regulatory sequences within a promoter, for example regulatory sequences that mediate the inhibition of the consensus TATAAT or TTGACA sequences, are examples of a disruption or inhibition of the natural regulation of expression. Strategies for the modulation of gene expression may include genetic alterations, for example by recombinant technologies, such as gene targeting or viral transductions, or non-genetic alterations, for example environmental alterations known to result in the up- or down-regulation of gene expression, or transient delivery of modulators, for example drugs or small RNA molecules to the target cells. Methods for genetic and non-genetic alterations of microbes are well known to those of skill in the art, and are described, for example, in J. Sambrook and D. Russell, Molecular Cloning: A Laboratory Manual, Cold Spring Harbor Laboratory Press; 3rd edition (Jan. 15, 2001); David C. Amberg, Daniel J. Burke; and Jeffrey N. Strathern, Methods in Yeast Genetics: A Cold Spring Harbor Laboratory Course Manual, Cold Spring Harbor Laboratory Press (April 2005); John N. Abelson, Melvin I. Simon, Christine Guthrie, and Gerald R. Fink, Guide to Yeast Genetics and Molecular Biology, Part A, Volume 194 (Methods in Enzymology Series, 194), Academic Press (Mar. 11, 2004); Christine Guthrie and Gerald R. Fink, Guide to Yeast Genetics and Molecular and Cell Biology, Part B, Volume 350 (Methods in Enzymology, Vol 350), Academic Press; 1st edition (Jul. 2, 2002); Christine Guthrie and Gerald R. Fink, Guide to Yeast Genetics and Molecular and Cell Biology, Part C, Volume 351, Academic Press; 1st edition (Jul. 9, 2002); Gregory N. Stephanopoulos, Aristos A. Aristidou and Jens Nielsen, Metabolic Engineering: Principles and Methodologies, Academic Press; 1 edition (Oct. 16, 1998); and Christina Smolke, The Metabolic Pathway Engineering Handbook: Fundamentals, CRC Press; 1 edition (Jul. 28, 2009), all of which are incorporated by reference herein in their entireties.

The present invention also related to isolated expression vectors or genetic constructs that encode one or more of the polypeptides or functional fragment disclosed herein or compositions comprising any one or combination of the nucleic acid sequences disclosed herein. In some embodiments, the expression vector includes a coding nucleic acid, for example, a nucleic acid encoding an enzyme or functional fragment, a polarization protein or functional fragment thereof and/or a toxin/antidote combination gene product, operably linked to a constitutive promoter. The term "constitutive promoter" refers to a promoter that allows for continual transcription of its associated gene. In some embodiments, the expression vector includes a coding nucleic acid, for example, a nucleic acid encoding a an enzyme or functional fragment, a polarization protein or functional fragment thereof and/or a toxin/antidote combination gene product, operably linked to an inducible promoter. The term "inducible promoter", interchangeably used herein with the term "conditional promoter", refers to a promoter that allows for transcription of its associated gene only in the presence or absence of biotic or abiotic factors. Drug-inducible promoters, for example tetracycline/doxycycline inducible promoters, tamoxifen-inducible promoters, as well as promoters that depend on a recombination event in order to be active, for example the cre-mediated recombination of loxP sites, are examples of inducible promoters that are well known in the art.

In some embodiments, the nucleic acid or genetic construct comprises a nucleotide sequence at least 80% sequence identity to SEQ ID NO:1. In some embodiments, the nucleic acid or genetic construct comprises a nucleotide sequence at least 85% sequence identity to SEQ ID NO:1. In some embodiments, the nucleic acid or genetic construct comprises a nucleotide sequence at least 90% sequence identity to SEQ ID NO:1. In some embodiments, the nucleic acid or genetic construct comprises a nucleotide sequence at least 91% sequence identity to SEQ ID NO:1. In some embodiments, the nucleic acid or genetic construct comprises a nucleotide sequence at least 92% sequence identity to SEQ ID NO:1. In some embodiments, the nucleic acid or genetic construct comprises a nucleotide sequence at least 93% sequence identity to SEQ ID NO:1. In some embodiments, the nucleic acid or genetic construct comprises a nucleotide sequence at least 94% sequence identity to SEQ ID NO:1. In some embodiments, the nucleic acid or genetic construct comprises a nucleotide sequence at least 95% sequence identity to SEQ ID NO:1. In some embodiments, the nucleic acid or genetic construct comprises a nucleotide sequence at least 96% sequence identity to SEQ ID NO:1. In some embodiments, the nucleic acid or genetic construct comprises a nucleotide sequence at least 97% sequence identity to SEQ ID NO:1. In some embodiments, the nucleic acid or genetic construct comprises a nucleotide sequence at least 98% sequence identity to SEQ ID NO:1. In some embodiments, the nucleic acid or genetic construct comprises a nucleotide sequence at least 99% sequence identity to SEQ ID NO:1. In some embodiments, the compositions disclosed herein comprise a nucleic acid or genetic construct consisting of SEQ ID NO:1.

In some embodiments, the non-pathogenic microorganism comprises any one or more of any of the nucleic acid sequence disclosed herein or any functional fragment thereof with any sequence homology disclosed herein (at least 70% through at least 99% sequence homology).

Non-pathogenic Organisms

In some embodiments, the invention relates to a composition comprising a non-pathogenic microorganism that comprises a first nucleic acid sequence encoding an enzyme or functional fragment thereof, a second nucleic acid sequence encoding one or more polarization polypeptides or functional fragments thereof, a third nucleic acid sequence encoding a bacterial toxin or functional fragment thereof, and a fourth nucleic acid sequence encoding an antidote to the bacterial toxin. In order to manufacture or produce such a non-pathogenic microorganism, one of ordinary skill in the art would contact the microorganism with a composition comprising each of the first, second, third, or fourth nucleic acid sequences. Methods to deliver expression vectors or expression constructs into microbes, for example, into non-pathogenic microorganisms, are well known to those of skill in the art. Nucleic acids, including expression vectors, can be delivered to prokaryotic microbes by various methods well known to those of skill in the relevant biological arts. Methods for the delivery of nucleic acids to a microbe in accordance to some aspects of this invention, include, but are not limited to, different chemical, electrochemical and biological approaches, for example, heat shock transformation, electroporation, transfection, for example liposome-mediated transfection, DEAE-Dextran-mediated transfection or calcium phosphate transfection. In some embodiments, a nucleic acid construct, for example an expression construct comprising any combination of the first, second, third, and/or fourth nucleic acid sequences disclosed herein, is introduced into the host microbe using a vehicle, or vector, for transferring genetic material. Vectors for transferring genetic material to microbes are well known to those of skill in the art and include, for example, plasmids, artificial chromosomes, and viral vectors. Methods for the construction of nucleic acid constructs, including expression constructs comprising constitutive or inducible heterologous promoters, knockout and knockdown constructs, as well as methods and vectors for the delivery of a nucleic acid or nucleic acid construct to a microbe are well known to those of skill in the art, and are described, for example, in J. Sambrook and D. Russell, Molecular Cloning: A Laboratory Manual, Cold Spring Harbor Laboratory Press; 3rd edition (Jan. 15, 2001); David C. Amberg, Daniel J. Burke; and Jeffrey N. Strathern, Methods in Yeast Genetics: A Cold Spring Harbor Laboratory Course Manual, Cold Spring Harbor Laboratory Press (April 2005); John N. Abelson, Melvin I. Simon, Christine Guthrie, and Gerald R. Fink, Guide to Yeast Genetics and Molecular Biology, Part A, Volume 194 (Methods in Enzymology Series, 194), Academic Press (Mar. 11, 2004); Christine Guthrie and Gerald R. Fink, Guide to Yeast Genetics and Molecular and Cell Biology, Part B, Volume 350 (Methods in Enzymology, Vol 350), Academic Press; 1st edition (Jul. 2, 2002); Gregory N. Stephanopoulos, Aristos A. Aristidou and Jens Nielsen, Metabolic Engineering: Principles and Methodologies, Academic Press; 1 edition (Oct. 16, 1998); and Christina Smolke, The Metabolic Pathway Engineering Handbook: Fundamentals, CRC Press; 1 edition (Jul. 28, 2009), all of which are incorporated by reference herein in their entireties.

Some aspects of this invention relate to cultures of genetically modified microbes provided herein. In some embodiments, the culture comprises a genetically modified microbe provided herein and a medium, for example, a liquid medium. In some embodiments, the culture comprises a genetically modified microbe provided herein and a carbon source, for example, a carbohydrate source, or an organic acid or salt thereof. In some embodiments, the culture comprises a genetically modified microbe provided herein and a salt and/or buffer establishing conditions of salinity, osmolarity, and pH, that are amenable to survival, growth, and/or catalytic activity of the encoded enzyme. In some embodiments, the culture comprises an additional component, for example, an additive. Non-limiting examples of additives are nutrients, amino acids, albumin, growth factors, enzyme inhibitors (for example protease inhibitors), fatty acids, lipids, hormones (e.g., dexamethasone and gibberellic acid), trace elements, inorganic compounds (e.g., reducing agents, such as manganese), redox-regulators (e.g., antioxidants), stabilizing agents (e.g., dimethylsulfoxide), polyethylene glycol, polyvinylpyrrolidone (PVP), gelatin, antibiotics (e.g., Brefeldin A), salts (e.g., NaCl), chelating agents (e.g., EDTA, EGTA), and enzymes (e.g., cellulase, dispase, hyaluronidase, or DNase). In some embodiments, the culture may comprise a drug inducing or inhibiting transcription from a conditional or inducible promoter, for example doxicycline, tetracycline, tamoxifen, IPTG, hormones, or metal ions. While the specific culture conditions, for example, the concentration of the carbon source, will depend upon the respective engineered microorganism to be cultured, general methods and culture conditions for the generation of microbial cultures are well known to those of skill in the art, and are described, for example, in J. Sambrook and D. Russell, Molecular Cloning: A Laboratory Manual, Cold Spring Harbor Laboratory Press; 3rd edition (Jan. 15, 2001); David C. Amberg, Daniel J. Burke; and Jeffrey N. Strathern, Methods in Yeast Genetics: A Cold Spring Harbor Laboratory Course Manual, Cold Spring Harbor Laboratory Press (April 2005); John N. Abelson, Melvin I. Simon, Christine Guthrie, and Gerald R. Fink, Guide to Yeast Genetics and Molecular Biology, Part A, Volume 194 (Methods in Enzymology Series, 194), Academic Press (Mar. 11, 2004), all of which are incorporated by reference herein.

In some embodiments, the genetically modified non-pathogenic microbe or microorganism exhibits a growth advantage over wild type microbes of the same kind and/or over other microbes, for example, microbes commonly found to contaminate microbial cultures for scaling up production of cultures to large volumes. In some embodiments, the growth and/or proliferation advantage of an engineered microbe provided by aspects of this invention translates into the possibility of using non-sterile culturing and fermentation conditions for production, because the problem of culture overgrowth by contaminating microbes is mitigated or completely abolished. In some embodiments, an engineered microbe provided by aspects of this invention is cultured under non-sterile conditions. For example, in some embodiments, non-sterilized feedstock, non-sterilized culture media, non-sterilized supplements, or a non-sterilized bioreactor (e.g. an open reactor under non-sterile conditions) is used for microorganism division.

A variety of different microbes can be genetically modified according to some aspects of this invention and used for scale-up and/or isolation for eventual animal ingestion, for example, various strains of non-pathogenic E. Coli. In some embodiments, the invention provides for a composition comprising one or a combination of non-pathogenic microorganisms chosen from: probiotic bacteria is chosen from *Escherichia* spp., *Firmicutes* spp., *Bacteroidetes* spp., *Lactobacillus* spp., *Bifidobacteria* spp., or *Acidopholus* spp. In some embodiments, the probiotic is selected from *Lactobacillus, Bifidobacteria*, and *Acidopholus*. In some embodiments, the bacteria is harvested from a human or animal sample and transformed as described herein. with our system. The samples may be from stool samples (probiotics) or human/mouse tumor samples (bacteria that have potential to be very tumor selective). In some embodiments, the non-pathogenic microorganism is *E. coli* Nissle 1917 (EcN). In some embodiments, the non-pathogenic microorganism is a strain of *E. coli* but not the Nissle 1917 (EcN).

The present invention relates to compositions comprising any one or combination of non-pathogenic microorganisms disclosed herein wherein at least one of the microorganisms comprises the first, second, third, and/or fourth nucleic acid sequences disclosed herein either alone or in combination. In some embodiments, the invention relates to compositions comprising any one or combination of non-pathogenic microorganisms disclosed herein wherein at least one of the microorganisms comprises a nucleotide sequence encoding a mutated virulence factor. For instance, in some embodiments, the non-pathogenic microorganism comprises a mutation in its Type I, II, III, IV, V, or VI secretion system which does not allow transport of host toxins and/or host immunogenic proteins out of the cell.

In some embodiments, fermentation processes for large-scale microbe cell division may be carried out in bioreactors, isolated and then resuspended in an amount or dosage form disclosed herein. As used herein, the terms "bioreactor" and "fermentor", which are interchangeably used, refer to an enclosure, or partial enclosure, in which a biological and/or chemical reaction takes place, at least part of which involves a living organism or part of a living organism. A "large-scale bioreactor" or "industrial-scale bioreactor" is a bioreactor that is used to generate large volumes of non-pathogenic microorganisms for large scale isolation. Large scale bioreactors typically have volumes in the range of liters, hundreds of liters, thousands of liters, or more.

Other examples of bacteria that can be modified for use in the invention include food-grade bacterial strains. In some embodiments, the non-pathogenic bacteria is chosen from the bacterials strains identified in Humaran et al., *Microbial Cell Factories* 2011, 10 (Suppl 1):S4; Shrivastava et al., *PlosOne*, August 2008, Volume 3, Issue 8: e2955; and T. Danino et al., *ACS Synth. Biol.* 2012, 1, 465-470, each of which are incorporated by reference in their entireties.

The invention relates to compositions comprising any of the non-pathogenic microorganisms disclosed herein, wherein the compositions are in a solid or liquid dosage form an wherein the microorganisms are in an effective amount to colonize a tumor. The invention relates to compositions comprising any of the non-pathogenic microorganisms disclosed herein, wherein the compositions are in a solid or liquid dosage form an wherein the microorganisms are in an effective amount to colonize a tumor and adequate produce enzyme or substrate in quantities detectable in urine. The invention relates to compositions comprising any of the non-pathogenic microorganisms disclosed herein, wherein the compositions are in a solid or liquid dosage form an wherein the microorganisms are in an effective amount to colonize a tumor and adequate produce enzyme or substrate in quantities detectable in urine by visual inspection. The invention relates to compositions comprising any of the non-pathogenic microorganisms disclosed herein wherein the compositions are in a solid or liquid dosage form. In addition to the compositions disclosed in either solid or liquid form, the formulations and compositions of the present invention may also contain optional ingredients to enhance the characteristics of the solid dosage form, maintain the integrity of microorganisms (in dried, lyophilized, dormant or sporulated forms) during the formulation process, and/or enhance the safety of the formulation. Any additional components may be compatible with the other ingredients in the formulations of the invention, in particular the active ingredients, and may be inert. If inert, the additional component does not adversely affect the osmolarity, osmolality, or isotoncity of the formulations or interfere, to a measurable degree, with the biological function of the non-pathogenic microorganism. Additional optional ingredients that may be used in the formulations of the invention include, for example, coatings, diluents, binders, glidants, lubricants, colors, disintegrants, flavors, sweeteners, polymers or waxes.

Non-limiting examples of diluents include various types of starch, cellulose, crystalline cellulose, microcrystalline cellulose, lactose, fructose, sucrose, mannitol or other sugar alcohols, kaolin, calcium phosphate or sulfate, inorganic salts such as sodium chloride and powdered sugar. Powdered cellulose derivatives are also useful. In some embodiments of the invention, the formulation does not include a diluent.

Lubricants may be included in the formulations of the invention. Such lubricants include, but are not limited to, magnesium stearate, potassium stearate, talc, stearic acid, sodium lauryl sulphate, and paraffin. In some embodiments of the invention, the colonic purgative formulation further comprises magnesium stearate. Lubricants serve to facilitate the manufacturing of a solid dosage form. In some embodiments of the invention, the formulation does not comprise a lubricant.

Additional suitable ingredients also include, but are not limited to, carriers, such as sodium citrate and dicalcium phosphate; fillers or extenders, such as stearates, silicas, gypsum, starches, lactose, sucrose, glucose, mannitol, talc, and silicic acid; binders, such as hydroxypropyl methylcellulose, hydroxymethyl-cellulose, alginates, gelatin, polyvinyl pyrrolidone, sucrose, and acacia; humectants, such as glycerol; disintegrating agents, such as agar, calcium carbonate, potato and tapioca starch, alginic acid, certain silicates, colloidal silicon dioxide, sodium starch glycolate, crospovidone, and sodium carbonate; solution retarding agents, such as paraffin; absorption accelerators, such as quaternary ammonium compounds; wetting agents, such as cetyl alcohol and glycerol monostearate; absorbents, such as kaolin and bentonite clay; stabilizers, such as fumaric acid; coloring agents; buffering agents; dispersing agents; preservatives; organic acids; and organic bases.

In some embodiments of the instant invention, the tablet or capsules may also include inert dispersal agents which will facilitate dissolution of the a solid dosage form of the non-pathogenic microorganisms in the stomach of the patient. Preferably, the dispersal agent is a pharmaceutically acceptable dispersant and is one which also produces no appreciable osmotic effects. Examples of acceptable dispersants include microcrystalline cellulose (which is also useful as a compacting agent) and anhydrous lactose. In some embodiments, the dispersal agent is AC-DI-SOL, a cross-linked starch.

In some embodiments of the present invention, the formulation or composition may also include a buffering agent to minimize any acid imbalance which may accompany ingestion of the compositions disclosed herein. Suitable buffering agents include magnesium hydroxide, aluminum hydroxide, calcium carbonate and magnesium carbonate. In some embodiments, the formulation does not include a buffering agent.

In some embodiments of the invention, an additional component in the formulations of the invention may function to maintain the electrolyte balance in a subject after ingestion of a liquid dosage form of the compositions disclosed herein. For example, formulations of the invention may further comprise calcium, phosphate, potassium, magnesium, other anions, or salts thereof.

The present invention further relates to a food product comprising any one of the disclosed non-pathogenic organisms disclosed herein an optionally any one of combination of the diluents, buffering agents, dispersal agents, carriers, lubricants disclosed herein. In some embodiments, the food product is selected from the group consisting of: beef products, poultry products, pork products, and dairy products; wherein the food product comprises any one or combination of microorganisms disclosed herein. In some embodiments, the food product is a dairy product. If a dairy product one can create the starting material for a fermentation method where the dairy product comprises combination or mixture of an aqueous protein source and a fat source. The dairy product can be or comprise a milk concentrate, a milk substrate, a whey concentrate, a whey substrate, cheese curd, and the like, or combinations of these dairy substances with each other or in combination with a supplemental protein or fat source. The dairy product generally will be in the form of an aqueous protein and fat source combination. It also can be in emulsion form. The same or different dairy product compositions can be used as the starting material used in preparing one or more flavor components.

The dairy products useful as the starting material generally have total solids contents of about 10 to about 50 percent, protein contents of about 10 to about 19 percent, fat contents of about 5 to about 30 percent, and lactose contents of about 0.1 to about 10 percent. Preferably, they have total solids contents of about 25 to about 47 percent, protein contents of about 12 to about 17 percent, fat contents of about 18 to about 25 percent, and lactose contents of about 0.5 to about 5 percent. The moisture levels of the dairy product are generally from about 50 to about 90 percent, preferably from about 53 to about 75 percent.

The protein source can be a dried protein or concentrated material and is a dairy ingredient, such as milk protein concentrate, fractionated milk protein, concentrated milk fat, whey protein concentrate, dried whey, non-fat dry milk, milk protein isolate, whey protein isolate, or mixtures thereof. Other protein sources, such as soy protein, corn protein, wheat protein, and/or rice protein can be used in part or as the sole protein source. The fat source is preferably a milk fat such as anhydrous milk fat, butter, cream, or mixtures thereof. Other non-dairy fat sources, such as vegetable oil, can be used in part or as the sole fat source. The pH of the dairy concentrate or substrate is generally in the range of about 6 to about 7 and preferably in the range of about 6.5 to about 6.7. In general, at least one of the protein and fat sources will include a dairy ingredient in the practice of this invention to provide a highly useful starting material from which various flavors which are normally or otherwise associated with food products can be developed.

A dried protein source, if used, is reconstituted with water. The water is used at a level sufficient to provide total moisture of from about 50 to about 90 percent, preferably from about 53 to about 75 percent in the substrate. The reconstituted protein source is combined with the fat source to provide the substrate. If necessary, the pH of the substrate can be lowered to the proper range (i.e., about 4.6 to about 6 and preferably about 4.8 to about 5.6) by the addition of an edible acid or by use of a lactic acid producing microorganism. Suitable edible acids are non-toxic, inorganic or organic acids, which include hydrochloric acid, acetic acid, maleic acid, tartaric acid, citric acid, phosphoric acid, lactic acid, and mixtures thereof. In preparing the milk concentrate, a homogenization device can be used to reduce the fat droplet particle size and insure homogeneity of the substrate.

In some embodiments, the dairy product used as the starting material is an aqueous milk-derived concentrate or substrate that is a fluid milk concentrate prepared by ultrafiltration (alone or even more preferably combined with diafiltration) or a reconstituted milk substrate prepared from a mixture of an ultrafiltered (UF) or ultrafiltered/diafiltered (UF/DF) milk powder and milk fat. The starting material can be an UF/DF milk having the characteristics such as described in U.S. Pat. No. 6,406,724. These milk concentrates can be used as is or in combination with a supplemental fat source to provide the starting material.

Dairy products useful as starting materials for the methods of the present invention can be prepared from concentrated whole or skim milk with, if desired, added cream or anhydrous milk fat (AMF). The cream or AMF generally is added in an amount of about 0 to about 20 percent, preferably about 2 to about 15 percent, by weight of the mixture. In one embodiment for making the dairy product, skim milk is subjected to conventional ultrafiltration/diafiltration techniques to produce an about 3.times. to about 8.times. (preferably about 5.times.) milk concentrate product. Cream or anhydrous milk fat or a combination thereof is mixed with the milk concentrate. In one exemplary non-limiting embodiment, the resulting mixture is homogenized, and pasteurized under high temperature short time (HTST) conditions, such as at about 76.degree. C. for about 16 seconds in a heat exchanger, and then it is cooled to about 21 to about 27.degree. C. The resulting dairy product can be used as the starting material that is subjected to fermentation to prepare the specific flavoring components of the present invention. In some embodiments, about 1 to about 2 percent salt is added to the dairy product prior to treatment with the various enzymes/cultures/additives to produce the specific flavoring components. The pasteurized dairy product is a relatively viscous liquid, preferably containing about 25 to about 47 percent solids.

Dairy product comprising fluid milk concentrate or whey concentrate, AMF or the like and preferably containing about 1 to about 2 percent salt, can then be divided into one, two or three portions, each of which is treated (i.e., fermented) with specific batches of non-pathogenic microorganisms of the present invention and/or substrates specific for the enzymes of the present invention. In some embodiments, the present invention optionally comprises cultures, adjuncts, and other additives for predetermined time periods sufficient to develop specific flavor characteristics. Specific enzymes, cultures, diluents, substrates (such as IPTG), adjuncts, and other additives are provided herein.

In some embodiments, the food product comprises any one or combination of non-pathogenic microorganisms disclosed herein comprising any one or combination of any nucleic acid sequence disclosed herein.

Enzymes and Substrates

The invention provides a composition comprising a nucleic acid sequence that encodes one or more enzymes capable of catalyzing one or more concurrencies of reactions that excite or release a substrate, or portion of a substrate, or a reaction product detectable in the blood, urine, and/or feces of a subject after administration to the subject. In some embodiments, one or more enzymes capable of catalyzing one or more concurrencies of reactions that excite or release a substrate, or portion of a substrate, or a reaction product emits a visible wavelength of light under white light. In some embodiments, upon administration of the nucleic acid to an animal subject, the nucleic acid sequence encodes an enzyme capable of modifying or cleaving substrate into a colored product, wherein the colored product is excreted by a subject in urine if the cleaving or modifying takes place in a subject. In some embodiments, upon administration of the nucleic acid to an animal subject, the nucleic acid sequence encodes an enzyme capable of modifying or cleaving substrate into a colored product excreted by a subject in urine. In some embodiments, upon administration of the nucleic acid to an animal subject, the nucleic acid sequence encodes an enzyme capable of modifying or cleaving substrate into a product excreted by a subject in urine, wherein the product is excitable or fluorescent under conditions sufficient to excite the product and to emit a wavelength of light visible to the human eye. In some embodiments, the product is excitable or fluorescent under white light, UV light, or infrared light. In some embodiments, the substrate, portion thereof, or product of enzyme catalysis is excitable or fluorescent under white light but is not excitable under UV light, or infrared light. In some embodiments, the substrate, portion thereof, or product of enzyme catalysis is excitable or fluorescent under UV light or infrared light, but not any visible wavelength of light. In some embodiments, the substrate, portion thereof, or product of enzyme catalysis the product is excitable or fluorescent under white light, UV light, or infrared light, but emits a wavelength of light detectable by visual inspection of the human eye.

In some embodiments, the enzyme may be chosen from: glucoronidase or human lactase. If such enzymes are used, in some embodiments, additional administration of effective amounts of their respective known substrates to a subject should be used to detect the presence, absence, or quantities of the substrate or portion thereof or a reaction product in the urine of the subject. In some embodiments, amounts of glucoronidase or human lactase or portions thereof may be measured in the urine of the subject.

lacZ component systems as described in Jiayuan Quan et al., *Nature Biotechnology* 29, 449-452 and *Mol Pharm.* 2010 Feb. 1; 7(1): 60-74. may also be used in some embodiments for detection of components of enzymes rather than detection of substrate or products of enzymatic reactions, such references are herein incorporated by reference in its entirety.

In some embodiments, different strains of mircroorganisms that comprise the plasmid stability machinery disclosed herein comprise genes that encode pigments that can be secreted and act as detectable agent in the urine or body of a subject. One such pigment is violacein.

In some embodiments, the non-pathogenic microorganism comprises

Polarization Sequences

In some embodiments, the second nucleic acid sequence encodes a polarization protein, or functional fragment thereof, wherein the polarization protein facilitates the inclusion of the first, second, and third nucleic acid sequences in the non-pathogenic microorganism and its progeny upon cellular division. In some embodiments, the polarization protein is a cytoplasmic microtubule associated protein or a combination of two cytoplasmic microtubule associated proteins. In some embodiments, the polarization protein is AlpA (see, Example 5 for sequence). Polarization protein systems and their use are well known in the art. A phylogenetic search was conducted and uncovered more than 35 highly divergent families of actin-like proteins (Alps) in bacteria. Their genes are found primarily on phage genomes, on plasmids and on integrating conjugative elements, and are likely to be involved in a variety of functions. Three Alps were characterized and all form filaments in the cell. The filaments of Alp7A, a plasmid partitioning protein and one of the most divergent of the Alps, display dynamic instability and also treadmill. Alp7A requires other elements from the plasmid to assemble into dynamic polymers in the cell. Most if not all of the Alps are indeed actin relatives, and that actin is very well represented in bacteria.

Alp7A is a plasmid partitioning protein, as are the previously characterized ParM and AlfA amino acid sequences. In some embodiments, Alp7A is fued with a fluorescent protein, such as GFP. IN some embodiments, Alp7A-GFP fusion protein retained its function and could be used interchangeably with Alp7A itself. In some embodiments, the methods disclosed herein can correlate Alp7A function with its behaviour in the cell and assess whether the actin properties of Alp7A were required for its function. We found that mutations in two amino acids that would be predicted to interact with nucleotide on the basis of actin biochemistry and structural biology disrupted Alp7A polymerization dynamics. The D212A mutation, which abolished filament formation, was indistinguishable from a null mutation in a plasmid stability assay. The E180A mutation, which permitted filaments to form but eliminated their dynamic properties, was almost as crippling. The analogous mutation in ParM (E148A) eliminates ATP hydrolysis, and leads to stable filament formation. It follows that in order to function as a plasmid partitioning protein, Alp7A must behave as a bacterial actin: it must polymerize into filaments with dynamic properties.

In some embodiments, the plasmids, compositions, pharmaceutical compositions of the claimed invention comprise a nucleic acid sequence comprising SEQ ID NO: 5 or a nucleic acid sequence comprising SEQ ID NO: 6 and SEQ ID NO:7.

In some embodiments, the plasmids, compositions, pharmaceutical compositions of the claimed invention comprise a nucleic acid sequence comprising parMRC. parM has similar extra elements like alp7R, for that system it is parM (actin)+parRC (binding elements)=parMRC. Each of these systems has 1 actin-like element (alp7A in our case) and 1 or more binding element (alp7R in our case) that the actin piece connects to, so that the plasmids can push each other apart. In some emboidments, the polarization protein comprises two amino acid elements, a first amino acid actin-like element, and a second binding element. In some embodiments, the two amino acid elements are alp7A and alp7R or functional fragments thereof. In some embodiments, the two amino acid elements are parM and parRC or functional fragments thereof,

```
wherein parR is:
                                     (SEQ ID NO: 15)
ATGGCTAAAAACCCTATCTCAAATAAGGCAGATAACGACCGGATTCAGAT

CCGGTCTTTCTGGATATCCGAAAGAAAAGCACCCTATGTTTATAGTTTCT

TGAAAAAAACAGAACTTTCTCATAGGGGTGACCAACTGGATTTAATTAGG

TCGGCTATTAGTACCGGGTTGGTATTGAATAATTTATTTCCTGACTTGGC

AAATTTTATAAATGGTTTAAACGAAAGATTAACACTTGCAGATCTTAATA

GGTTTCTGAATGATGGAAATACTATAGATACTGAACCTAAGCCTCCTATT

AATGTATTGCTAGAGAATGTCTTAGATCAAAAGTTTAAGGAGTATTTAAC

ACCTCTACAATTAGATAATTCAAAGCAAGATTCTGTTTCTGTAAAAGAAA

CCTTCCTTGTACAAAAGGAACATGCCTGCTTTGGTGTGAAGATTGAAAAT

GAGGGAAGCGATACCTCTATACCATCTGAAAGCCCACTTTCTTCAGATGC

ATCCAAAATTTCAAAAGAAAAGTCCATTTCCGCTGTGGTGCCAGTGCTAG

AAAAAGTATCGGATGAAAATCAAACCGCCTCCATAAGCATAAAATCTAAA

GCTAAGGCAAACAAGCGACTGGCAACTTTG GCAAGATAG or a functional fragment thereof;
and

Wherein parC is
                                     (SEQ ID NO: 16)
TCATGCGTGGCCCCATTGCTGATGATCGGGGTACGCCAGGTGCAGCACTG

CATCGAAATTGGCCTTGCAGTAGCCGTCCAGCGCCACCCGCGAGCCGAAC

GCCGGCGAAAGGTACTCGACCAGGCCGGGCCGGTCGCGGACCTCGCGCCC
```

-continued
```
CAGGACGTGGATGCGCCGGCCGCGTGTGCCGTCGGGTCCAGGCACGAAGG

CCAGCGCCTCGATGTTGAAGTCGATGGATAGAAGTTGTCGGTAGTGCTTG

GCCGCCCTCATCGCGTCCCCCTTGGTCAAATTGGGTATACCCAT or a functional fragment thereof.
```

Wherein parM is (SEQ ID NO: 18)
```
ATGTTGGTATTCATTGATGACGGTTCAACAAACATCAAACTACAGTGGCA

GGAAAGCGACGGAACAATTAAACAGCACATTAGCCCGAACAGCTTCAAAC

GCGAGTGGGCAGTCTCTTTTGGTGATAAAAAGGTCTTTAACTACACACTG

AACGGCGAACAGTATTCATTTGATCCAATCAGCCCGGATGCTGTAGTCAC

AACCAATATCGCATGGCAATACAGCGACGTTAATGTCGTTGCAGTGCATC

ACGCCTTACTGACCAGTGGTCTGCCGGTAAGCGAAGTGGATATTGTTTGC

ACACTTCCTCTGACAGAGTATTACGACAGAAATAACCAACCCAATACGGA

AAATATTGAGCGTAAGAAAGCAAACTTCCGGAAAAAAATTACATTAAATG

GCGGGGATACATTCACAATAAAAGATGTAAAAGTCATGCCTGAATCTATA

CCGGCAGGTTATGAAGTTCTACAAGAACTGGATGAGTTAGATTCTTTATT

AATTATAGATCTCGGGGGCACCACATTAGATATTTCTCAGGTAATGGGGA

AATTATCGGGGATCAGTAAAATATACGGAGACTCATCTCTTGGTGTCTCT

CTGGTTACATCTGCAGTAAAAGATGCCCTTTCTCTTGCGAGAACAAAAGG

AAGTAGCTATCTTGCTGACGATATAATCATTCACAGAAAAGATAATAACT

ATCTGAAGCAACGAATTAATGATGAGAACAAAATATCAATAGTCACCGAA

GCAATGAATGAAGCACTTCGTAAACTTGAGCAACGTGTATTAAATACGCT

CAATGAATTTTCTGGTTATACTCATGTTATGGTTATAGGCGGTGGCGCAG

AATTAATATGCGATGCAGTAAAAAAACACACACAGATTCGTGATGAACGT

TTTTTCAAAACCAATAACTCTCAATATGATTTAGTTAACGGTATGTATCT

CATAGGTAATTAA or a functional fragment thereof.
```

In some embodiments, the two amino acid elements are alfA and alfB or functional fragments thereof, wherein alfA and alfB are disclosed in NC_021809 incorporated by reference in its entirety.

alfA alfA (SEQ ID NO: 17)
```
TTGACACTAACTACTGTAATTGATATCGGGAATTTTAGTACGAAGTACGC

TTATAAGGACAAAAAACAAATTAAGGTCGGCAGTTTCCCTTCTATTCTCC

ATAGCTACAAGCCTTTAGAAGATTACGAGGGAATGGAAAGAGTAGAGTAC

AACGGCCTTGATTATTATGTTGGAGAAACCGTTAAGAACTTCTATTTCGG

CCGTGAAGAACAAATGTATTTCGGCAATACAAGAAAAGGCCATATGGAAG

GTCAAATTCGATTAGTATATGCTCTCTATACAATCTTTAAAGAGACTGGA

AAGAAAGAATTTAACTTAATTCTAACTTGCCCATATGAAAGTATGGTTAC

AGATAAAAAATATTTCGTTCAACATTTTGAAGGAGAAAGAGAAGTTATCG

TTGAAGGAAAGTCATTCAAATTCACTGTACATAATATCGTGATGGCTGCA

GAGGGATTAGGAGCCCTAAACTTCTCAGATTCATTAAACTGCGTCATTGT
```

-continued
```
AGATGCTGGTTCTAAGACATTAAACGTCCTTTATTTAATCAATGGGTCTA

TAAGTAAAATGGATAGCCATACTATTAATGGTGGGACGATCGACAATTCA

ATAATGGATTTGGCGAAGACTTTTGCTAAGACTTGCAGCAATATCGATTA

TGACTACCCTATTGTTTGTACAGGTGGTAAAGCAGAAGAAATGAAAGAAT

GCTTAGAGAATGTTGGATATTCCACTGTAAGTTCTGCCGAACTGGGTGAG

GATAAACCATCTTACTATGTTAATTCAGTTGGATTGCTTCTAAAATACGG

TAGGAAGTTTGAGGAGATGTTTGCGTGA
```

Toxin/Antidote Sequences

The present invention relates to a non-pathogenic microorganism that comprises a nucleic acid sequence that encodes a bacterial toxin and further comprises a nucleic acid sequence that encodes an antidote to the bacterial toxin. In some embodiments, the nucleic acid sequence encoding the toxin is on a first nucleic acid molecule and the nucleic acid sequence encoding the antidote to the toxin is on a second nucleic acid molecule. In some embodiments, the nucleic acid sequence encoding the toxin and the nucleic acid sequence encoding the antidote to the toxin are in a single plasmid.

Toxin and antidote combinations are known in the art. In some embodiments, the toxin and antidote combination is any of the toxin/antidote combinations disclosed in Gerdes, et al., *Molecular Microbiology* (1990) 4(11), 1807-1818, which is herein incorporated by reference in its entirety. The hok/sok system consists of two genes: hok and sok. The Hok protein is a potent cell-killing agent of 52 amino acids (Gerdes et at. 1986b). The sok product is trans-acting antisense RNA that represses hok gene expression at a post-transcriptional level (Gerdes et al. 1988). Since the initial cloning of the hok/sok locus, a family of hok-homologous killer genes has been identified. The E. Colichromosome carries two hok homologues: re/Fat 34 minutes (Gerdes et al. 1986b), and getA at 0 minutes (Poulsen et al. 1989). Furthermore, Poulsen et al. showed that a wide range of distantly related Gram-negative species also encoded two hok-homologous loci. The F plasmid also carries two hok-homologous loci: srnB near the RepFIG region (Akimoto et al. 1986; Saadi et al. 1987), and flm in the transfer leading region of F (Golub and Low, 1986). Interestingly, all of the hok-homologous killer genes mentioned here are regulated at a post-transcriptional level.

The parB locus of plasmid R1, comprising at most 580 base pairs of DNA, mediates efficient plasmid stabilization via postsegregational killing of plasmid free cells. The locus encodes two small genes, hok and sok. The hok gene product is a potent cell killing protein, the expression of which is regulated by the sok product, an anti-sense RNA complementary to the hok mRNA. The hok mRNA is extraordinarily stable, while the sok-RNA is rapidly degraded. The mechanism of postsegregational killing is explained by the differential decay of the hok and sok-RNA's: In newborn plasmid free cells the prolonged persistence of the hok mRNA leads to synthesis of the Hok protein, thus ensuring a rapid and selective killing of these cells. As predicted from this simple model, any unstably inherited plasmid should become stabilized by carrying the parB locus. This important prediction was confirmed by testing a variety of different replicons. Even plasmids replicating in as distantly related organisms as *Eschericia coli*, *Serratia marsescense*, and *Pseudomonas putida* were efficiently stabilized. The parB locus therefore constitutes a convenient and efficient plasmid stabilization casette, useful in many gram negative species.

Plasmid instability is a primary impediment to industrial utilization of recombinant microorganisms. As the vector becomes more effective in directing protein production, it becomes an increasing drain on cellular metabolism. Betenbaugh et al. (1989) have shown that the growth rate of the plasmid-bearing cell is reduced relative to the plasmid-free cell as cloned-gene expression is increased through either plasmid amplification or promoter induction. Hence, faster-growing, plasmid-free segregants can rapidly outnumber the plasmid-bearing population and greatly reduce the yield of recombinant protein from the culture. In addition, structural instability through homologous recombination events can lead to plasmid derivatives that no longer produce the desired protein.

As a result of the segregational and structural instability, the plasmid initially chosen for our studies, pMJR1750 (Stark, 1987), was extremely unstable in the host strain AMA1004 (Casadaban et al., 1983), even in the presence of antibiotics. This plasmid was chosen to help discern the metabolic impact of recombinant protein expression because it allows transcription of-galactosidase to be tightly regulated by the addition of IPTG to the fermentation medium. In order to increase the stability of this vector, three changes were made to the host/plasmid system: the recA gene was deleted from the host, the antibiotic selection marker was changed from ampicillin (Ap) to kanamycin (Kan), and the parB stability locus of plasmid R1 (Gerdes, 1988) was added to the plasmid.

Structural instability should be reduced considerably by the recA deletion. This deletion should severely limit homologous recombination between the plasmid and chromosome since Csonka and Clark (1979) have shown the Δ (srl-recA)306 mutation used in this work decreases the rate of recombination of the host during conjugation by a factor of 36,000. Additionally, Laban and Cohen (1981) have shown that arecA point mutation lowers the frequency of recombination events within a plasmid by 100-fold.

To provide more effective selection pressure, the selectable marker was changed from β-lactamase ($Ap_r$) to aminoglycoside 3'-phosphotransferase II (APH, $Kan_r$). Unlike APH, β-lactamase is transported to the periplasmic space and leaks in sufficient quantity from plasmid-bearing cells to degrade rapidly the ampicillin in the medium (Kemp and Britz, 1987; Pierce and Gutteridge, 1985). The resultant removal of selection pressure allows the plasmid-free cells to dominate the culture (Nishimura et al., 1987). The use of APH should limit the extracellular clearance of antibiotic from the medium.

The main genetic tool used to boost stability of plasmid pMJR1750 is the parB locus isolated from the multiple resistance factor R1 by K. Gerdes (1988). This locus stabilizes plasmids in a population by encoding a cell-killing gene (hok) whose mRNA is activated only when the cell loses the plasmid. Upon loss of the plasmid, the 52 amino acid Hok protein is expressed, and the cell is rapidly killed due to a collapse of the transmembrane potential and cessation of respiration. Therefore, although this locus does not change the rate of appearance of plasmid-free segregants, it kills them as they are generated. The parB locus is the only system known which utilizes this post-segregational killing mechanism.

The *E. coli* strain AMA1004 (Casadaban et al., 1983) was chosen as a suitable host. Its genotype is: Δ(lacIPOZ)C29 lacY+ hsdR galU galK strAT leuB6 trpC9830 with the result that AMA1004 cannot produce β-galactosidase due to a stable deletion, but it can produce β-galactoside permease. Hence, this strain can be used conveniently with MacConkey agar plates to indicate cells harboring plasmids expressing lacZ. Plasmid-bearing cells form red colonies whereas plasmid-free cells form white colonies.

The tightly-regulated expression vector pMJR1750 (FIG. 1) capable of producing large quantities of β-galactosidase was obtained from Stark (1987). It includes the strong tac promoter upstream of the β-galactosidase gene as well as the lacIQ gene for complete repression. Multiple copies of the tac promoter arising from multiple copies of the plasmid can titrate the repressor if lacIQ is not placed on the expression vector (Stark, 1987). It follows that by adding the noncleavable lactose analog IPTG to the fermentation medium, transcription of lacZ can be induced over a wide range. This vector has the additional advantage that its DNA sequence has been completely determined.

In order to limit homologous recombination, P1 kc generalized transduction was used to introduce a recA deletion into the host strain AMA1004. The donor strain for the transduction was constructed by Ihara et al. (1985) and consists of the host JC10289 with the genotype Δ (srl-recA) 306::TnlO, and the helper plasmid pKY102 which is recA+ and ampicillin-resistant. The method of Silhavy et al. (1984) was used to perform the transduction of AMA1004 and consists of forming a P1 lysate from the donor strain and transferring this lysate to the recipient strain.

Transductants were selected by tetracycline resistance (15 μg/mL) on LB plates and scored for ultraviolet light sensitivity. The UV sensitivity test involved shining UV light at 260 nm (UVP Inc. Model R-526) from a distance of 3.1 cm from colonies on LB plates for periods of 5, 10, or 15 seconds. The transductant colonies were checked for growth and compared to recA– and recA+ controls that were also irradiated. The resulting recA deletion strain derived from AMA1004 was named BK6.

In order to obtain the parB locus, pKG1022 (Gerdes, 1988) was isolated from CSH50 using chloramphenicol amplification and CsCl centrifugation as described previously (Wood and Peretti, 1989). The recipient vector pMJR1750 was isolated from AMA1004 following transformation with DNA supplied by Stark. The parB locus was excised from pKG1022 along with aphA (Kan') using Hindii (Boeh. Mann.), creating a DNA fragment of 1630 bp. The recipient plasmid pMJR1750 (7550 bp) was digested with ScaI (Boeh. Mann.) at a unique site, abolishing ampicillin resistance. The two restricted plasmids (2.5 μg each) were dialyzed and blunt-end ligated (Rodriguez and Tait, 1983) using T4 DNA ligase (BRL). BK6 was transformed with the ligated DNA following the method of Maniatis et al. (1982).

The genetic manipulations of the host/plasmid system is extremely effective in enhancing plasmid stability. The impact of introducing the recA mutation is illustrated by the reduction in the frequency at which plasmid-free segregants arise (p) for the two hosts bearing pMJR1750. Under noninducing conditions, a 33-fold decrease in p was observed for BK6 (recA–) as the host relative to AMA1004 (recA+). The relative decrease in p due to the recA deletion was only five-fold upon IPTG induction of lacZ. The recA mutation may enhance segregational stability significantly by limiting the formation of plasmid multimers, which form readily in recA+ hosts (Bedbrook and Ausubel, 1976). Plasmid multimerization has been shown to increase segregational instability by decreasing the number of partitioning molecules (Summers and Sherratt, 1984).

A dramatic increase in plasmid stability occurred upon addition of the parB locus to the expression vector. In the absence of antibiotic selection pressure, p decreased by over ten orders of magnitude for both induced and non-induced conditions. Furthermore, chemostat stability increased to 100% at all levels of transcription induction in the presence of kanamycin using pTKW106. The original expression system, AMA1004/pMJR1750, was unstable in the chemostat even with the continuous addition of ampicillin at 400 µg/L (1.75% plasmid-bearing at 0.5 mM IPTG). This result underscores the inadequacy of the β-lactamase gene as an effective selective marker for unstable plasmids.

True partitioning loci, which aid stabilization of plasmid maintenance by increasing the fidelity of plasmid partitioning, have not proved fully effective in stabilizing high expression vectors (Skogman et al., 1983). In contrast, the parB system, which actively enforces plasmid stability through the post-segregational killing of any plasmid-free segregants that arise, effectively stabilized a fully-induced expression vector directing production of 15-20% of the total cell protein. This result is highly significant since it illustrates the potential of parB as a stabilizing element in large-scale production processes where antibiotic addition is undesirable due to its expense and the resulting contamination of the product stream (Ensley, 1985).

The genetic stabilization strategy employed in this work can be applied to any *E. coli* host/vector system. The recA mutation can be conveniently introduced into the host using P1 transduction, and plasmids with parB cassettes which allow easy manipulation of the parB gene. This allowed us to replace the -lactamase gene with the genes for kanamycin resistance and parB in a single step. Furthermore, the parB locus to be an effective plasmid-stabilizing element in a number of gram-negative strains, increasing the generality of this approach.

In addition, the host/plasmid system is a very attractive model system for kinetic studies of the impact of cloned-gene expression on cell metabolism. Gene expression of an easily assayed enzyme, β-galactosidase, can be varied almost 500-fold in a stable chemostat culture by varying IPTG concentrations in the medium. This allows molecular level responses (mRNA synthesis, ribosome population size, macromolecular stability) to be analyzed over a wide range of conditions in an effort to determine the metabolic processes most significantly affected by cloned-gene expression.

The present disclosure provides compositions comprising a non-pathogenic microorganism comprising: a first nucleic acid sequence encoding an enzyme, or functional fragment thereof; a second nucleic acid sequence encoding an polarization protein, or functional fragment thereof; and a third nucleic acid sequence encoding a toxin/antidote combination; wherein the enzyme, or functional fragment thereof, catalyzes excitation of a portion of a substrate or the release of a portion of a substrate when the substrate is present in the blood of a subject; and wherein the polarization protein facilitates the inclusion of both the first and second nucleic acid sequences in the non-pathogenic microorganism and its progeny upon cellular division. The present disclosure provides compositions comprising a non-pathogenic microorganism comprising: a first nucleic acid sequence encoding an enzyme, or functional fragment thereof; a second nucleic acid sequence encoding an polarization protein, or functional fragment thereof; and a third nucleic acid sequence encoding a toxin/antidote combination; wherein the enzyme, or functional fragment thereof, catalyzes excitation of a portion of a substrate or the release of a portion of a substrate when the substrate is present in the blood of a subject; and wherein the polarization protein facilitates the inclusion of the first, second, or third nucleic acid sequences in the non-pathogenic microorganism and its progeny upon cellular division.

In some embodiments, the non-pathogenic microorganism is a probiotic. In some embodiments, the non-pathogenic microorganism is a Gram-negative bacteria. In some embodiments, the probiotic bacteria is chosen from *Escherichia* spp., *Firmicutes* spp., *Bacteroidetes* spp., *Lactobacillus* spp., *Bifidobacteria* spp., or *Acidopholus* spp. In some embodiments, the probiotic is selected from *Lactobacillus*, *Bifidobacteria*, and *Acidopholus*. In some embodiments, the bacteria is harvested from a human or animal sample and transformed as described herein. with our system. The samples may be from stool samples (probiotics) or human/mouse tumor samples (bacteria that have potential to be very tumor selective). In some embodiments, the non-pathogenic microorganism is *E. coli* Nissle 1917 (EcN). In some embodiments, the non-pathogenic microorganism is a Gram-negative bacteria but excludes one or more of the bacterial species listed in Table 1.

In some embodiments, genetic modification of microorganism strains, could take place by transformation with plasmids, integrate into the chromosomes, and create mutations that make them less virulent or immunogenic. The possible mutations could be in amino acid synthesis (aroA, purI), virulence control (phoPQ), or in immunogenecity of LPS (msbB mutant). In some embodiments, the non-pathogenic microorganism comprises a fifth nucleic acid sequence that encodes a virulence factor. In some embodiments, the non-pathogenic microorganism comprises a fifth nucleic acid sequence that encodes a mutated gene chosen from: aroA, purI, phoPQ, msbB.

In some embodiments, the first nucleic acid sequence encoding an enzyme, or functional fragment thereof, is any enzyme, or functional fragment of the enzyme, that is capable of catalyzing excitation of a portion of a substrate or cleaving a portion of a substrate when the substrate is present in the blood of a subject. In some embodiments, the first nucleic acid sequence encoding an enzyme, or functional fragment thereof, is any enzyme, or functional fragment of the enzyme, that is capable of catalyzing excitation of a portion of a substrate or cleaving a portion of a substrate when the substrate is in the presence of the enzyme. In some embodiments, the enzyme, or functional fragment thereof, is chosen from beta-galactosidase (lacZ) and the like. Such enzyme systems are well known in the art. In some embodiments, the enzyme, or functional fragment thereof, is capable of catalyzing excitation of a portion of a substrate or cleaving a portion of a substrate so that the substrate or portion of substrate thereby emits a wavelength of light detectable by human eye under conditions sufficient to excite the substrate or portion thereof. In some embodiments, the substrate emits a visible wavelength of light when exposed to white light. In some embodiments, the substrate emits a wavelength of light visible to the human eye when exposed to white light. In some embodiments, the second nucleic acid sequence encodes a polarization protein, or functional fragment thereof, wherein the polarization protein facilitates the inclusion of the first, second, and third nucleic acid sequences in the non-pathogenic microorganism and its progeny upon cellular division. In some embodiments, the polarization protein is a cytoplasmic microtubule associated protein. In some embodiments, the polarization protein is alpA (see, Example 3 for sequence). Polarization protein systems and their use are well known in the art. A phylogenetic search was conducted and uncovered more than 35 highly divergent families of actin-like proteins (Alps) in bacteria. Their genes are found primarily on phage genomes, on plasmids and on integrating conjugative elements, and are likely to be involved in a variety of functions. Three Alps were characterized and all form filaments in the cell. The filaments of Alp7A, a plasmid partitioning protein and one of the most divergent of the Alps, display dynamic instability and also treadmill. Alp7A requires other elements from the plasmid to assemble into dynamic polymers in the cell. Most if not all of the Alps are indeed actin relatives, and that actin is very well represented in bacteria.

In some embodiments, the third nucleic acid sequence encoding a toxin/antidote combination is chosen from Hok (toxin) and Sok (antidote); fst (toxin) and RNAII (antidote); TisB (toxin) and IstR (antidote); LdrD (toxin) and RdlD (antidote); FlmA (toxin) and FlmB (antidote); Ibs (toxin) and Sib (antidote); TxpA/BrnT (toxin) and RatA (antidote); SymE (toxin) and SymR (antidote); XCV2162 (toxin) and ptaRNA1 (antidote). These systems and their use are well known to the skilled artisan. The hok/sok system of plasmid R1, which mediates plasmid stabilization via killing of plasmid-free segregants, encodes two genes: hok and sok. The hok gene product is a potent cell-killing protein. The expression of hok is regulated post-transcriptionally by the sok gene-encoded repressor, an antisense RNA complementary to the hok mRNA leader region. The sok half-life is short lived, thus cells must maintain the plasmid to produce a viable amount of antidote for the hok protein.

The present disclosure also provides kits comprising the non-pathogenic microorganism compositions described herein. In some embodiments, the kit further comprises a substrate for the enzyme, or functional fragment thereof. In some embodiments, the kit further comprises at least a first container comprising a rehydration solution and, optionally, a syringe and/or needle. Kits may also be supplied with instructional materials. Instructions may be printed on paper or other substrates, and/or may be supplied as an electronic-readable medium, such as a floppy disc, CD-ROM, DVD-ROM, zip disc, videotape, audio tape, or other readable memory storage device. Detailed instructions may not be physically associated with the kit; instead, a user may be directed to an internet web site specified by the manufacturer or distributor of the kit, or supplied as electronic mail.

The present disclosure also provides kits comprising a first container comprising any one or combination of non-pathogenic microorganism compositions described herein; and a second container comprising any effective amount of substrate disclosed herein; and optionally a detection device capable of detecting the presence, absence, or quantity of UV, infrared, or visible light emitted by a sample. The present disclosure also provides kits comprising a first container comprising any one or combination of non-pathogenic microorganism compositions described herein; and a second container comprising any effective amount of substrate disclosed herein; and optionally a detection device capable of detecting the presence, absence, or quantity of UV, infrared, or visible light emitted; and optionally a third container for urine sample collection. In some embodiments, the kits comprising a detection device that measures the intensity of light from a sample.

The present disclosure also provides a kit comprising at least a first nucleic acid molecule comprising at least one or a combination of nucleic acid sequences selected from: SEQ ID NO:4, SEQ ID NO:6, SEQ ID NO:7, SEQ ID NO:8, SEQ ID NO:10, and SEQ ID NO:11, and/or functional fragments thereof. In some embodiments, the kit comprises: (i) at least one nucleic acid molecule that comprises one or a combination of nucleic acid sequences selected from: SEQ ID NO:4, SEQ ID NO:6, SEQ ID NO:7, SEQ ID NO:8, SEQ ID NO:10, and SEQ ID NO:11, and/or functional fragments thereof and (ii) a container comprising an amount of a substrate specific for any of the enzymes disclosed herein.

The present disclosure also provides a kit comprising at least a first nucleic acid molecule comprising at least one or a combination of nucleic acid sequences selected from: SEQ ID NO: 2, SEQ ID NO:4, SEQ ID NO:6, SEQ ID NO:7, SEQ ID NO:8, SEQ ID NO:10, and SEQ ID NO:11, and/or functional fragments thereof. In some embodiments, the kit comprises: (i) at least one nucleic acid molecule that comprises one or a combination of nucleic acid sequences selected from: SEQ ID NO: 2, SEQ ID NO:4, SEQ ID NO:6, SEQ ID NO:7, SEQ ID NO:8, SEQ ID NO:10, and SEQ ID NO:11, and/or functional fragments thereof; and (ii) a container comprising an amount of a substrate specific for any of the enzymes disclosed herein.

The present disclosure also provides a kit comprising at least a first nucleic acid molecule comprising at least one or a combination of nucleic acid sequences selected from: SEQ ID NO: 3, SEQ ID NO:4, SEQ ID NO:6, SEQ ID NO:7, SEQ ID NO:8, SEQ ID NO:10, and SEQ ID NO:11, and/or functional fragments thereof. In some embodiments, the kit comprises: (i) at least one nucleic acid molecule that comprises one or a combination of nucleic acid sequences selected from: SEQ ID NO: 3, SEQ ID NO:4, SEQ ID NO:6, SEQ ID NO:7, SEQ ID NO:8, SEQ ID NO:10, and SEQ ID NO:11, and/or functional fragments thereof; and (ii) a container comprising an amount of a substrate specific for any of the enzymes disclosed herein.

The present disclosure also provides a kit comprising at least a first nucleic acid molecule comprising at least one or a combination of nucleic acid sequences selected from: SEQ ID NO:4, SEQ ID NO:6, SEQ ID NO:7, SEQ ID NO:8, SEQ ID NO: 9, SEQ ID NO:10, and SEQ ID NO:11, and/or functional fragments thereof. In some embodiments, the kit comprises: (i) at least one nucleic acid molecule that comprises one or a combination of nucleic acid sequences selected from: SEQ ID NO:4, SEQ ID NO:6, SEQ ID NO:7, SEQ ID NO:8, SEQ ID NO: 9, SEQ ID NO:10, and SEQ ID NO:11, and/or functional fragments thereof; and (ii) a container comprising an amount of a substrate specific for any of the enzymes disclosed herein.

The present disclosure also provides a kit comprising at least a first nucleic acid molecule comprising at least one or a combination of nucleic acid sequences selected from: SEQ ID NO: 2, SEQ ID NO: 3, SEQ ID NO:4, SEQ ID NO:6, SEQ ID NO:7, SEQ ID NO:8, SEQ ID NO:10, and SEQ ID NO:11, and/or functional fragments thereof. In some embodiments, the kit comprises: (i) at least one nucleic acid molecule that comprises one or a combination of nucleic acid sequences selected from: SEQ ID NO: 2, SEQ ID NO: 3, SEQ ID NO:4, SEQ ID NO:6, SEQ ID NO:7, SEQ ID NO:8, SEQ ID NO:10, and SEQ ID NO:11, and/or functional fragments thereof; and (ii) a container comprising an amount of a substrate specific for any of the enzymes disclosed herein.

The present disclosure also provides a kit comprising at least a first nucleic acid molecule comprising at least one or a combination of nucleic acid sequences selected from: SEQ ID NO: 2, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof. In some embodiments, the kit comprises: (i) at least one nucleic acid molecule that comprises one or a combination of nucleic acid sequences selected from: SEQ ID NO: 2, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof; and (ii) a container comprising an amount of a substrate specific for any of the enzymes disclosed herein.

The present disclosure also provides a kit comprising at least a first nucleic acid molecule comprising at least one or a combination of nucleic acid sequences selected from: SEQ ID NO: 3, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof. In some embodiments, the kit comprises: (i) at least one nucleic acid molecule that comprises one or a combination of nucleic acid sequences selected from: SEQ ID NO: 3, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof; and (ii) a container comprising an amount of a substrate specific for any of the enzymes disclosed herein.

The present disclosure also provides a kit comprising at least a first nucleic acid molecule comprising at least one or a combination of nucleic acid sequences selected from: SEQ ID NO: 2, SEQ ID NO: 3, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof. In some embodiments, the kit comprises: (i) at least one nucleic acid molecule that comprises one or a combination of nucleic acid sequences selected from: SEQ ID NO: 2, SEQ ID NO: 3, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof; and (ii) a container comprising an amount of a substrate specific for any of the enzymes disclosed herein.

The present disclosure also provides a kit comprising at least a first and a second nucleic acid molecules; wherein the first nucleic acid molecule comprises at least one or a combination of nucleic acid sequences selected from: SEQ ID NO:4, SEQ ID NO:6, SEQ ID NO:7, SEQ ID NO:8, SEQ ID NO:10, and SEQ ID NO:11, and/or functional fragments thereof; and wherein the second nucleic acid molecule comprises at least one or a combination of nucleic acid sequences selected from: SEQ ID NO:4, SEQ ID NO:6, SEQ ID NO:7, SEQ ID NO:8, SEQ ID NO:10, and SEQ ID NO:11, and/or functional fragments thereof. In some embodiments, the kit comprises: (i) at least two nucleic acid molecules, wherein one of the nucleic acid molecules comprises one or a combination of nucleic acid sequences selected from: SEQ ID NO:4, SEQ ID NO:6, SEQ ID NO:7, SEQ ID NO:8, SEQ ID NO:10, and SEQ ID NO:11, and/or functional fragments thereof; and wherein at least one additional nucleic acid molecule comprises one or a combination of nucleic acid sequences selected from: SEQ ID NO:4, SEQ ID NO:6, SEQ ID NO:7, SEQ ID NO:8, SEQ ID NO:10, and SEQ ID NO:11, and/or functional fragments thereof; and (ii) a container comprising an amount of a substrate specific for any of the enzymes disclosed herein.

The present disclosure also provides a kit comprising at least a first and a second nucleic acid molecules; wherein the first nucleic acid molecule comprises at least one or a combination of nucleic acid sequences selected from: SEQ ID NO: 2, SEQ ID NO:4, SEQ ID NO:6, SEQ ID NO:7, SEQ ID NO:8, SEQ ID NO:10, and SEQ ID NO:11, and/or functional fragments thereof; and wherein the second nucleic acid molecule comprises at least one or a combination of nucleic acid sequences selected from: SEQ ID NO: 2, SEQ ID NO:4, SEQ ID NO:6, SEQ ID NO:7, SEQ ID NO:8, SEQ ID NO:10, and SEQ ID NO:11, and/or functional fragments thereof. In some embodiments, the kit comprises: (i) at least two nucleic acid molecules, wherein one of the nucleic acid molecules comprises one or a combination of nucleic acid sequences selected from: SEQ ID NO: 2, SEQ ID NO:4, SEQ ID NO:6, SEQ ID NO:7, SEQ ID NO:8, SEQ ID NO:10, and SEQ ID NO:11, and/or functional fragments thereof; and wherein at least one additional nucleic acid molecule comprises one or a combination of nucleic acid sequences selected from: SEQ ID NO: 2, SEQ ID NO:4, SEQ ID NO:6, SEQ ID NO:7, SEQ ID NO:8, SEQ ID NO:10, and SEQ ID NO:11, and/or functional fragments thereof; and (ii) a container comprising an amount of a substrate specific for any of the enzymes disclosed herein.

The present disclosure also provides a kit comprising at least a first and a second nucleic acid molecules; wherein the first nucleic acid molecule comprises at least one or a combination of nucleic acid sequences selected from: SEQ ID NO: 3, SEQ ID NO:4, SEQ ID NO:6, SEQ ID NO:7, SEQ ID NO:8, SEQ ID NO:10, and SEQ ID NO:11, and/or functional fragments thereof; and wherein the second nucleic acid molecule comprises at least one or a combination of nucleic acid sequences selected from: SEQ ID NO: 3, SEQ ID NO:4, SEQ ID NO:6, SEQ ID NO:7, SEQ ID NO:8, SEQ ID NO:10, and SEQ ID NO:11, and/or functional fragments thereof. In some embodiments, the kit comprises: (i) at least two nucleic acid molecules, wherein one of the nucleic acid molecules comprises one or a combination of nucleic acid sequences selected from: SEQ ID NO: 3, SEQ ID NO:4, SEQ ID NO:6, SEQ ID NO:7, SEQ ID NO:8, SEQ ID NO:10, and SEQ ID NO:11, and/or functional fragments thereof; and wherein at least one additional nucleic acid molecule comprises one or a combination of nucleic acid sequences selected from: SEQ ID NO: 3, SEQ ID NO:4, SEQ ID NO:6, SEQ ID NO:7, SEQ ID NO:8, SEQ ID NO:10, and SEQ ID NO:11, and/or functional fragments thereof; and (ii) a container comprising an amount of a substrate specific for any of the enzymes disclosed herein.

The present disclosure also provides a kit comprising at least a first and a second nucleic acid molecules; wherein the first nucleic acid molecule comprises at least one or a combination of nucleic acid sequences selected from: SEQ ID NO:4, SEQ ID NO:6, SEQ ID NO:7, SEQ ID NO:8, SEQ ID NO:9, SEQ ID NO:10, and SEQ ID NO:11, and/or functional fragments thereof; and wherein the second nucleic acid molecule comprises at least one or a combination of nucleic acid sequences selected from: SEQ ID NO: 3, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof. In some embodiments, the kit comprises: (i) at least two nucleic acid molecules, wherein one of the nucleic acid molecules comprises one or a combination of nucleic acid sequences selected from: SEQ ID NO: 3, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof; and wherein at least one additional nucleic acid molecule comprises one or a combination of nucleic acid sequences selected from: SEQ ID NO: 3, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof; and (ii) a container comprising an amount of a substrate specific for any of the enzymes disclosed herein.

The present disclosure also provides a kit comprising at least a first and a second nucleic acid molecules; wherein the first nucleic acid molecule comprises at least one or a combination of nucleic acid sequences selected from: SEQ ID NO: 2, SEQ ID NO: 3, SEQ ID NO:4, SEQ ID NO:6, SEQ ID NO:7, SEQ ID NO:8, SEQ ID NO:10, and SEQ ID NO:11, and/or functional fragments thereof; and wherein the second nucleic acid molecule comprises at least one or a combination of nucleic acid sequences selected from: SEQ ID NO: 2, SEQ ID NO: 3, SEQ ID NO:4, SEQ ID NO:6, SEQ ID NO:7, SEQ ID NO:8, SEQ ID NO:10, and SEQ ID NO:11, and/or functional fragments thereof. In some embodiments, the kit comprises: (i) at least two nucleic acid molecules, wherein one of the nucleic acid molecules comprises one or a combination of nucleic acid sequences selected from: SEQ ID NO: 2, SEQ ID NO: 3, SEQ ID NO:4, SEQ ID NO:6, SEQ ID NO:7, SEQ ID NO:8, SEQ ID NO:10, and SEQ ID NO:11, and/or functional fragments thereof; and wherein at least one additional nucleic acid molecule comprises one or a combination of nucleic acid sequences selected from: SEQ ID NO: 2, SEQ ID NO: 3, SEQ ID NO:4, SEQ ID NO:6, SEQ ID NO:7, SEQ ID NO:8, SEQ ID NO:10, and SEQ ID NO:11, and/or functional fragments thereof; and (ii) a container comprising an amount of a substrate specific for any of the enzymes disclosed herein.

The present disclosure also provides a kit comprising at least a first and a second nucleic acid molecules; wherein the first nucleic acid molecule comprises at least one or a combination of nucleic acid sequences selected from: SEQ ID NO: 2, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof; and wherein the second nucleic acid molecule comprises at least one or a combination of nucleic acid sequences selected from: SEQ ID NO: 2, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof. In some embodiments, the kit comprises: (i) at least two nucleic acid molecules, wherein one of the nucleic acid molecules comprises one or a combination of nucleic acid sequences selected from: SEQ ID NO: 2, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof; and wherein at least one additional nucleic acid molecule comprises one or a combination of nucleic acid sequences selected from: SEQ ID NO: 2, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof; and (ii) a container comprising an amount of a substrate specific for any of the enzymes disclosed herein.

The present disclosure also provides a kit comprising at least a first and a second nucleic acid molecules; wherein the first nucleic acid molecule comprises at least one or a combination of nucleic acid sequences selected from: SEQ ID NO: 3, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof; and wherein the second nucleic acid molecule comprises at least one or a combination of nucleic acid sequences selected from: SEQ ID NO: 3, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof. In some embodiments, the kit comprises: (i) at least two nucleic acid molecules, wherein one of the nucleic acid molecules comprises one or a combination of nucleic acid sequences selected from: SEQ ID NO: 3, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof; and wherein at least one additional nucleic acid molecule comprises one or a combination of nucleic acid sequences selected from: SEQ ID NO: 3, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof; and (ii) a container comprising an amount of a substrate specific for any of the enzymes disclosed herein.

The present disclosure also provides a kit comprising at least a first and a second nucleic acid molecules; wherein the first nucleic acid molecule comprises at least one or a combination of nucleic acid sequences selected from: SEQ ID NO: 2, SEQ ID NO: 3, SEQ ID NO:4, SEQ ID NO:6, SEQ ID NO:7, SEQ ID NO:8, SEQ ID NO: 9, SEQ ID NO:10, and SEQ ID NO:11, and/or functional fragments thereof; and wherein the second nucleic acid molecule comprises at least one or a combination of nucleic acid sequences selected from: SEQ ID NO:2, SEQ ID NO:3, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof. In some embodiments, the kit comprises: (i) at least two nucleic acid molecules, wherein one of the nucleic acid molecules comprises one or a combination of nucleic acid sequences selected from: SEQ ID NO:2, SEQ ID NO: 3, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof; and wherein at least one additional nucleic acid molecule comprises one or a combination of nucleic acid sequences selected from: SEQ ID NO:2, SEQ ID NO: 3, SEQ ID NO:4, SEQ ID NO:6, SEQ ID NO:7, SEQ ID NO:8, SEQ ID NO:9, SEQ ID NO:10, and SEQ ID NO:11, and/or functional fragments thereof; and (ii) a container comprising an amount of a substrate specific for any of the enzymes disclosed herein.

The present disclosure also provides methods of diagnosing a tumor in a subject comprising: i) administering a non-pathogenic microorganism composition described herein to a subject in an effective amount; ii) administering a substrate for the enzyme, or functional fragment thereof, to the subject in an effective amount; and iii) detecting the presence or absence of the released or excited portion of the substrate in the urine of the subject.

The present disclosure also provides methods of diagnosing a metastatic tumor in a subject comprising: i) administering a non-pathogenic microorganism composition described herein to a subject in an effective amount; ii) administering a substrate for the enzyme, or functional fragment thereof, to the subject in an effective amount; and iii) detecting the presence or absence of the released or excited portion of the substrate in the urine of the subject.

In some embodiments, the non-pathogenic microorganism composition described herein is administered to the subject in the form of a dosage form such as a pill, tablet, or a capsule, or as a food product such as yogurt. In some embodiments, the composition of any one of claims 1 to 12 is administered to the subject per os. In some embodiments, the substrate is administered per intravenous injection.

In some embodiments, the substrate for the enzyme, or functional fragment thereof, is administered to the subject via a dosage form or via intravenous administration. The identity of the substrate depends upon the enzyme system selected. In some embodiments, the substrate is chosen from S-Gal, Ch-Red, and LuGal.

The cleaved portion of the substrate or excitation of a portion of the substrate as acted upon by the enzyme is detected in the urine of the subject. In those subjects having a tumor, administration of the non-pathogenic microorganism composition causes a colonization of the tumor by the non-pathogenic microorganism, whereby, rather than dying if no tumor is present, these non-pathogenic microorganism actually proliferate and expand in numbers, resulting in their presence after 48 hours upon administration. Thus, measurement of the presence or absence of the enzymatic activity (i.e., cleavage product or excitation) after a 48 hour period is indicative of the presence of a tumor. In some embodiments, the presence or absence of the released or excited portion of the substrate is determined by identifying a change in the color of the urine. In some embodiments, a period of time is allowed to elapse after step i) sufficient for colonization of the microorganism in a tumor cell, tumor tissue, or a cell associated with a hyperproliferative disorder. In some embodiments, the quantity of the released or excited portion of the substrate is determined by measuring fluorescence or emission of visible wavelengths of light when exposed to white light. In some embodiments, the quantity of the released or excited portion of the substrate is determined by colorimetric analysis.

In some embodiments, when the substrate is SGal, the presence or absence of the released or excited portion of the substrate is determined by contacting a urine sample from the subject to iron ions. In some embodiments, when the substrate is LuGal, the presence or absence of the released or excited portion of the substrate is determined by quantifying the amount of luciferin in the urine sample of the subject.

In some embodiments, the tumor is derived from the gastrointestinal tract or urinary system of the subject. In some embodiments, the cancer cell, cancer tissue or cell associated with a hyperproliferative disorder is a cancer derived from the gastrointestinal tract or urinary system of a subject.

In some embodiments, the presence or absence of the released or excited portion of the substrate is determined by quantifying the amount of released or excited portion of the substrate present in the subject at one or a plurality of sites in the subject. In some embodiments, The present disclosure also provides methods of quantifying the number of cancer cells in a cell sample comprising: i) contacting the cell sample with a non-pathogenic microorganism composition described herein to form a mixture; ii) exposing the mixture to a substrate for the enzyme, or functional fragment thereof; and iii) measuring the amount of the released or excited portion of the substrate in the mixture. The greater the amount of released or excited portion of the substrate, the greater the number of non-pathogenic microorganism and, hence, the greater number of tumor cells.

The present disclosure also provides methods of detecting a cancer cell, cancer tissue, or cell associated with a hyperproliferative disorder in a subject comprising: i) administering non-pathogenic microorganism composition described herein to the subject; ii) administering a substrate for the enzyme, or functional fragment thereof, to the subject; and iii) detecting the presence or absence of the released portion of the substrate.

The present disclosure also provides any one or more of the foregoing non-pathogenic microorganism compositions described herein for detecting the presence of a tumor in a subject.

The present disclosure also provides any one or more of the foregoing non-pathogenic microorganism compositions described herein for use in the manufacture of a product for detecting the presence of a tumor in a subject.

The present disclosure also provides uses of any one or more of the foregoing non-pathogenic microorganism compositions described herein for detecting the presence of a tumor in a subject.

The present invention also provides uses of any one or more of the foregoing non-pathogenic microorganism compositions described herein in the manufacture of a medicament for detecting the presence of a tumor in a subject.

In some embodiments, the non-pathogenic microorganism is capable of colonization after administration within about 1, 2, or 3 days. In some embodiments, the non-pathogenic microorganism is capable of being cleared by the immune system or body after administration within about 2, 3, 4, 5, 6, or 7 days.

Methods

In some embodiments, methods are provided which use non-pathogenic microorganisms that comprise plasmids to colonize tumors and deliver proteins encodes by nucleic acid sequences in the bacteria. The non-pathogenic microorganisms that comprise plasmids comprise nucleic acid sequences that facilitate the inclusion of copies of plasmids in the progeny upon cellular division. A much larger proportion of total progeny of the non-pathogenic microorganisms remain plasmid bearing is the non-pathogenic microorganisms that comprise plasmids comprise nucleic acid sequences that facilitate the inclusion of copies of plasmids in the progeny upon cellular division compared to the proportion of plasmid bearing non-pathogenic microorganisms among the total progeny of the non-pathogenic microorganisms that comprise plasmids but that do not comprise the nucleic acid sequences that facilitate plasmid copy inclusion. In some embodiments, the nucleic acid sequences that facilitate plasmid copy inclusion include nucleic acid sequences that encode polarization protein. Polarization proteins are preferably cytoplasmic microtubule associated protein. In some embodiments, the nucleic acid sequences that facilitate plasmid copy inclusion include nucleic acid sequences that encode actin-like proteins (Alps). In some embodiments, the Alp may be AlpA or Alp7a. In some embodiments, the nucleic acid sequences that facilitate plasmid copy inclusion include nucleic acid sequences that encode a bacterial toxin and its antidote. In some embodiments, any of the many toxin-antidote combinations known in the art and/or disclosed herein may be provided. In some embodiments, the toxin-antidote combination hok/sok is provided. In some embodiment, both nucleic acid sequences that encode polarization protein and nucleic acid sequences that encode a bacterial toxin and its antidote are provided in the non-pathogenic microorganisms that comprise plasmids as the inclusion of these two elements within a non-pathogenic microorganism that comprises plasmids provides a higher level compared to level of plasmid-bearing progeny among total progeny of non-pathogenic microorganisms that comprise plasmids and that comprise one but not both of these two elements, much less the level of plasmid-bearing progeny among total progeny of non-pathogenic microorganisms that comprise plasmids and that comprise neither element. A single element provides greater plasmid retention/lower plasmid loss among progeny compared to no element. Two elements provides greater plasmid retention/lower plasmid loss among progeny compared to a single element.

In methods comprising the use of non-pathogenic microorganisms that comprise plasmids and that comprise nucleic acid sequences encoding a polarization protein and/or nucleic acid sequences encoding a toxin-antidote combination to colonize tumors in a subject, protein products encoded by nucleic acid sequences on plasmids are provided be the non-pathogenic microorganisms in the tumor for a longer duration do to the longer period of plasmid retention among generations of progeny making such methods more effective in producing proteins encoded by non-pathogenic microorganisms in tumors. In methods in which the non-pathogenic microorganisms that comprise plasmids are used to deliver proteins involved in therapeutic processes or effects, non-pathogenic microorganisms that comprise plasmids which encode therapeutically relevant proteins and that comprise nucleic acid sequences encoding a polarization protein and/or nucleic acid sequences encoding a toxin-antidote combination to colonize tumors in a subject provide improvements over similar methods in which the non-pathogenic microorganisms comprise neither nucleic acid sequences encoding a polarization protein nor nucleic acid sequences encoding a toxin-antidote combination. Therapeutically relevant proteins expressed from plasmids in non-pathogenic microorganisms that colonize tumors in a subject are known and the methods are improved as disclosed herein through the provision of nucleic acid sequences encoding a polarization protein and/or nucleic acid sequences encoding a toxin-antidote combination to effect longer plasmid retention among generations of progeny.

Likewise, in methods in which the non-pathogenic microorganisms that comprise plasmids are used to deliver proteins involved in diagnostic processes or effects, non-pathogenic microorganisms that comprise plasmids which encode diagnostically relevant proteins and that comprise nucleic acid sequences encoding a polarization protein and/or nucleic acid sequences encoding a toxin-antidote combination to colonize tumors in a subject provide improvements over similar methods in which the non-pathogenic microorganisms comprise neither nucleic acid sequences encoding a polarization protein nor nucleic acid sequences encoding a toxin-antidote combination. Diagnostically relevant proteins expressed from plasmids in non-pathogenic microorganisms that colonize tumors in a subject are known and the methods are improved as disclosed herein through the provision of nucleic acid sequences encoding a polarization protein and/or nucleic acid sequences encoding a toxin-antidote combination to effect longer plasmid retention among generations of progeny. In some embodiments, the diagnostically relevant proteins are those encoded by nucleic acid sequences on plasmids are described herein such as enzymes which process substrates that can be used in analysis of urine to determine if enzymes are present in the subject, indicating the presence of tumors colonized by the non-pathogenic microorganism. Such methods are described herein and involve either the detection in a subject's urine of products of enzyme processing of a substrate indicating the presence of enzyme, or the detection in reduced levels in a subject's urine of unprocessed substrate indicating an increase in substrate processing and thus the presence of enzyme. Typically, in such methods, the substrate is administered to the subject after time has elapsed for colonization by the non-pathogenic microorganism in a tumor present in a subject. Some methods provide a color change of urine when it contains processed substrate products, the color being directly provided by the processed substrate product. Some methods provide a color change of urine when it contains substrate products, the color being provided reactions that occur if processed substrate products are present. For example, methods may employ antibodies which bind to processed substrate products but not unprocessed substrate. Such antibodies may be contacted with a sample of urine and if processed substrate products are present, an antibody-processed substrate product complex forms. Detection of the antibody-processed substrate product complex indicated the presence of processed substrate product in the sample which indicates the presence of the enzyme produced by non-pathogenic microorganisms colonizing a tumor.

In some embodiments, the administration of non-pathogenic microorganism comprises a signal to noise ratio of no less than about 2, about 3, about 3.1, about 3.2, about 3.3, about 3.4, about 3.5. about 3.6, about 3.7, about 3.8, about 3.9, about 4.0, about 4.1, or about 4.2.

TABLE 1

Non-pathogenic Microorganisms

| Species | Plasmid | GenBank Accession no. |
|---|---|---|
| B. longum | pNAC2 | AY112723.1 |
| | pTB6 | NC_006843.1 |
| | pB44 | AY066026.1 |
| | pKJ36 | AF139129.1 |
| | pMG1 | NC_006997.1 |
| | pBLO1 | AF540971.1 |
| | p6043B | DQ458911 |
| | pNAC1 | AY112724.1 |
| | pNAL8L | AM183145.1 |
| | pKJ50 | U76614.1 |
| | pNAL8M | AM183144.1 |
| | pBIFA24 | NC_010164.1 |
| | p6043A | DQ458910 |
| | pNAC3 | AY112722.1 |
| | pDOJH10L | AF538868.1 |
| | pDOJH10S | AF538869.1 |
| | pMB1 | X84655 |
| | pSP02 | GU256055.1 |
| | pFI2576 | NC_011139.1 |
| | BLNIAS_P1 | CP002795.1 |
| | BLNIAS_P2 | CP002796.1 |
| | p157F-NC1 | AP010891.1 |
| | p157F-NC2 | AP010892.1 |
| | pBK283 | AB495342.1 |
| B. breve | pCIBb1 | AF085719.1 |
| | pNBb1 | E17316 |
| | pB21a | NC_010930.1 |
| B. pseudolongum subsp. globosum | pASV479 | NC_010877.1 |
| B. bifidum | pB80 | NC_011332.1 |
| | pBIF10 | DQ093580 |
| B. asteroides | pCIBAO89 | NC_010908.1 |
| | pAP1 | Y11549 |
| B. catenulatum | pBC1 | NC_007068.1 |
| B. pseudocatenulatum | p4M | AF359574.1 |
| Lactococcus ssp | | |
| Lactobacilli ssp | | |
| Lactobacilli fermentum, | | |
| Lactobacilli acidophilus, | | |
| Lactobacilli casei | | |
| Lactobacilli plantaru | | |
| Attenuated pathogens (known delivery vectors for DNA/antigens): | | |
| E. coli | | |
| Shigella spp | | |
| Salmonella spp | | |
| Salmonella (all substrains, including attenuated strains for tumor experiments, VNP20009 human clinical strain) | | |
| Listeria spp | | |
| Mycobacteria spp | | |
| Pseudomonas spp | | |
| Bordetella spp | | |
| Bacillus spp including B. subtilis | | |
| Staphylococci | | |
| Streptococci | | |
| Enterobacter spp | | |
| Enterococci spp | | |
| Acinetobacter spp | | |
| Vibrio spp. | | |
| Pasteurella spp. | | |
| Burkholderia spp | | |
| Other Pseudomonas spp | | |
| Edwardsiella spp | | |
| Erwinia spp | | |

TABLE 1-continued

Non-pathogenic Microorganisms

| Species | Plasmid | GenBank Accession no. |
|---|---|---|
| *Shewanella* spp (mosquito pathogen) | | |
| *Klebsiella* spp | | |
| *Chlamydia* spp | | |
| *Aeromonas* spp | | |
| Plant pathogens, optionally attenuated | | |
| *Agrobacterium* spp. | | |
| *Rhizobium* spp | | |
| *Ralstonia* spp | | |
| *Xanthomonas* spp. | | |
| *Geobacter* spp | | |
| *Photobacteria* spp | | |

In order that the subject matter disclosed herein may be more efficiently understood, examples are provided below. In order that the invention disclosed herein may be more efficiently understood, examples are provided below. It should be understood that these examples are for illustrative purposes only and are not to be construed as limiting the invention in any manner Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted. All journal articles, patent applications, issued patents or other citations disclosed in this document are incorporated by reference herein in their entireties.

TABLE 2

Hok sequence schematic

```
C
BamHI
|                                                                    -        ..=..||._
AACAAACTCCGGGAGGCAGCGTGATGCGGCAACAATCACACGGATTTCCCGTGAACGGTCTGAATGAGCGGATTATTTTCAGGGGAAAGTGAGTGTGGTCA
TTGTTTGAGGCCCTCCGTCGCACTACGCCGTTGTTAGTGTGCCTAAAGGGCACTTGCCAGACTTACTCGCCTAATAAAAGTCCCTTTCACTCACACCAGT phok hok mRNA 101                   f- &..   >                                              -          -          200
GCGTGCAGGTATATGGGCTATGATGTGCCCGGCGCTTGAGGCTTTCTGCCTCATGACGTGAAGGTGGTTTGTTGCCGTGTTGTGTGGCAGAAAGAAGATA
CGCACGTCCATATACCCGATACTACACGGGCCGCGAACTCCGAAAGACGGAGTACTGCACTTCCACCAAACAACGGCACAACACACCGTCTTTCTTCTAT mok start
201                                                                •          -          300
GCCCCGTAGTAAGTTAATTTTCATTAACCACCACGAGGCATCCCTAIGTCTAGTCCACATCAGGAYAGCCTCTTACCGCGCTTTGCGCAAGGAGAAGAAG
CGGGGCATCATTCAATTAAAAGTAATTGGTGGTGCTCCGTAGGGATACAGATCAGGTGTAGTCCtATCGGAGAATGGCGCGAAA CTCTTCTTC
                                           <-"====J        -10      psok        -35
                                             sok RNA hok start
301                    SaU3A                                        -          -          400
GCCAAACTACCACGAAGTTCCCTTGTCTGGTGTGTGTTGATCGTGTGTCTCACACTGTTGATATTCACTTATCTGACACGAAAATCGCTGTGCGAGA
CGGTACTTTGATGGTGCTTCAAGGGAACAGACCACACACAACTAGCACACAGAGTGTGACAACTATAAGTGAATAGACTGTGCTTTTAGCGACACGCTCT IV
401                                                                __  ___ _                 500
TTCGTTACAGAGAtGGACACAGGGAGGTGGCGGCTTTCATGGCTTACGAATCCGGTAAGIAQCACCTGGAGGCGGGCGCAGGCCCGCCTTTTCAGGACT
AAGCAATGTCTCTGCCTGTGTCCCTCCACCGCCGAAAGTACCGAATGCTTAGGCCATTCATCGTTGGACCTCCGCCCGCGTCCGGGCGGAAAAGTCCTGA
                                                      mok hok
                                                      stop stop            TerminaLion of
                                       V                                   truncated mRNA

SOI                •

- - -

580
GATGCTGGTCTGACTACTGAAGCGCCTTTATAAAGGGGCTGCTGGTTCGCCGGTAGCCCCTTTCTCCTTGCTGATGTTGTEcoRI
CTACGACCAGACTGATGACTTCGCGGAAATATTTCCCCGACGACCAAGCCc rATCGGGGAAAGAGGAACGACTACAACA

Termination of full length
                                           hok transcriptA
```

1. Wood, T. K., Kuhn, R. H., and Peretti, S. W. (1990) Enhanced Plasmid Stability through Post-Segregational Killing of Plasmid-Free Cells, *Abstr Pap Am Chem S* 199, 126-BIOT.
2. Wu, K., and Wood, T. K. (1994) Evaluation of the hok/sok killer locus for enhanced plasmid stability, *Biotechnology and bioengineering* 44, 912-921.
3. Riedel, C. U., Casey, P. G., Mulcahy, H., O'Gara, F., Gahan, C. G., and Hill, C. (2007) Construction of p16Slux, a novel vector for improved bioluminescent labeling of gram-negative bacteria, *Applied and environmental microbiology* 73, 7092-7095.
4. Danino, T., Mondragon-Palomino, O., Tsimring, L., and Hasty, J. (2010) A synchronized quorum of genetic clocks, *Nature* 463, 326-330.
5. Danino, T. P., A.; Hasty, J.; Bhatia, S.; (2013) Measuring Growth and Gene Expression Dynamics of Tumor-Targeted *S. Typhimurium* Bacteria, *JoVE*.
6. Reticker-Flynn, N. E., Malta, D. F. B., Winslow, M. M., Lamar, J. M., Xu, M. J., Underhill, G. H., Hynes, R. O., Jacks, T. E., and Bhatia, S. N. (2012) A combinatorial extracellular matrix platform identifies cell-extracellular matrix interactions that correlate with metastasis, *Nat Commun* 3.
7. Winslow, M. M., Dayton, T. L., Verhaak, R. G. W., Kim-Kiselak, C., Snyder, E. L., Feldser, D. M., Hubbard, D. D., DuPage, M. J., Whittaker, C. A., Hoersch, S., Yoon, S., Crowley, D., Bronson, R. T., Chiang, D. Y., Meyerson, M., and Jacks, T. (2011) Suppression of lung adenocarcinoma progression by Nkx2-1, *Nature* 473, 101-U120.
8. Wood, T. K., Kuhn, R. H., and Peretti, S. W. (1990) Enhanced Plasmid Stability through Post-Segregational Killing of Plasmid-Free Cells, *Abstracts of Papers of the American Chemical Society* 199, 126-BIOT.
9. Derman, A. I., Becker, E. C., Truong, B. D., Fujioka, A., Tucey, T. M., Erb, M. L., Patterson, P. C., and Pogliano, J. (2009) Phylogenetic analysis identifies many uncharacterized actin-like proteins (Alps) in bacteria: regulated polymerization, dynamic instability and treadmilling in Alp7A, *Mol Microbiol* 73, 534-552.
10. Helmlinger, G., Yuan, F., Dellian, M., and Jain, R. K. (1997) Interstitial pH and pO2 gradients in solid tumors in vivo: high-resolution measurements reveal a lack of correlation, *Nature medicine* 3, 177-182.
11. Vaupel, P., Kallinowski, F., and Okunieff, P. (1989) Blood flow, oxygen and nutrient supply, and metabolic microenvironment of human tumors: a review, *Cancer research* 49, 6449-6465.
12. Gerdes, K. (1988) The Parb (Hok Sok) Locus of Plasmid-R1-a General-Purpose Plasmid Stabilization System, *Bio-Technology* 6, 1402-1405.
13. Ruoslahti, E., Bhatia, S. N., and Sailor, M. J. (2010) Targeting of drugs and nanoparticles to tumors, *J Cell Biol* 188, 759-768.
14. Yager, P., Domingo, G. J., and Gerdes, J. (2008) Point-of-care diagnostics for global health, *Annu Rev Biomed Eng* 10, 107-144.
15. Schroeder, A., Heller, D. A., Winslow, M. M., Dahlman, J. E., Pratt, G. W., Langer, R., Jacks, T., and Anderson, D. G. (2012) Treating metastatic cancer with nanotechnology, *Nature reviews. Cancer* 12, 39-50.
16. Riedel, C. U., Casey, P. G., Mulcahy, H., O'Gara, F., Gahan, C. G., and Hill, C. (2007) Construction of p16Slux, a novel vector for improved bioluminescent labeling of gram-negative bacteria, *Appl Environ Microbiol* 73, 7092-7095.

Ruder, W. C., Lu, T., and Collins, J. J. (2011) Synthetic Biology Moving into the Clinic, *Science* 333, 1248-1252.

Weber, W., and Fussenegger, M. (2012) Emerging biomedical applications of synthetic biology, *Nat Rev Genet* 13, 21-35.

Lu, T. K., and Collins, J. J. (2009) Engineered bacteriophage targeting gene networks as adjuvants for antibiotic therapy, *Proceedings of the National Academy of Sciences of the United States of America* 106, 4629-4634.

Ye, H., Daoud-El Baba, M., Peng, R. W., and Fussenegger, M. (2011) A synthetic optogenetic transcription device enhances blood . . . glucose homeostasis in mice, *Science* 332, 1565-1568.

Xie, Z., Wroblewska, L., Prochazka, L., Weiss, R., and Benenson, Y. (2011) Multi-input RNAi-based logic circuit for identification of specific cancer cells, *Science* 333, 1307-1311.

Zhao, M., Yang, M., Li, X. M., Jiang, P., Baranov, E., Li, S., Xu, M., Penman, S., and Hoffman, R. M. (2005) Tumor-targeting bacterial therapy with amino acid auxotrophs of GFP-expressing *Salmonella typhimurium*, *Proceedings of the National Academy of Sciences of the United States of America* 102, 755-760.

Ruoslahti, E., Bhatia, S. N., and Sailor, M. J. (2010) Targeting of drugs and nanoparticles to tumors, *J Cell Biol* 188, 759-768.

Danino, T., Lo, J., Prindle, A., Hasty, J., and Bhatia, S. N. (2012) In Vivo Gene Expression Dynamics of Tumor-Targeted Bacteria, *ACS Synth Biol* 1, 465-470.

Stritzker, J., Weibel, S., Hill, P. J., Oelschlaeger, T. A., Goebel, W., and Szalay, A. A. (2007) Tumor . . . specific colonization, tissue distribution, and gene induction by probiotic *Escherichia coli* Nissle 1917 in live mice, *Int J Med Microbiol* 297, 151-162.

Wu, H. C., Tsao, C. Y., Quan, D. N., Cheng, Y., Servinsky, M. D., Carter, K. K., Jee, K. J., Terrell, J. L., Zargar, A., Rubloff, G. W., Payne, G. F., Valdes, J. J., and Bentley, W. E. (2013) Autonomous bacterial localization and gene expression based on nearby cell receptor density, *Mol Syst Biol* 9, 636.

Hwang, I. Y., Tan, M. H., Koh, E., Ho, C. L., Poh, C. L., and Chang, M. W. (2013) Reprogramming Microbes to Be Pathogen-Seeking Killers, *ACS Synth Biol*.

Ye, H., Charpin-El Hamri, G., Zwicky, K., Christen, M., Folcher, M., and Fussenegger, M. (2013) Pharmaceutically controlled designer circuit for the treatment of the metabolic syndrome, *Proceedings of the National Academy of Sciences of the United States of America* 110, 141-146.

Wei, P., Wong, W. W., Park, J. S., Corcoran, E. E., Peisajovich, S. G., Onuffer, J. J., Weiss, A., and Lim, W. A. (2012) Bacterial virulence proteins as tools to rewire kinase pathways in yeast and immune cells, *Nature* 488, 384-+.

Prindle, A., Selimkhanov, J., Danino, T., Samayoa, P., Goldberg, A., Bhatia, S. N., and Hasty, J. (2012) Genetic Circuits in *Salmonella typhimurium*, *ACS Synth Biol* 1, 458-464.

Forbes, N. S. (2010) Engineering the perfect (bacterial) cancer therapy, *Nature reviews. Cancer* 10, 785-794.

Cronin, M., Morrissey, D., Rajendran, S., El Mashad, S. M., van Sinderen, D., O'Sullivan, G. C., and Tangney, M. (2010) Orally Administered *Bifidobacteria* as Vehicles for Delivery of Agents to Systemic Tumors, *Molecular Therapy* 18, 1397-1407.

Toso, J. F., Gill, V. J., Hwu, P., Marincola, F. M., Restifo, N. P., Schwartzentruber, D. J., Sherry, R. M., Topalian, S. L., Yang, J. C., Stock, F., Freezer, L. J., Morton, K. E., Seipp, C., Haworth, L., Mavroukakis, S., White, D., MacDonald, S., Mao, J., Sznol, M., and Rosenberg, S. A. (2002) Phase I study of the intravenous administration of attenuated Salmonella typhimurium to patients with metastatic melanoma, *J Clin Oncol* 20, 142-152.

Xiang, S., Fruehauf, J., and Li, C. J. (2006) Short hairpin RNA—expressing bacteria elicit RNA interference in mammals, *Nat Biotechnol* 24, 697-702.

Brader, P., Stritzker, J., Riedl, C. C., Zanzonico, P., Cai, S., Burnazi, E. M., Ghani, E. R., Hricak, H., Szalay, A. A., Fong, Y., and Blasberg, R. (2008) *Escherichia coli* Nissle 1917 facilitates tumor detection by positron emission tomography and optical imaging, *Clin Cancer Res* 14, 2295-2302.

Soghomonyan, S. A., Doubrovin, M., Pike, J., Luo, X., Ittensohn, M., Runyan, J. D., Balatoni, J., Finn, R., Tjuvajev, J. G., Blasberg, R., and Bermudes, D. (2005) Positron emission tomography (PET) imaging of tumor-localized *Salmonella* expressing HSV1-TK, *Cancer Gene Ther* 12, 101-108.

Yu, Y. A., Shabahang, S., Timiryasova, T. M., Zhang, Q., Beltz, R., Gentschev, I., Goebel, W., and Szalay, A. A. (2004) Visualization of tumors and metastases in live animals with bacteria and vaccinia virus encoding light-emitting proteins, *Nat Biotechnol* 22, 313-320.

Anderson, J. C., Clarke, E. J., Arkin, A. P., and Voigt, C. A. (2006) Environmentally controlled invasion of cancer cells by engineered bacteria, *J Mol Biol* 355, 619-627.

Danino, T., Mondragon-Palomino, O., Tsimring, L., and Hasty, J. (2010) A synchronized quorum of genetic clocks, *Nature* 463, 326-330.

Prindle, A., Samayoa, P., Razinkov, I., Danino, T., Tsimring, L. S., and Hasty, J. (2012) A sensing array of radically coupled genetic 'biopixels', *Nature* 481, 39-44.

Wehrman, T. S., von Degenfeld, G., Krutzik, P., Nolan, G. P., and Blau, H. M. (2006) Luminescent imaging of beta-galactosidase activity in living subjects using sequential reporter—enzyme luminescence, *Nature Methods* 3, 295-301.

Kwong, G. A., von Maltzahn, G., Murugappan, G., Abu-dayyeh, O., Mo, S., Papayannopoulos, I. A., Sverdlov, D. Y., Liu, S. B., Warren, A. D., Popov, Y., Schuppan, D., and Bhatia, S. N. (2013) Mass-encoded synthetic biomarkers for multiplexed urinary monitoring of disease, *Nat Biotechnol* 31, 63-70.

EXAMPLES

Example 1

Preparing Electrocompetent Cells and Electroporations

To make about 7-8 aliquots of electro-competent cells we performed the following steps: 1) grow 5 mL strain of interest with pKD46 at 30 C overnight; 2) prepare two flasks with 1/100× dilution of overnight in 250 mL LB and grow at 30 C; 3) label 1 flask+ and the other -L-arabinose (control); 4) when the $OD_{600}$ of the cells (+pKD46) reaches 0.1 (about 1-1.5 hours for JS006-24 minutes doubling), we added L-arabinose to concentration of 0.15-1.5% to induce pKD46λ-red expression; i) we added about 2 mL of 25% L-arabinose to 250 mL+culture, none to -culture; 5) we continued to grow the culture at 30° C. to $OD_{600}$=0.4 (about 1-2 hours); 6) chill cells in ice-water bath 10 minutes; 7) centrifuge 10 minutes at 4000 rcf 4° C. in 35 mL nalgene centrifuge tubes (or use sterile 50 mL tubes, max spin 4 g); 8) pipette off supernatant and resuspend pellets in 1-5 mL ice-cold $dH_2O$ (filtered); 9) centrifuge 10 min at 4000 rcf 4° C.; 10) pipette off all dH20 carefully; 11) optionall, perform another spin wash step in ice-cold $dH_2O$; 12) resuspend pellet in 1000 µL $dH_2O$+10-15% glycerol; and 13) aliquot 50 uL per tube (prechilled).

Example 2

Electroporation for Insertion

For electroporation step, two conditions are included: +/−PCR fragment. Electroporation cuvettes are chilled for 5 minutes on ice (or don't need if kept in −20 C). 5 pg to 0.5 µg of PCR amplified DNA are added to cells (for genomic insertions: typically add 50-100 ng (of 50-100 ng/µL)). Electroporation apparatus is set to "Bacteria". 1 mL SOC is prepared in pipette. Take cuvette off ice, wipe metal electrodes with kimwipe. Place the cuvette into the sample chamber (quickly so no condensation on electrodes occurs). Apply the pulse by pushing the button. Remove the cuvette Immediately add 1 mL LB medium and transfer to a sterile culture tube. Incubate 60-120 min with moderate shaking at 37° C. Plate at 37° C. (for genomic insertions). If transformation doesn't work, replate in the morning (as in Datsenko procedure) after longer incubation period.

For in vitro analysis, a proxy of lacZ activity expression from plasmids was used as a marker for presence of the plasmid. Cells were grown overnight without antibiotics, where presumably many cells without a stability lose their plasmid and ability to produce lacZ. As observed, both no stability or hok systems lose expression of lacZ under inducing conditions, while the hok+alpA combined system retains significant activity.

In vivo data highlights the stability of this system. Typically 90% of bacteria lose their plasmids within 24 hours, and slightly less for the "stabilized" hok system. With hok+alpA, about 100% maintenance over the course of 2-3 days and significant maintenance over the course of a week was observed.

Example 3

Compositions Comprising Nucleic Acids Encoding Enzyme without Administration of Substrate to Subject (PROPHETIC)

A secreted enzyme can be used to achieve a better signal to noise ratio, due to cleavage of the injected substrate in the body, however, enzymes are generally too large to clear the renal filtration limit and reach the bladder. Any of the above methods to construct the aforementioned plasmids and bacterial colonies may be conducted except that the methods do not necessarily have to include the step of administering a substrate to a subject if an enzyme product produced by the non-pathogenic microorganism is of a size sufficient to pass through the renal filtration system of the kidneys and enter the urine of a subject to whom a composition comprising the non-pathogenic microorganism has been delivered. In such a system, the component enzyme will comprise a nucleic acid sequence encoding one component from a two part alpha-complementation scheme of a marker, such as beta-galactosidase. With this new scheme, a small piece of enzyme, known as the alpha fragment will be expressed in bacteria from the stabilized plasmids or the genome. Once collected in the urine, it will be mixed with purified omega fragments (the larger component of beta-galactosidase), to assemble a functional enzyme. Finally, substrate will be added to a sample of the urine taken from a subject to whom the composition had been administered to detect for the presence of the enzyme and hence presence of the bacteria and tumor. Such a substrate may be present on a stick, paper, or in a solution easily exposed to the sample.

Example 4

AlpA Sequence incorporated into the pTKW-alpA plasmid sequence.

(SEQ ID NO: 1)

```
gaatactgtttcctgtgtgaaattgttatccgctcacaattccacacattatacgagccgatgattaattgtcatatccagaacgggagtgc
gccttgagcgacacgaattatgcagtgatttacgacctgcacagccataccacagcttccgatggctgcctgacgccagaagcattgg
tgcaccgtgcagtcgatgataagctgtcaaacatgagaattaattctgcattaatgaatcggccaacgcgcggggagaggcggtttgc
gtattgggcgctcttccgcttcctcgctcactgactcgctgcgctcggtcgttcggctgcggcgagcggtatcagctcactcaaaggcg
gtaatacggttatccacagaatcaggggataacgcaggaaagaacatgtgagcaaaaggccagcaaaaggccaggaaccgtaaaa
aggccgcgttgctggcgtttttccataggctccgcccccctgacgagcatcacaaaaatcgacgctcaagtcagaggtggcgaaacc
cgacaggactataaagataccaggcgtttccccctggaagctccctcgtgcgctctcctgttccgaccctgccgcttaccggatacctg
tccgcctttctcccttcgggaagcgtggcgctttctcaatgctcacgctgtaggtatctcagttcggtgtaggtcgttcgctccaagctgg
gctgtgtgcacgaaccccccgttcagcccgaccgctgcgccttatccggtaactatcgtcttgagtccaacccggtaagacacgactta
tcgccactggcagcagccactggtaacaggattagcagagcgaggtatgtaggcggtgctacagagttcttgaagtggtggcctaact
acggctacactagaaggacagtatttggtatctgcgctctgctgaagccagttaccttcggaaaaagagttggtagctcttgatccggca
aacaaaccaccgctggtagcggtggtttttttgtttgcaagcagcagattacgcgcagaaaaaaaggatctcaagaagatcctttgatct
tttctacggggtctgacgctcagtggaacgaaatcagaagaactcgtcaagaaggcgatagaaggcgatgcgctgcgaatcgggag
cggcgataccgtaaagcacgaggaagcggtcagcccattcgccgccaagctcttcagcaatatcacgggtagccaacgctatgtcct
gatagcggtccgccacacccagccggccacagtcgatgaatccagaaaagcggccattttccaccatgatattcggcaagcaggcat
cgccatgggtcacgacgagatcctcgccgtcgggcatgcgcgccttgagcctggcgaacagttcggctggcgcgagcccctgatgc
tcttcgtccagatcatcctgatcgacaagaccggcttccatccgagtacgtgctcgctcgatgcgatgtttcgcttggtggtcgaatggg
caggtagccggatcaagcgtatgcagccgccgcattgcatcagccatgatggatactttctcggcaggagcaaggtgagatgacagg
agatcctgccccggcacttcgcccaatagcagccagtcccttcccgcttcagtgacaacgtcgagcacagctgcgcaaggaacgcc
cgtcgtggccagccacgatagccgcgctgcctcgtcctgcagttcattcagggcaccggacaggtcggtcttgacaaaaagaaccg
ggcgcccctgcgctgacagccggaacacggcggcatcagagcagccgattgtctgttgtgcccagtcatagccgaatagcctctcca
cccaagcggccggagaacctgcgtgcaatccatcttgttcaatcataacaaactccgggaggcagcgtgatgcggcaacaatcacac
ggatttcccgtgaacggtctgaatgagcggattattttcaggaaagtgagtgtggtcagcgtgcaggtatatgggctatgatgtgccc
ggcgcttgaggctttctgcctcatgacgtgaaggtggtttgttgccgtgttgtgtggcagaaagaagatagccccgtagtaagttaatttt
cattaaccaccacgaggcatccctatgtctagtccacatcaggatagcctcttaccgcgctttgcgcaaggagaagaaggccatgaaa
ctaccacgaagttcccttgtctggtgtgtgttgatcgtgtgtctcacactgttgatattcacttatctgacacgaaaatcgctgtgcgagatt
cgttacagagacggacacagggaggtggcggctttcatggcttacgaatccggtaagtagcaacctggaggcgggcgcaggcccg
ccttttcaggactgatgctggtctgactactgaagcgcctttataaaggggctgctggttcgccggtagccccttctccttgctgatgttgt
gtcaatacgggataataccgcgccacatagcagaactttaaaagtgctcatcattggaaaacgttcttcggggcgaaaactctcaagga
tcttaccgctgttgagatccagttcgatgtaacccactcgtgcacccaactgatcttcagcatcttttactttcaccagcgtttctgggtgag
caaaaacaggaaggcaaaatgccgcaaaaaagggaataagggcgacacggaaatgttgaatactcatactcttcctttttcaatattatt
gaagcatttatcagggttattgtctcatgagcggatacatatttgaatgtatttagaaaaataaacaatagggttccgcgcacatttccc
cgaaaagtgccacctgacgtgaggttcttgcaggtcggaagcataaagtgtaaagcctggggtgcctaatgagtgagctaacttacatt
aattgcgttgcgctcactgcccgctttccagtcgggaaacctgtcgtgccagctgcattaatgaatcggccaacgcgcggggagagg
cggtttgcgtattgggcgccagggtggtttttcttttcaccagtgagacgggcaacagctgattgcccttcaccgcctggccctgagaga
gttgcagcaagcggtccacgctggtttgccccagcaggcgaaaatcctgtttgatggtggttaacggcgggatataacatgagctgtct
tcggtatcgtcgtatcccactaccgagatatccgcaccaacgcgcagcccggactcggtaatggcgcgcattgcgcccagcgccatc
tgatcgttggcaaccagcatcgcagtgggaacgatgccctcattcagcatttgcatggtttgttgaaaaccggacatggcactccagtc
```

-continued

```
gccttcccgttccgctatcggctgaatttgattgcgagtgagatatttatgccagccagccagacgcagacgcgccgagacagaactta
atgggcccgctaacagcgcgatttgctggtgacccaatgcgaccagatgctccacgcccagtcgcgtaccgtcttcatgggagaaaa
taatactgttgatgggtgtctggtcagagacatcaagaaataacgccggaacattagtgcaggcagcttccacagcaatggcatcctgg
tcatccagcggatagttaatgatcagcccactgacgcgttgcgcgagaagattgtgcaccgccgctttacaggcttcgacgccgcttcg
ttctaccatcgacaccaccacgctggcacccagttgatcggcgcgagatttaatcgccgcgacaatttgcgacggcgcgtgcagggc
cagactggaggtggcaacgccaatcagcaacgactgtttgcccgccagttgttgtgccacgcggttgggaatgtaattcagctccgcc
atcgccgcttccacttttttcccgcgttttcgcagaaacgtggctggcctggttcaccacgcgggaaacggtctgataagagacaccggc
atactctgcgacatcgtataacgttactggtttcatcctgaattgactctcttccgggcgctatcatgccataccgcgaaaggttttgcacc
acctaggtcattagcctccaatcttatagtgaaactccgcaaacttcgtttcctcaatatttgggaatactcgataacttttgttcagcttttttcat
aaaaagaaattgctttaacataattttttttaaaaaactcataatcccctgcaaacaattcaaaataaaaatttattaaaagatcatgactccc
ttacttaacatattaacgacatcacccatagatgcctcttgatcaaaacaaaggctatgacgatgatccagtagaataaaataatcaacca
ggtccttattatcttcagcctgacttaacaattgctttatttcagttcttttctctatagactcatgaaccttctcctgcataatatagtcatgccat
ttattcaacagattgcctacatagggagacggtacttttttttactttggacaacatacacttccctccagctattcaaaaatcaaaactagtc
ctaatacttatcggcatcatcaaacattttaaaacacagaacatttagtacatagtgcttaatgttcaaatctcattttgatgctctgaaccca
agcatgtactgatatcatactaaacgctcaaacacaatctatacaagtttttaagataggccaaagggaataacagtatacgttagtgaa
atcccacaggaaaaatatattaaaatactaatgttctatcaaacgaacaacccttaaaaaggaacttaaaacctctgggtttttaaggaaatt
cgcatttatttagtgttttttctcttgactttgagaacttgaaactagcagaatagctgactgttctaggaaacagggcgaatttcgattgcct
atgtctgtcgcgcaaaaataaaaacggacagacataggcaatcgatcaggatttgaaactagcgtcatagagacgtctgaggtttcca
gctctgccttgctatcgccaggctttcgcctgccatgacttttttacatacaatgcttgtcctgtatgcaacttctatgggtttgtctcgtgtt
ctctcacacggtcacactcaattgtgtgccgctgcatagaagcttggccatagttgcccgcaccgtagtgcgccaagcaacctagtggt
ttatccacattctccggaccgttaatggccgtcctcgccattcaccacaagcgcagcaaggaacgcttattgtggtatatccccgggtttg
cggtggacggggcaactcctgacgtcagtttatttttacacccctaacggcagctgggtgacaaacaaaaaacgacagaaaaccacg
gtttgatacccctccaaacagtggttttctgtcgtccaaaaatagccgaaaagtgttgacgtatacacttgttttcggtaaaatgaagacata
acttaaacattgtaagtgagggcttacaaaccaagtgttcgatgctgcaacatcggacacttttttatttgtcattctttatttgtattcaattttg
caaatagctcgcaaacaaaatatgtatcatcaaatctattaaccttgttgtctgcaaacaacagggttttttgttgttttatttagaataactaga
accagaattcaatgccaaaactttcacattgacttaacttgacttttatcttacacgattttttttttgacgtaaagccccgggcctgaaatcact
tttctctactgatttcactgatttcattttattatataatcctcaaatagcctgtattcactgattttaaatgtgatttcattttattgactttagt
gatataagatgctagtattgaggaaagtgaaatcaaggagagaataaaaatatgaatatttctcgtatgaacgtggactttggaaacagtatgt
acatgaatttaattgatggttatttttttgaattgcctacaaatgtagtagagatatctaaagaagctgctgaaggaaaatttacgagtatcgt
tgaagatccggcagatttaaaggaccggttattagtttctacagttattgatgaaacagagagatattttctagttggtgaacttgctgaacc
agaagtgttaggcaaccaacacatcaagaagttacataataaagtagagtcacatattccatacgtaacattttttagctgcaactgcttatt
accaagcgctaaaaggcaaacgtgaagataatgaagttactattgaatactttcaaacaatgctaccaatttggcttcttaaaaaattggat
aagttcagtgaaatgcagaaaaggatggcatctaaatttttgggcactcaccaagtaaaggtgctgacattaggattagaaaaagagctt
actataaagtggaagatgcagcgtgcaggatcgaatctgaagtagcaagatgggcaataaagaaaaactttgacctagaagataaa
gactatgccgaacaatttaaaaattatgacgtagttttttgtgatttaggtggcggaacagatgatctagtattactaccagctggattaaaa
ccgccaaaaagtcgtgattcttttgtttctaataccgaagcaccgttttagcgcacttagaaaaattgagaaaagaaaactcctagagc
actttgatagcgttagggagcttgaaaagtttatatactcaaatattggaaaaactaagatggaacgaagagacgggaataccggtcag
aaatttgatttaactgatatcatcaaaaaatctcttaaagaatacacagaaatcaaaatagcccaagctgaaatacgttccctgcaccaa
aagataaggtttacaaataccctttattttggcggtgttggcgaggtgcttgaagaatcaattagtgtggttactgaagagagatatggccgt
gatatttctgaatcaaatcatatagttgctgaggatgcaagactgctcaacttatatggccttgaagttttaagccgcgctgaacaagtaaa
gaaacaggcaaatgaaaagaggcacaatcaatttaggtgattagaaatgggggaaaaacaaaagaattccactctttaatgtccgaac
```

-continued

```
aacacaaatgtctgatgaaatgtacgattttgttttagagcagattagtacattcagtaaaggtaagagtaagggtacctttagagagtatg cctttcagctcatagaaagggacatgcaacaacagaaagaggaacagcaaaatagagaaaaagatcgtcatgttcatgatgaattaatt gccatgagagaagaaatgaaaaagaatttcgtgatttgaggaaaaaaattgatcagggatcgatctacgtagaacacaaaacagctg atccaaagtcagcttcaaaaacgattgaagaaggtcagttaatcactgaaaaaatcactggaactattgaagaagaatacgactatgatt tttaagagcctggattaatctaggctcttttttttatgccatttaagggaggattgcatgacaaactttttttagttgcaacacagacgccctga gcaaccggcggatttgtcctactcaggagagcgttcaccgacaaacaacagataaaacgaaaggcccagtctttcgactgagcctttc gttttatttgatgcctctagcacttagactcgagcggccgcttttgacaccagaccaactggtaatggtagcgaccggcgctcagctgg aattccgccgatactgacgggctccaggagtcgtcgccaccaatccccatatggaaaccgtcgatattcagccatgtgccttcttccgc gtgcagcagatggcgatggctggtttccatcagttgctgttgactgtagcggctgatgttgaactggaagtcgccgcgccactggtgtg ggccataattcaattcgcgcgtcccgcagcgcagaccgttttcgctcgggaagacgtacggggtatacatgtctgacaatggcagatc ccagcggtcaaaacaggcggcagtaaggcggtcgggatagttttcttgcggccctaatccgagccagtttacccgctctgctacctgc gccagctggcagttcaggccaatccgcgccggatgcggtgtatcgctcgccacttcaacatcaacggtaatcgccatttgaccactac catcaatccggtaggttttccggctgataaataaggttttcccctgatgctgccacgcgtgagcggtcgtaatcagcaccgcatcagcaa gtgtatctgccgtgcactgcaacaacgctgcttcggcctggtaatggcccgccgccttccagcgttcgacccaggcgttagggtcaat gcgggtcgcttcacttacgccaatgtcgttatccagcggtgcacgggtgaactgatcgcgcagcggcgtcagcagttggtttttatcgc caatccacatctgtgaaagagagcctgactggcggttaaattgccaacgcttattacccagctcgatgcaaaaatccatttcgctggtgg tcagatgcgggatggcgtgggacgcggcgggagcgtcacactgaggttttccgccagacgccactgctgccaggcgctgatgtg cccggcttctgaccatgcggtcgcgttcggttgcactacgcgtactgtgagccagagttgcccggcgctctccggctgcggtagttca ggcagttcaatcaactgtttaccttgtggagcgacatccagaggcacttcaccgcttgccagcggcttaccatccagccgccaccatcca gtgcaggagctcgttatcgctatgacggaacaggtattcgctggtcacttcgatggtttgcccggataaacggaactggaaaaactgct gctggtgttttgcttccgtcagcgctggatgcggcgtgcggtcggcaaagaccagaccgttcatacagaactggcgatcgttcggcgt atcgccaaaatcaccgccgtaagccgaccacgggttgccgttttcatcatatttaatcagcgactgatccacccagtcccagacgaagc cgccctgtaaacggggatactgacgaaacgcctgccagtatttagcgaaaccgccaagactgttacccatcgcgtgggcgtattcgca aaggatcagcgggcgcgtctctccaggtagcgaaagccattttttgatggaccatttcggcacagccgggaagggctggtcttcatcc acgcgcgcgtacatcgggcaaataatatcggtggccgtggtgtcggctccgccgccttcatactgcaccgggcgggaaggatcgac agatttgatccagcgatacagcgcgtcgtgattagcgccgtggcctgattcattccccagcgaccagatgatcacactcgggtgattac gatcgcgctgcaccattcgcgttacgcgttcgctcatcgccggtagccagcgcggatcatcggtcagacgattcattggcaccatgcc gtgggtttcaatattggcttcatccaccacatacaggccgtagcggtcgcacagcgtgtaccacagcggatggttcggataatgcgaa cagcgcacggcgttaaagttgttctgcttcatcagcaggatatcctgcaccatcgtctgctcatccatgacctgaccatgcagaggatga tgctcgtgacggttaacgcctcgaatcagcaacggcttgccgttcagcagcagcagaccattttcaatccgcacctcgcggaaaccga catcgcaggcttctgcttcaatcagcgtgccgtcggcggtgtgcagttcaaccaccgcacgatagagattcgggatttcggcgctcca cagtttcgggttttcgacgttcagacgtagtgtgacgcgatcggcataaccaccacgctcatcgataatttcaccgccgaaaggcgcgg tgccgctggcgacctgcgtttcaccctgccataaagaaactgttacccgtaggtagtcacgcaactcgccgcacatctgaacttcagcc tccagtacagcgcggctgaaatcatcattaaagcgagtggcaacatggaaatcgctgatttgtgtagtcggtttatgcagcaacgagac gtcacggaaaatgccgctcatccgccacatatcctgatcttccagataactgccgtcactccagcgcagcaccatcaccgcgaggcg gttttctccggcgcgtaaaaatgcgctcaggtcaaattcagacggcaaacgactgtcctggccgtaaccgacccagcgcccgttgcac cacagatgaaacgccgagttaacgccatcaaaaataattcgcgtctggccttcctgtagccagctttcatcaacattaaatgtgagcgag taacaacccgtcggattctccgtgggaacaaacggcggattgaccgtaatgggataggtcacgttggtgtagatgggcgcatcgtaac cgtgcatctgccagtttgagggacgacgacagtatcggcctcaggaagatcgcactccagccagctttccggcaccgcttctggtgc cggaaaccaggcaaagcgccattcgccattcaggctgcgcaactgttgggaagggcgatcggtgcgggcctcttcgctattacgcca
```

-continued

```
gctggcgaaaggggatgtgctgcaaggcgattaagttgggtaacgccagggttttcccagtcacgacgttgtaaaacgacgggatc
tatcat
```

A full restriction map of the genetic construct with LacZ, AlpA, and sok/hok genes is depicted in FIG. 1 and is described below in Example 4.

Example 5

Plasmid pTKW106alpA

The plasmid was constructed by adding the 3.5 kb alp7AR cassette from the *B. subtilis* natto plasmid pLS20 to the pTKW106 lacZ expression vector containing the hok/sok plasmid maintenance system. The alp7AR was amplified by PCR and AvrII/NheI restriction sites were added using primers P1-2. For the purpose of cloning the alp7AR cassette into pTKW106, the entire 9 kb pTKW106 backbone was amplified and a single AvrII restriction site was added using primers P3-4. This PCR product was then digested with AvrII and ligated with the AvrII/NheI digested alp7AR insert, producing pTKW106alpA.

```
                                                     (SEQ ID NO: 12)
P1: ccacca cctagg tcattagcctccaatcttatagtg (SEQ ID NO: 13)
P2: ccacca gctagc gttgctcagggcgtct (SEQ ID NO: 14)
P3: ccacca cctagg cggcggatttgtcc P4: ccac
```

Components of the plasmid include:

```
colE1 sequence
                                                                                          (SEQ ID NO: 2)
gcgttcggctgcggcgagcggtatcagctcactcaaaggcggtaatacggttatccacagaatcaggggataacgcaggaaagaac atgtgagcaaaaggccagcaaaaggccaggaaccgtaaaaaggccgcgttgctggcgtttttccataggctccgcccccctgacga gcatcacaaaaatcgacgctcaagtcagaggtggcgaaacccgacaggactataaagataccaggcgtttccccctggaagctccct cgtgcgctctcctgttccgaccctgccgcttaccggatacctgtccgcctttctcccttcgggaagcgtggcgctttctcatagctcacgc tgtaggtatctcagttcggtgtaggtcgttcgctccaagctgggctgtgtgcacgaaccccccgttcagcccgaccgctgcgccttatcc ggtaactatcgtcttgagtccaacccggtaagacacgacttatcgccactggcagcagccactggtaacaggattagcagagcgagg tatgtaggcggtgctacagagttcttgaagtggtggcctaactacggctacactagaaggacagtatttggtatctgcgctctgctgaag ccagttaccttcggaaaaagagttggtagctcttgatccggcaaacaaaccaccgctggtagcggtggtttttttgtttgcaagcagcag attacgcgcagaaaaaaggatctcaagaagatcctttgatcttttctacggggtctgacgctcagtggaacgaaa KanR sequence
                                                                                          (SEQ ID NO: 3)
gaagaactcgtcaagaaggcgatagaaggcgatgcgctgcgaatcgggagcggcgataccgtaaagcacgaggaagcggtcagc ccattcgccgccaagctcttcagcaatatcacgggtagccaacgctatgtcctgatagcggtccgccacacccagccggccacagtc gatgaatccagaaaagcggccattttccaccatgatattcggcaagcaggcatcgccatgggtcacgacgagatcctcgccgtcggg catgcgcgccttgagcctggcgaacagttcggctggcgcgagcccctgatgctcttcgtccagatcatcctgatcgacaagaccggct tccatccgagtacgtgctcgctcgatgcgatgtttcgcttggtggtcgaatgggcaggtagccggatcaagcgtatgcagccgccgca ttgcatcagccatgatggatactttctcggcaggagcaaggtgagatgacaggagatcctgccccggcacttcgcccaatagcagcc agtcccttcccgcttcagtgacaacgtcgagcacagctgcgcaaggaacgcccgtcgtggccagccacgatagccgcgctgcctcg tcctgcagttcattcagggcaccggacaggtcggtcttgacaaaaagaaccgggcgcccctgcgctgacagccggaacacggcgg catcagagcagccgattgtctgttgtgcccagtcatagccgaatagcctctcacccaagcggccggagaacctgcgtgcaatccatc ttgttcaatcat Hok
                                                                                          (SEQ ID NO: 4)
aacaaactccgggaggcagcgtgatgcggcaacaatcacacggatttcccgtgaacggtctgaatgagcggattattttcagggaaa gtgagtgtggtcagcgtgcaggtatatgggctatgatgtgcccggcgcttgaggctttctgcctcatgacgtgaaggtggtttgttgccg tgttgtgtggcagaaagaagatagccccgtagtaagttaattttcattaaccaccacgaggcatccctatgtctagtccacatcaggatag cctcttaccgcgctttgcgcaaggagaagaaggccatgaaactaccacgaagttcccttgtctggtgtgtgttgatcgtgtgtctcacact gttgatattcacttatctgacacgaaaatcgctgtgcgagattcgttacagagacggacacagggaggtggcggctttcatggcttacg
```

-continued aatccggtaagtagcaacctggaggcgggcgcaggcccgccttttcaggactgatgctggtctgactactgaagcgcctttataaagg ggctgctggttcgccggtagccccttctccttgctgatgttgt alp7

(SEQ ID NO: 5)

tcattagcctccaatcttatagtgaaactccgcaaacttcgtttcctcaatatgggaatactcgataacttttgttcagcttttttcataaaaag aaattgctttaacataattttttttaaaaaactcataatccctgcaaacaattcaaaataaaaatttattaaaagatcatgacttcccttactta acatattaacgacatcacccatagatgcctcttgatcaaaacaaaggctatgacgatgatccagtagaataaaataatcaaccaggtcct tattatcttcagcctgacttaacaattgctttatttcagttcttttctctatagactcatgaaccttctcctgcataatatagtcatgccatttattca acagattgcctacataggagacggtacttttttttactttggacaacatacacttccctccagctattcaaaaatcaaaactagtcctaatac ttatcggcatcatcaaacattttaaaacacagaacatttagtacatagtgcttaatgttcaaatctcattttgatgctctgaacccaagcatgt actgatatcatactaaacggctcaaacacaatctatacaagttttaagataggccaaagggaataacagtatacgttagtgaaatcccac aggaaaaatatattaaaatactaatgttctatcaaacgaacaacccttaaaaaggaacttaaaacctctgggttttaaggaaattcgcattt atttagtgttttctcttgactttgagaacttgaaactagcagaatagctgactgttctaggaaacagggcgaatttcgattgcctatgtctgt cgcgcaaaaaataaaaacggacagacataggcaatcgatcaggatttgaaactagcgtcatagagacgtctgaggtttccagctctgc cttgctatcgccaggctttcgcctgccatgaccttttacatacaatgcttgtcctgtatgcaacttctatggggtttgtctcgtgttctctcac acggtcacactcaattgtgtgccgctgcatagaagcttggccatagttgcccgcaccgtagtgcgccaagcaacctagtggtttatcca cattctccggaccgttaatggccgtcctcgccattcaccacaagcgcagcaaggaacgcttattgtggtatatccccgggtttgcggtg gacggggcaactcctgacgtcagtttattttacaccccttaacggcagctgggtgacaaacaaaaaacgacagaaaaccacggtttga taccctccaaacagtggttttctgtcgtccaaaaatagccgaaaagtgttgacgtatacacttgttttcggtaaaatgaagacataacttaa acattgtaagtgagggcttacaaaccaagtgttcgatgctgcaacatcggacacttttatttgtcattcttttatttgtattcaattttgcaaata gctcgcaaacaaaatatgtatcatcaaatctattaaccttgttgtctgcaaacaacagggttttttgttgtttatttagaataactagaaccag aattcaatgccaaaactttcacattgacttaacttgacttatctttacacgatttttttttttgacgtaaagccccgggcctgaaatcacttttctct actgatttcactgatttcattttttattatataatcctcaaatagcctgtattcactgattttaaatgtgatttcattttattgactttagtgatataaga tgctagtattgaggaaagtgaaatcaaaggagagaataaaaatatgaatatttctcgtatgaacgtggactttggaaacagtatgtacatg aatttaattgatggttattttttttgaattgcctacaaatgtagtagagatatctaaagaagctgctgaaggaaaatttacgagtatcgttgaag atccggcagatttaaaggaccggttattagtttctacagttattgatgaaacagagagatattttctagttggtgaacttgctgaaccagaa gtgttaggcaaccaacacatcaagaagttacataataaagtagagtcacatattccatacgtaacattttttagctgcaactgcttattacca agcgctaaaaggcaaacgtgaagataatgaagttactattgaatactttcaaacaatgctaccaatttggcttcttaaaaaattggataagt tcagtgaaatgcagaaaaggatggcatctaaattttttgggcactcaccaagtaaaggtgctgacattaggattagaaaaagagcttacta taaaagtggaagatgcagcgtgcaggatcgaatctgaagtagcaagatgggcaataaagaaaaactttgacctagaagataaagact atgccgaacaatttaaaaattatgacgtagttttttgtgatttaggtggcggaacagatgatctagtattactaccagctggattaaaaccg ccaaaaagtcgtgattcttttgttctaataccgaagcaccgttttagcgcacttagaaaaattgagaaaagaaaaactcctagagcactt tgatagcgttagggagcttgaaaagtttatatactcaaatattggaaaaactaagatggaacgaagagacgggaataccggtcagaaat ttgatttaactgatatcatcaaaaaatctcttaaagaatacacagaaatcaaaatagcccaagctgaaaatacgttccctgcaccaaaaga taaggtttacaaatacctttattttggcggtgttggcgaggtgcttgaagaatcaattagtgtggttactgaagagagatatggccgtgata tttctgaatcaaatcatatagttgctgaggatgcaagactgctcaacttatatggccttgaagttttaagccgcgctgaacaagtaaagaa acaggcaaatgaaaagaggcacaatcaatttaggtgattagaaatggggaaaaacaaaagaattccactctttaatgtccgaacaac acaaatgtctgatgaaatgtacgattttgttttagagcagattagtacattcagtaaaggtaagagtaagggtacctttagagagtatgcctt tcagctcatagaaagggacatgcaacaacagaaagaggaacagcaaaatagagaaaaagatcgtcatgttcatgatgaattaattgcc atgagagaagaaatgaaaaaagaatttcgtgatttgaggaaaaaaattgatcaggatcgatctacgtagaacacaaaacagctgatc caaagtcagcttcaaaaacgattgaagaaggtcagttaatcactgaaaaaatcactggaactattgaagaagaatacgactatgattttta -continued agagcctggattaatctaggctcttttttttatgccatttaagggaggattgcatgacaaactttttttagttgcaacacagacgccctgagca ac Alp7A (SEQ ID NO: 6)

atgaatatttctcgtatgaacgtggactttggaaacagtatgtacatgaatttaattgatggttattttttttgaattgcctacaaatgtagtaga gatatctaaagaagctgctgaaggaaaatttacgagtatcgttgaagatccggcagatttaaaggaccggttattagtttctacagttattg atgaaacagagagatattttctagttggtgaacttgctgaaccagaagtgttaggcaaccaacacatcaagaagttacataataaagtag agtcacatattccatacgtaacattttttagctgcaactgcttattaccaagcgctaaaaggcaaacgtgaagataatgaagttactattgaa tactttcaaacaatgctaccaattttggcttcttaaaaaattggataagttcagtgaaatgcagaaaaggatggcatctaaattttttgggcact caccaagtaaaggtgctgacattaggattagaaaagagcttactataaaagtggaagatgcagcgtgcaggatcgaatctgaagtag caagatgggcaataaagaaaaactttgacctagaagataaagactatgccgaacaatttaaaaaattatgacgtagttttttttgtgatttaggt ggcggaacagatgatctagtattactaccagctggattaaaaccgccaaaaagtcgtgattcttttgtttctaataccgaagcaccgttttt agcgcacttagaaaaattgagaaaagaaaaactcctagagcactttgatagcgttagggagcttgaaaagtttatatactcaaatattgg aaaaactaagatggaacgaagacgggaataccggtcagaaatttgatttaactgatatcatcaaaaaatctcttaaagaatacacag aaatcaaaatagcccaagctgaaaatacgttccctgcaccaaaagataaggtttacaaatacctttattttggcggtgttggcgaggtgct tgaagaatcaattagtgtggttactgaagagatatggccgtgatatttctgaatcaaatcatatagttgctgaggatgcaagactgctc aacttatatggccttgaagttttaagccgcgctgaacaagtaaagaaacaggcaaatgaaaaagaggcacaatcaatttag Alp7R (SEQ ID NO: 7)

atggggaaaaacaaaagaattccactctttaatgtccgaacaacacaaatgtctgatgaaatgtacgattttgttttagagcagattagtac attcagtaaaggtaagagtaagggtaccttagagagtatgcctttcagctcatagaaagggacatgcaacaacagaaagaggaacag caaaatagagaaaagatcgtcatgttcatgatgaattaattgccatgagagaagaaatgaaaaaagaatttcgtgatttgaggaaaaaa attgatcagggatcgatctacgtagaacacaaaacagctgatccaaagtcagcttcaaaaacgattgaagaaggtcagttaatcactga aaaaatcactggaactattgaagaagaatacgactatgattttttaaga lacZ (SEQ ID NO: 8)

atgatagatcccgtcgttttacaacgtcgtgactgggaaaaccctggcgttacccaacttaatcgccttgcagcacatccccctttcgcca gctggcgtaatagcgaagaggcccgcaccgatcgcccttcccaacagttgcgcagcctgaatggcgaatggcgctttgcctggttttcc ggcaccagaagcggtgccggaaagctggctggagtgcgatcttcctgaggccgatactgtcgtcgtcccctcaaactggcagatgca cggttacgatgcgcccatctacaccaacgtgacctatcccattacggtcaatccgccgtttgttcccacggagaatccgacgggttgtta ctcgctcacatttaatgttgatgaaagctggctacaggaaggccagacgcgaattatttttgatggcgttaactcggcgtttcatctgtggt gcaacgggcgctgggtcggttacggccaggacagtcgtttgccgtctgaatttgacctgagcgcattttttacgcgccggagaaaaccg cctcgcggtgatggtgctgcgctggagtgacggcagttatctggaagatcaggatatgtggcggatgagcggcattttccgtgacgtct cgttgctgcataaaccgactacacaaatcagcgatttccatgttgccactcgctttaatgatgatttcagccgcgctgtactggaggctga agttcagatgtgcggcgagttgcgtgactacctacgggtaacagtttctttatggcagggtgaaacgcaggtcgccagcggcaccgc gcctttcggcggtgaaattatcgatgagcgtggtggttatgccgatcgcgtcacactacgtctgaacgtcgaaaacccgaaactgtgga gcgccgaaatcccgaatctctatcgtgcggtggttgaactgcacaccgccgacgcacgctgattgaagcagaagcctgcgatgtcg gtttccgcgaggtgcggattgaaaatggtctgctgctgctgaacggcaagccgttgctgattcgaggcgttaaccgtcacgagcatcat cctctgcatggtcaggtcatggatgagcagacgatggtgcaggatatcctgctgatgaagcagaacaacttaacgccgtgcgctgttc gcattatccgaaccatccgctgtggtacacgctgtgcgaccgctacggcctgtatgtggtggatgaagccaatattgaaacccacggc atggtgccaatgaatcgtctgaccgatgatccgcgctggctaccggcgatgagcgaacgcgtaacgcgaatggtgcagcgcgatcg taatcacccgagtgtgatcatctggtcgctggggaatgaatcaggccacggcgctaatcacgacgcgctgtatcgctggatcaaatct gtcgatccttcccgcccggtgcagtatgaaggcggcggagccgacaccacggccaccgatattatttgcccgatgtacgcgcgcgtg -continued gatgaagaccagcccttcccggctgtgccgaaatggtccatcaaaaaatggctttcgctacctggagagacgcgcccgctgatcctt
gcgaatacgcccacgcgatgggtaacagtcttggcggtttcgctaaatactggcaggcgtttcgtcagtatcccgtttacagggcggc
ttcgtctgggactgggtggatcagtcgctgattaaatatgatgaaaacggcaacccgtggtcggcttacggcggtgattttggcgatac
gccgaacgatcgccagttctgtatgaacggtctggtctttgccgaccgcacgccgcatccagcgctgacggaagcaaaacaccagc
agcagttttccagttccgtttatccgggcaaaccatcgaagtgaccagcgaatacctgttccgtcatagcgataacgagctcctgcact
ggatggtggcgctggatggtaagccgctggcaagcggtgaagtgcctctggatgtcgctccacaaggtaaacagttgattgaactgc
ctgaactaccgcagccggagagcgccgggcaactctggctcacagtacgcgtagtgcaaccgaacgcgaccgcatggtcagaagc
cgggcacatcagcgcctggcagcagtggcgtctggcggaaaacctcagtgtgacgctccccgccgcgtcccacgccatcccgcat
ctgaccaccagcgaaatggatttttgcatcgagctgggtaataagcgttggcaatttaaccgccagtcaggctctctttcacagatgtgg
attggcgataaaaaccaactgctgacgccgctgcgcgatcagttcacccgtgcaccgctggataacgacattggcgtaagtgaagcg
acccgcattgaccctaacgcctgggtcgaacgctggaaggcggcgggccattaccaggccgaagcagcgttgttgcagtgcacgg
cagatacacttgctgatgcggtgctgattacgaccgctcacgcgtggcagcatcaggggaaaaccttatttatcagccggaaaaccta
ccggattgatggtagtggtcaaatggcgattaccgttgatgttgaagtggcgagcgatacaccgcatccggcgcggattggcctgaac
tgccagctggcgcaggtagcagagcgggtaaactggctcggattagggccgcaagaaaactatcccgaccgccttactgccgcctg
ttttgaccgctgggatctgccattgtcagacatgtataccccgtacgtcttcccgagcgaaaacggtctgcgctgcgggacgcgcgaat
tgaattatggcccacaccagtggcgcggcgacttccagttcaacatcagccgctacagtcaacagcaactgatggaaaccagccatc
gccatctgctgcacgcggaagaaggcacatggctgaatatcgacggtttccatatggggattggtggcgacgactcctggagcccgt
cagtatcggcggaattccagctgagcgccggtcgctaccattaccagttggtctggtgtcaaaaagcggccgctcgagtctaa T1 terminator (SEQ ID NO: 9)
cggcggatttgtcctactcaggagagcgttcaccgacaaacaacagataaaacgaaaggcccagtctttcgactgagcctttcgttttat
ttgatgcctctagcac lacI (SEQ ID NO: 10)
atgaaaccagtaacgttatacgatgtcgcagagtatgccggtgtacttatcagaccgtttcccgcgtggtgaaccaggccagccacgt
ttctgcgaaaacgcgggaaaaagtggaagcggcgatggcggagagaattacattcccaaccgcgtggcacaacaactggcgggc
aaacagtcgttgctgattggcgttgccacctccagtaggccagcacgcgccgtcgcaaattgtcgcggcgattaaatctcgcgccga
tcaactgggtgccagcgtggtggtgtcgatggtagaacgaagcggcgtcgaagcctgtaaagcggcggtgcacaatcttacgcgca
acgcgtcagtgggctgatcattaactatccgctggatgaccaggatgccattgctgtggaagagcctgcactaatgttccggcgttattt
cttgatgtactgaccagacacccatcaacagtattattttacccatgaagacggtacgcgactgggcgtggagcatctggtcgcattg
ggtcaccagcaaatcgcgctgttagcgggcccattaagttctgtacggcgcgtagcgtaggctggctggcataaatatctcactcgc
aatcaaattcagccgatagcggaacgggaaggcgactggagtgccatgtccggttttcaacaaaccatgcaaatgctgaatgagggc
atcgttcccactgcgatgctggttgccaacgatcagatggcgctgggcgcaatgcgcgccattaccgagtccgggctgcgcgttggt
gcggatatctcggtagtgggatacgacgataccgaagacagacatgttatatcccgccgttaaccaccatcaaacaggattttcgcct
gctggggcaaaccagcgtggaccgcttgctgcaactactcagggccaggcggtgaagggcaatcagagttgcccgtacactggt
gaaaagaaaaaccaccaggcgcccaatacgcaaaccgcctaccccgcgcgttggccgattcattaatgcagaggcacgacagg
tttcccgactggaaagcgggcagtga placIq (SEQ ID NO: 11)
cctgaattgactctcttccgggcgctatcatgccataccgcgaaaggttttgcacca This genetic construct was transformed into the E. Coli ECN strain through the electroporation technique described above in Examples 1 and 2.

Example 6

Figure 2A:
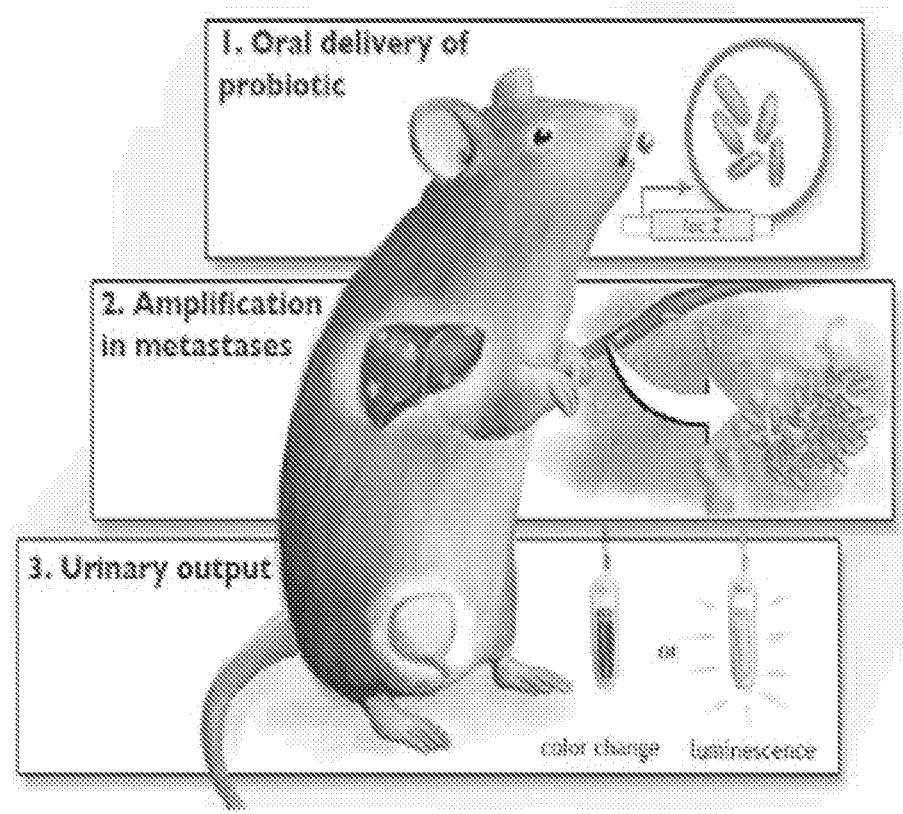
FIG. 2 depicts a summary of the diagnostic platform and accompanying data utilizing administration of a plasmid comprising the LacZ (2A) The probiotic urinary cancer diagnostic platform. EcN-lacZ is introduced systemically and specifically colonizes liver metastases. One or more commercially available substrates are injected, and activated substrate is measured in the urine. Application-specific substrates can be detected via MRI, luminescence, or visual color change. (2B) In vivo imaging screen (IVIS) images demonstrating colonization of EcN comprising nucleic acid sequences in liver metastases 24-hours following oral administration of the non-pathogenic bacteria. (2C) Quantification of activated product in the urine via luciferase assay for the EcN-lacZ platform. (2D) Instrument-free diagnosis of cancer metastasis by urinary color change.

Enzyme-Substrate Reaction Performed in Subject with Metastatic Tumor Identification Our platform consists of an engineered EcN strain containing an inducible β-galactosidase (lacZ) expression vector, together called EcN-lacZ (FIG. 2A). The EcN-lacZ system can be remotely switched ON via 20 mM IPTG drinking water, enabling rapid growth before high level lacZ expression is initiated. We used two engineered plasmid maintenance systems (hok and alp7A) to ensure efficient propagation of the lacZ expression vector in vivo. This combination of toxin-antitoxin (hok) and dynamic filament (alp7A) maintenance systems results in a substantial increase in the number of stable generations at full lacZ expression. We chromosomally integrated a luciferase expression cassette to monitor EcN-lacZ colonization using our time-lapse in vivo circuit quantification platform (T. Danino et al. ACS Synth. Biol. 2012, 1, 465-470). After oral administration of EcN-lacZ cells, one or more commercially available indicator substrates are injected systemically (FIG. 2A). These substrate(s) circulate throughout the bloodstream and diffuse into the tumor environment to be cleaved by EcN-lacZ bacteria before being collected in the bladder, yielding a measurable indicator of tumor presence in the urine.

Figure 2B:
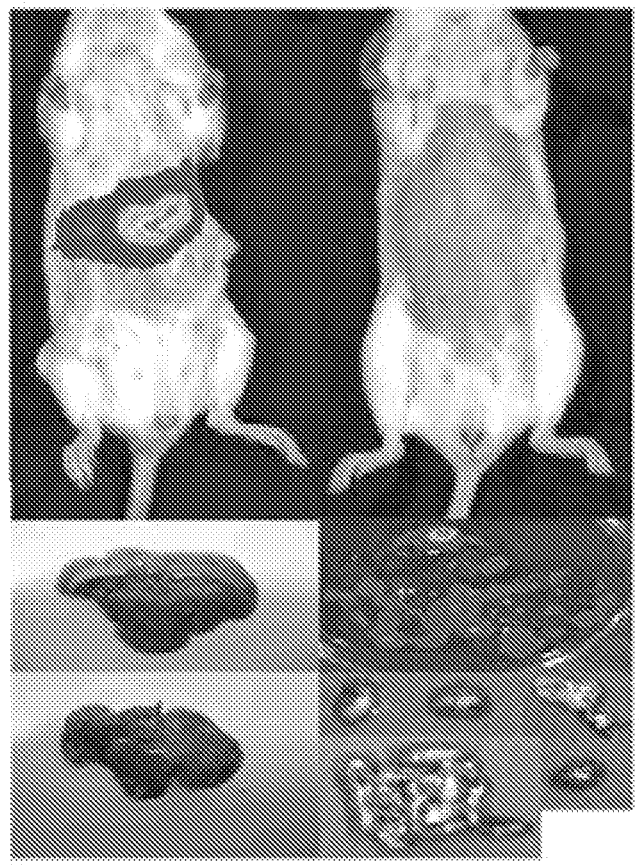

To test whether EcN-lacZ bacteria can colonize small, metastatic tumors, we orally administered EcN-lacZ cells to previously described mouse models of liver metastasis using an MC26 colorectal cell line. Roughly 24 hours following gavage with $3 \times 10^9$ EcN-lacZ bacteria, we excised the livers and observed bacterial luminescence in tumor patches for mice where EcN-lacZ bacteria were administered, but not in control tumor mice (FIG. 2B, lower left panels). Notably, the small size of these metastatic tumors meant this colonization could not be detected directly by whole-animal IVIS imaging, as in a traditional diagnostic (FIG. 2B, upper panel comparison). Tumor-specificity was verified by observing a lack of colonization in other internal organs (FIG. 2B, bottom right panels).

Figure 2C:
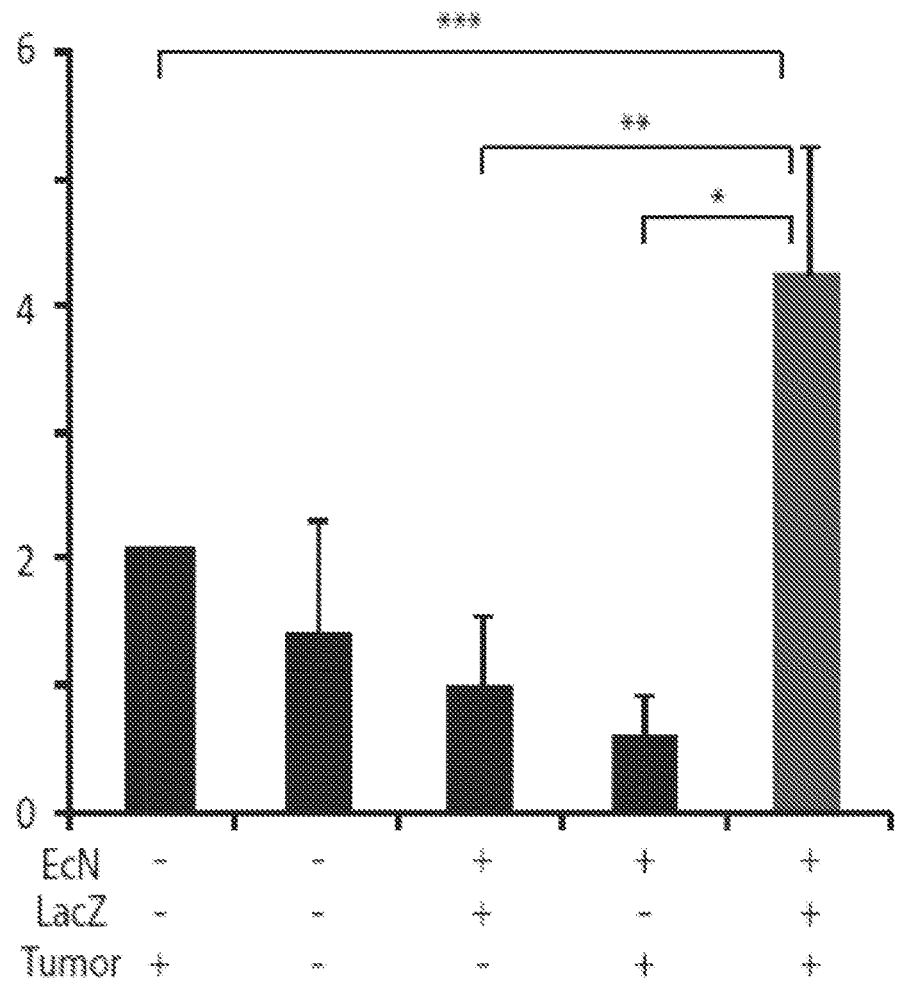
Figure 3A:
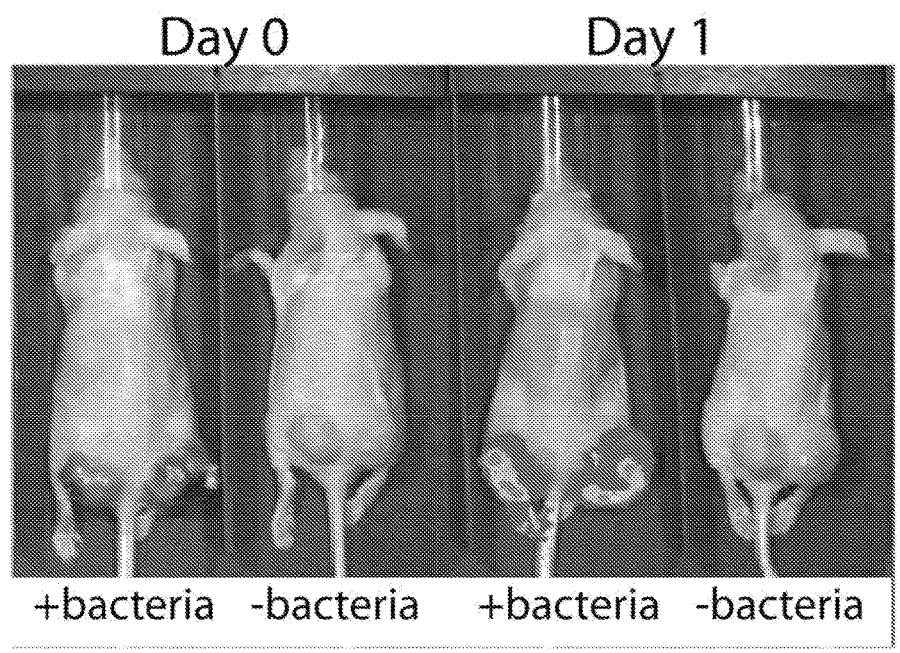
FIG. 3A demonstrates successful colonization of mice after 24 hours of administration.
Figure 2D:
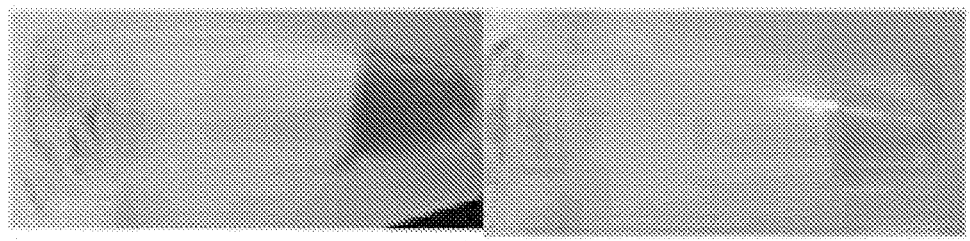

To demonstrate that our EcN-lacZ can quickly and reliably detect these tumors, we injected LuGal into EcN-lacZ, EcN, and noncolonized mice 24-hours after gavage and collected urine samples. We quantified the fraction of cleaved substrate by in vitro luciferase assays and compared the EcN-lacZ signal to either EcN or noncolonized signal (FIG. 2C). We observed clear statistical differences between the control tumor and EcN-lacZ mice (N=5, $p<0.01$) and between the EcN and EcN-lacZ mice (N=3, $p<0.001$). The results demonstrate that 4-fold increase of signal over the signal acquired by mice treated without tumors, and a 2-fold signal increase above the signal acquired from tumor background. To characterize instrument-free application, we injected CPRG to tumor-bearing and control mice. Upon collection of urine we observed a clear color change for the tumor mouse (FIG. 2D, right panel depicts yellow urine from control mice and left panel depicts red colored urine from tumor-bearing mice). A notable advantage of our diagnostic system is that it integrates the signal from all sources of tumor burden in the urine, even though individual metastases are too small to detect on their own by IVIS luminescence imaging (FIG. 2B, top panel). Thus, the EcN-lacZ diagnostic may identify the presence of small metastases sooner than conventional assays that rely on observing individual tumors. In some embodiments, the diagnostic may work within 24 hour sof administration to allow sufficient colonization of bacteria and secretion of quantities of enzyme sufficient to catalyze a reaction with a substrate whose reaction products enter the urine of a subject in detectable levels.

Our system leverages commercially available substrates to yield a versatile platform with multiple diagnostic modalities, including instrument-free methods that rely on color changes. Despite a large body of research on blood-based biomarkers for cancer, current diagnostics struggle to detect small metastases since poor circulation times. Our EcN-lacZ system combats this problem with exponential growth of the diagnostic agent, enzymatic cleavage, and signal integration in the urine. Since EcN is safe and currently prescribed in humans, this platform may function with at-home paper tests, field diagnostics, and integrated with existing medical infrastructure for urinalysis.

Example 7

Figure 3B:
FIG. 3B depicts the urine color change from mice fed bacterial compositions disclosed herein and subsequently administered with lacZ substrate as compared to urine from tumor-bearing mice without being fed the bacteria-containing compositions. A color change indicates presence of our engineered bacteria and presence of a tumor.
Figure 3C:
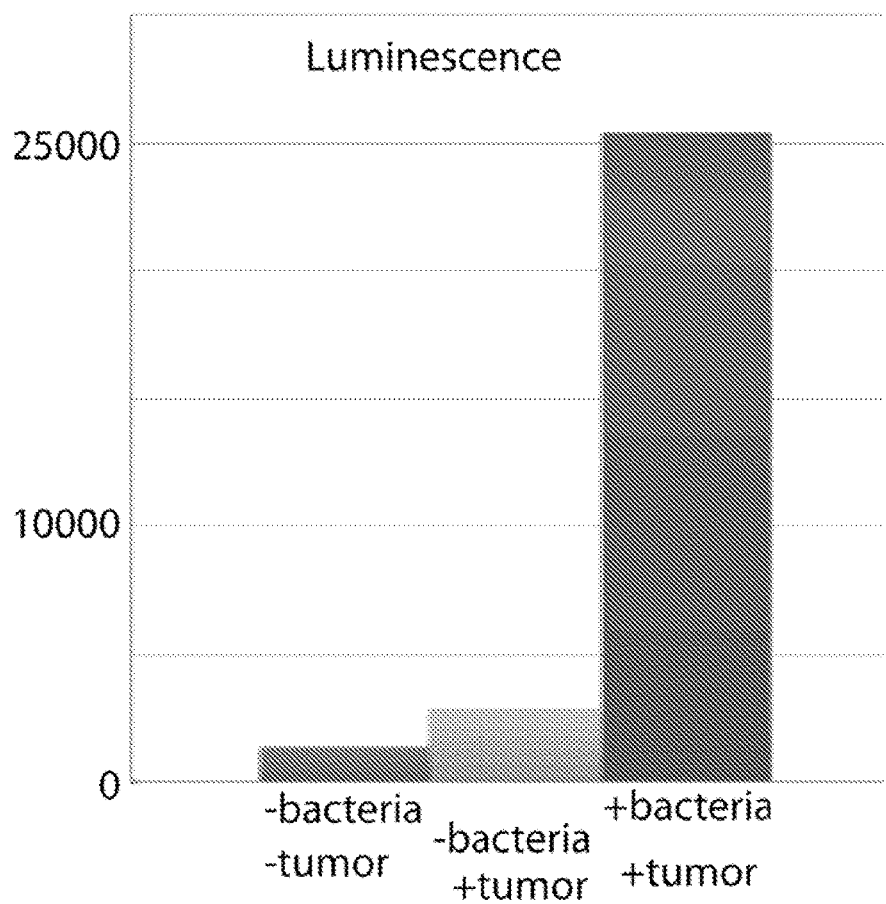
FIG. 3C depicts an experiment in which luminescence of urine is measure by a LuGal quantification assay allows for, yielding a 5-10× signal to noise ratio over control.
Figure 3D:
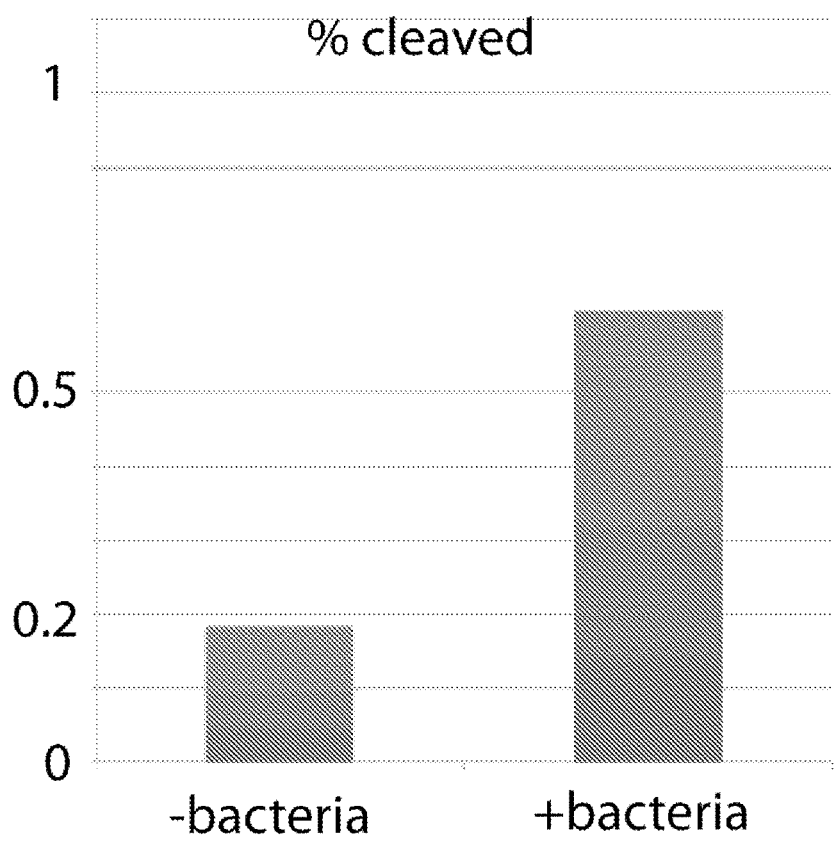
FIG. 3D depicts an experiment in which uncleaved substrate levels are measured and can be used as an additional control for determining the absence, presence or quantities of tumor cells in mice.
Figure 4:
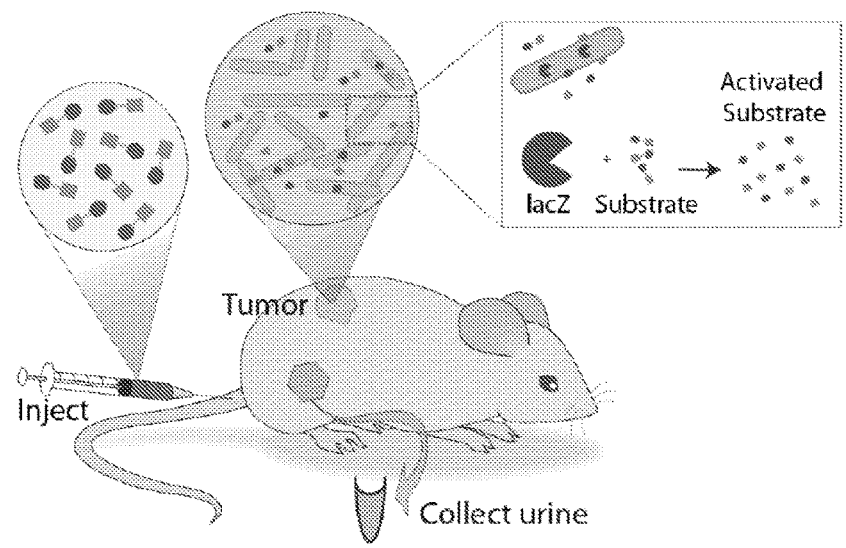
FIG. 4 depicts a schematic of how the method to tumor detection is conceptualized. Tumors are colonized by an engineered probiotic fed orally. Substrate is injected systemically and a cleavage product produces a readily-detectable color change in the urine.
Figure 5:
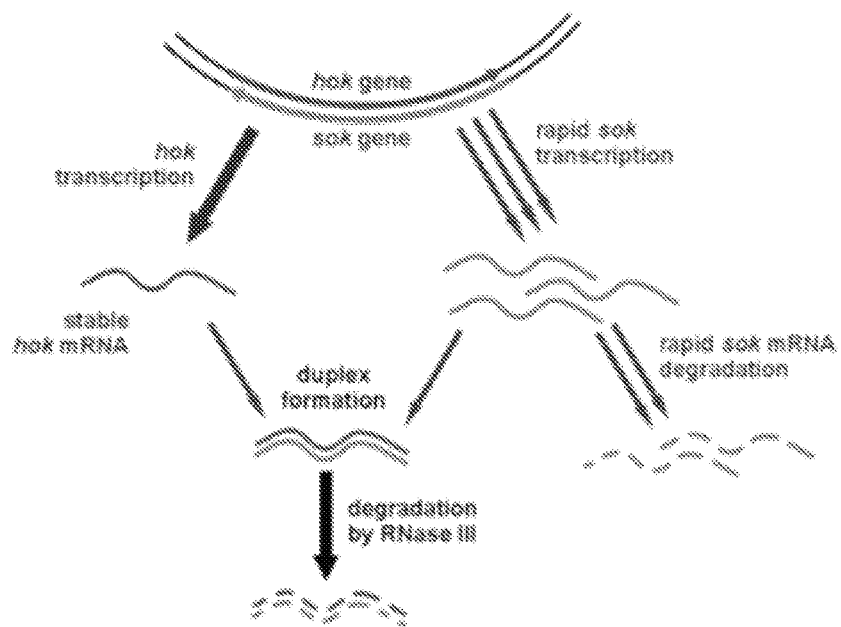
FIG. 5 depicts a schematic of the function of the hok/sok (toxin/antidote combination) in the upper panel.
Figure 5:
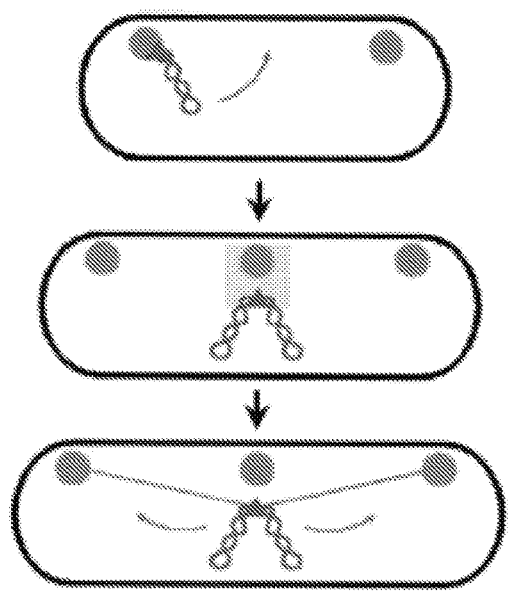

Enzyme-Substrate Reaction Performed in Subject with Non-Metastatic Tumor Identification Mice were fed compositions comprising E. Coli Nissile probiotics comprising the nucleic acid sequences comprising. Urine of the animals with and without solid tumors was collected on 96-well plates, and tested for luminescence. Results are depicted in FIG. 3. Once inside the tumor, the bacteria grow and the colony expands, reaching levels of $10^6$-$10^9$ bacteria cfu/gram in the first 24-48 hours. This leads to high level of amplification of a desired diagnostic product the bacteria will produce to create the color change. The diagnostic product can be a small molecule that diffuses into the bladder, a secreted enzyme, or a non-secreted enzyme which can cleave an additional substrate that is introduced. As a representative example, we used the Beta-galactosidase (lacZ) enzyme. LacZ is an ideal platform enzyme as it is the most highly developed biological reporter with dozens of commercially available substrates. 24 hours following colonization with oral delivery of our lacZ-expressing strain, we introduce the substrate systemically. Example substrates tested include S-Gal, Ch-Red, and LuGal which each have their own unique applications. ChRed-Gal, when cleaved produces a small molecule that changes to a purple color and can be visually detectable in the urine (FIG. 2b, see mice without tumor (yellow urine or light grey if in grey scale) versus tumor-bearing mice that excrete dark colored urine (or dark grey if in grey scale). S-Gal, when cleaved, produces a small molecule which can be detected in the urine upon $Fe^{3+}$ addition. LuGal, when cleaved, produces a luciferin molecule which can be sensitively detected in the urine with a luciferase assay. FIG. 3c shows the LuGal based assay for tumor-bearing mice injected with lacZ bacteria, tumor-bearing mice without colonized bacteria, and non-tumor mice. The signal to noise ratio is approximately 5-10-fold over background signals, which makes it straightforward to determine if a tumor exists (FIG. 3D). Together, these approaches constitute a versatile diagnosis platform leverages the dozens of commercially available substrates and existing medical infrastructure for urinalysis (UA).

Example 8

Bacterial Compositions Comprising hok System and In Vivo Plasmid Stability

Figure 6:
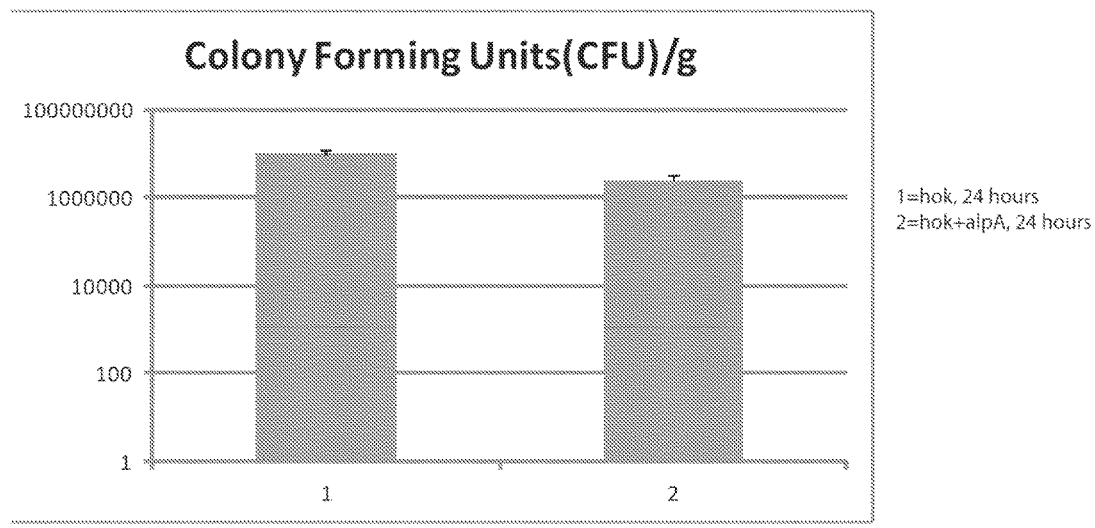
FIG. 6 depicts a measure of colony-forming units in cells transformed with hok/sok nucleic acid sequences versus cell transformed with the hok/sok nucleic acid sequences as well as the alpA nucleic acid sequence. The number of colonies in subjects administered with the both set of bacteria had similar growth rates.
Figure 7:
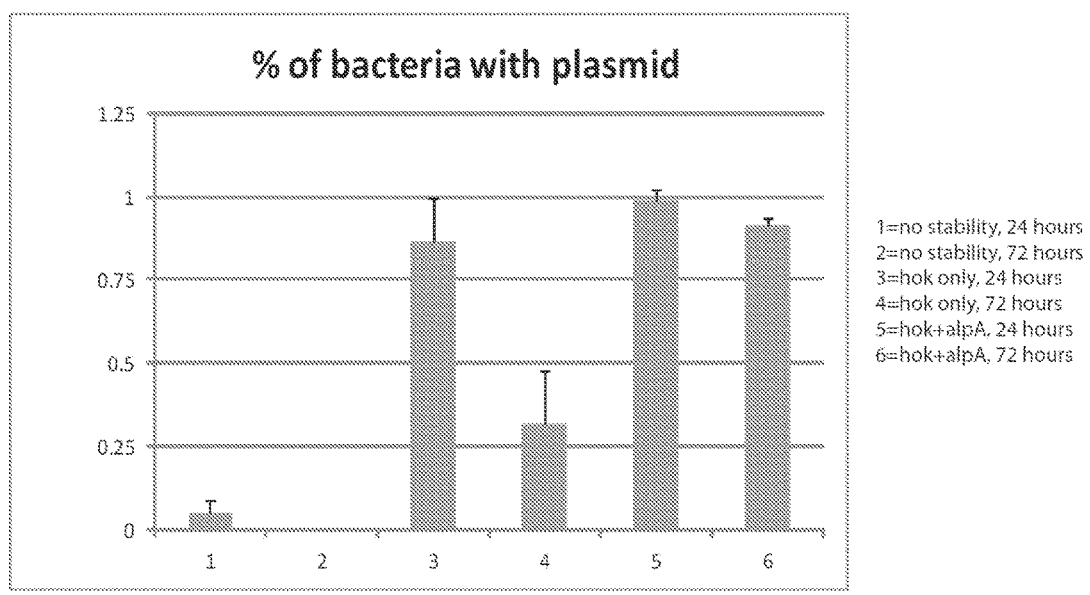
FIG. 7 depicts the stability of transformed plasmid in compositions comprising the bacteria of the present invention over a time period of 24 and 72 hours.

By increasing the plasmid stability of the plasmids in the non-pathogenic bacteria, sufficient amounts of enzyme or other proteins encoded by the nucleic acids in the bacteria can be utilized. Modified bacterial strain can become efficient vehicles for either: (i) delivering toxic payloads to tumor cells or cells associated with hyperproliferative disorders or delivering an enzyme whose reaction product can be processed at levels sufficient for detection in the urine of a subject treated with the modified bacteria. FIGS. 6 and 7 descirbe an experiment in which ECN bacteria were grown to an OD=0.4-0.8, spun down and washed with PBS 3x, and then injected into nude mice bearing colorectal tumors (LS174T) of 4-10 mm in size. After 24 or 72 hours, tumors were extracted and homogenized using a Miltenyi dissociator with 5 mL of PBS+15% glycerol. Samples were plated at appropriate dilutions and with 2-3 replicates on media containing antibiotics or no antibiotics. Counting colonies from both plates and calculating the ratio yielded a measure of the percent of bacteria within the tumor that still maintained the plasmid. N=4-5 tumors for each data point. FIGS. 6 and 7 describe the rate of growth and percent of plasmid with plasmid over certain timepoints No stability is a colE1 plasmid without hok system or alpA polarization protein; hok is a is a colE1 plasmid with hok/sok containing stable elements, and hok+alpA is a colE1 plasmid containing both hok elements and alpA stabilizing elements. The graph of FIG. 6 show that both hok and hok+alpA strains grow at a similar rate in vivo, so the plasmid loss rate is not due to bacteria dividing faster in one group versus another. FIG. 7 shows increased plasmid stability in bacteria when transformed with both AlpA genes and hok system genes and bacteria transformed with just the hok system genes. Bacteria with both AlpA genes and hok system genes demonstrate more stable plasmid stability over a 72 hour period after injection into mice.

Example 9

Manufacture, Stability, Safety and Functional Analyses

Figure 9A:
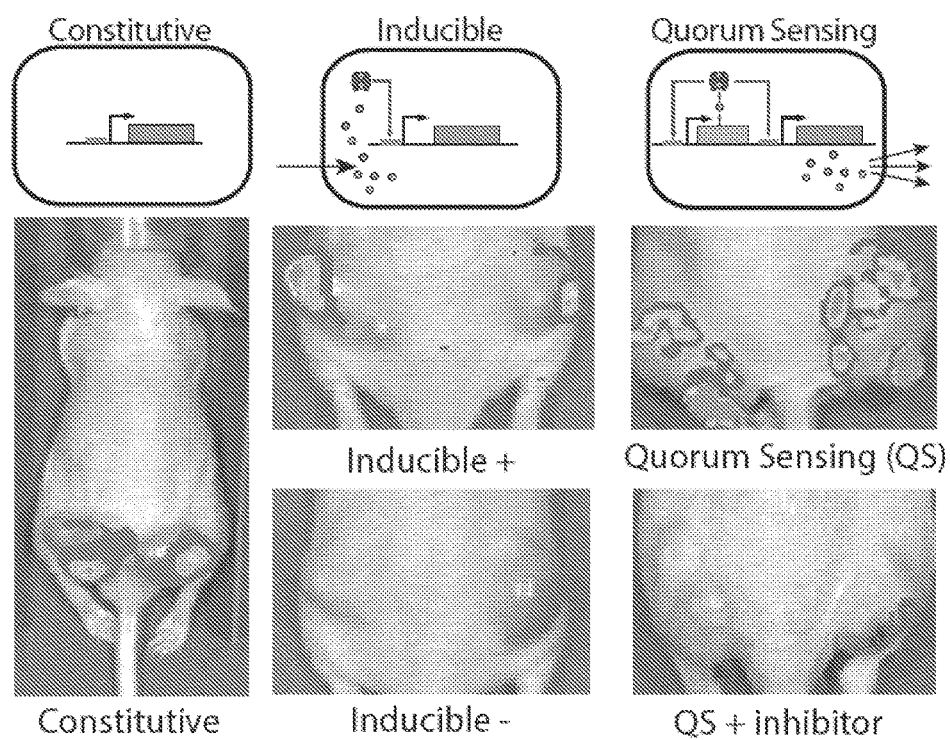
FIG. 9 depicts a summary of the dual-stabilized vector that efficiently maintains diagnostic activity in vivo. (9A) Constitutive, inducible, and quorum sensing plasmid constructs were tested in vivo using a genetically-encoded luciferase as a proxy for diagnostic activity. Inducible circuits were based on the lux promoter, where AHL was added to the drinking water at a concentration of 10 uM. For quorum sensing constructs, autonomous activation by the AHL synthase LuxI was quenched with the addition of 10 uM (Z-)-4-Bromo-5-(bromomethylene)-2(5H)-furanone to the drinking water. (9B) Dual-stabilized maintenance system ensures total plasmid stability in the tumor environment. Hok is a toxin-antitoxin system that kills daughter cells in the event of plasmid loss. Alp7 is a *B. subtilis*-derived plasmid partitioning system that efficiently segregates plasmids to cell poles during division. (9C) To quantify the performance of our maintenance systems in vitro, we successively subcultured PROP-Z bacteria daily and compared colony counts (black/white colonies on LB S-Gal plates (SI). We found nearly 100% maintenance over 72 hours with the combination of hok/sok and alp7CAR (means+−s.e.m, n=4 each). (9D) Enzymatic activity was also maintained over 72 hours in vitro. (9E) To quantify the performance of our PROP-Z diagnostic in stringent tumor microenvironment conditions, we performed growth assays under low nutrient (varying glucose %), pH, and oxygen conditions. (9F) In addition to growth, enzymatic activity was maintained by the dually-stabilized vector. (9G) Further, to quantify in vivo maintenance, we injected PROP-Z bacteria intravenously in a subcutaneous model of cancer. Tumors were homogenized daily and analyzed by colony count ratios. Plasmids were quickly lost in the absence of maintenance, hok enabled stability for 24 hours, and the combination of hok and alp7 ensure total stability for 72 hours (means+−s.e.m, n=5 each). (9H) To measure PROP-Z diagnostic amplification due to EcN growth and lacZ enzymatic turnover, we analyzed tumor homogenates taken in (c) for lacZ activity, finding a total in vivo amplification of around 5 for the relative cleavage rate from Day 3 to Day 0 (means+−s.e.m, n=5 each).

Strains & Plasmids: Plasmid pTKW106alpA was constructed by adding the 3.5 kb alp7AR cassette from the *B. subtilis* natto plasmid pLS20 to the pTKW106 lacZ expression vector containing the hok/sok plasmid maintenance system[1,2]. The alp7AR gene (SEQ ID NO:5) by PCR and added AvrII/NheI restriction sites using primers P1-2. For the purpose of cloning the alp7AR cassette into pTKW106, the entire 9 kb pTKW106 was amplified and added a single AvrII restriction site using primers P3-4. This PCR product was then digested with AvrII and ligated with the AvrII/NheI digested alp7AR insert, producing pTKW106alpA. The lux integrated strain was produced by transforming EcN bacteria with the p16Slux plasmid[3]. The plasmid with no stabilizing element (pTKW106_delhok) was created by PCR by removing the hok/sok region of pTKW106. The plasmids in FIG. 9A are the plux plasmid (Danino, et al. 2013), pTD103luxCDABE (inducible by 10 uM AHL), and pTD104luxCDABE (inhibited by (Z-)-4-Bromo-5-(bromomethylene)-2(5H)-furanone at 10 uM). The latter were constructed by replacing the GFP with lux genes in previous work[4].

Plasmid Stability and Beta-Galactosidase Activity In Vitro. Strains of *E. coli* lacZ deletion mutants (Mach One, Invitrogen) were transformed with either pTKW106, pTKW106alpA, or pTKW106_delhok. Cultures were diluted into LB media (Sigma-Aldrich) with antibiotics and no IPTG, and grown till an approximate OD=0.1. Cultures were then diluted 1/100x into deep 96 well-plates (Corning #3600) with 500 uL LB without antibiotics and grown for 24 hours. Each 24 hours, cultures were diluted 1/10,000x and grown again in an additional well plate for 24 hours. Beta-galactosidase activity was measured using a Tecan i200 plate reader by diluting wells 1-10x as needed to obtain a cleavage rate during the 5-60 min time when readings were obtained. Maximal activities were obtained from the linear portion of absorbance curve at 575 nm for each strain and each day. Each condition was replicated 4 times. Plasmid stability in 9c was calculated by plating on an LB+S-Gal and determining the number of white and black colonies[1], with the 0 hours time point being a pre-culture grown with antibiotics. In vitro activities in panel 9d are normalized for each strain at the 24 hour time point while in panel 9f, activities are normalized to the norm 1 mM condition.

Tumor Cell Lines, Animal Models and In Vivo Tests. Plasmid stability tests were performed in 6 week old nude mice (Taconic) bearing tumors from a colorectal cancer cell line, LS174T (ATCC), and tumors were grown for 1-2 weeks till they reached a size of 5-10 mm. To obtain measures of plasmid stability in vivo, EcN bacteria with pTKW plasmids were injected intravenously at a dosage of 1e6 bacteria, and tumors were steriley extracted and homogenized using a Tissue Dissociator (Miltenyi) and plated on both LB and LB with antibiotics to obtain the percent of plasmids with cells or measured for lacZ activity as mentioned above[5]. Enzyme activities of homogenates in vivo were obtained by the same method as in vitro. The liver metastasis model was generated by intraspenically injecting immunocompetent Balb/c mice (Taconic) with a luciferized, metastatic colorectal cell line (MC26 cell line, Tanabe Lab MGH)[6,7]. Animals were monitored via IVIS (IVIS 200, Calipers) for approximately 20 days. 2-5e$^9$ EcN bacteria were gavaged and drinking water was supplemented with IPTG at 10 mM concentration to induce lacZ expression. Some mice were euthanized and livers extracted for quantification and detection of bacterial luminescence via IVIS 200 (Calipers).

Urine Diagnostic Assay. Mice were injected subcutaneously with 1 ml sterile PBS 1.5 hours before tail vein injection with 100 ul Lugal[75 ul PBS, 25 ul Lugal (0.01 mg/ul)]. The Lugal injection was immediately followed by a second injection of 1 ml sterile PBS subcutaneously to allow for sufficient volume of urine to be retrieved. Mice were placed in urine collection tubes for 1-2 hours until urine appeared. 1 ul of urine was used to test for luciferin with a luciferase assay kit (Promega QuantiLum rLuciferase Kit) via luminescence in a Berthold Centro LB 960 reader.

Biodistribution/q-PCR Experiments. Organs were harvested sterilely by using a bead sterilizer for organs and washing in ethanol and then water before extraction. A small tissue sample between 10-100 mg was cut from the organ and DNA was isolated using the UltraClean Tissue&Cells DNA Isolation Kit (MoBio, Carlsbad, Calif.). 1 uL of DNA sample was used in a subsequent q-PCR experiment run according to the manufacturer's parameters (Qiagen, Quantitech SYBR Kit) on a Bio-RAD iCycler machine. Control curves were run for each qPCR experiment. Colony counts were obtained in separate experiments where whole organs were excised, homogenized in a Tissue Dissociator (Miltenyi) and plated on erythromycin to detect presence of EcN. Comparisons of colony counting from tumors and q-PCR experiments were equivalent.

Discussion

Figure 8:
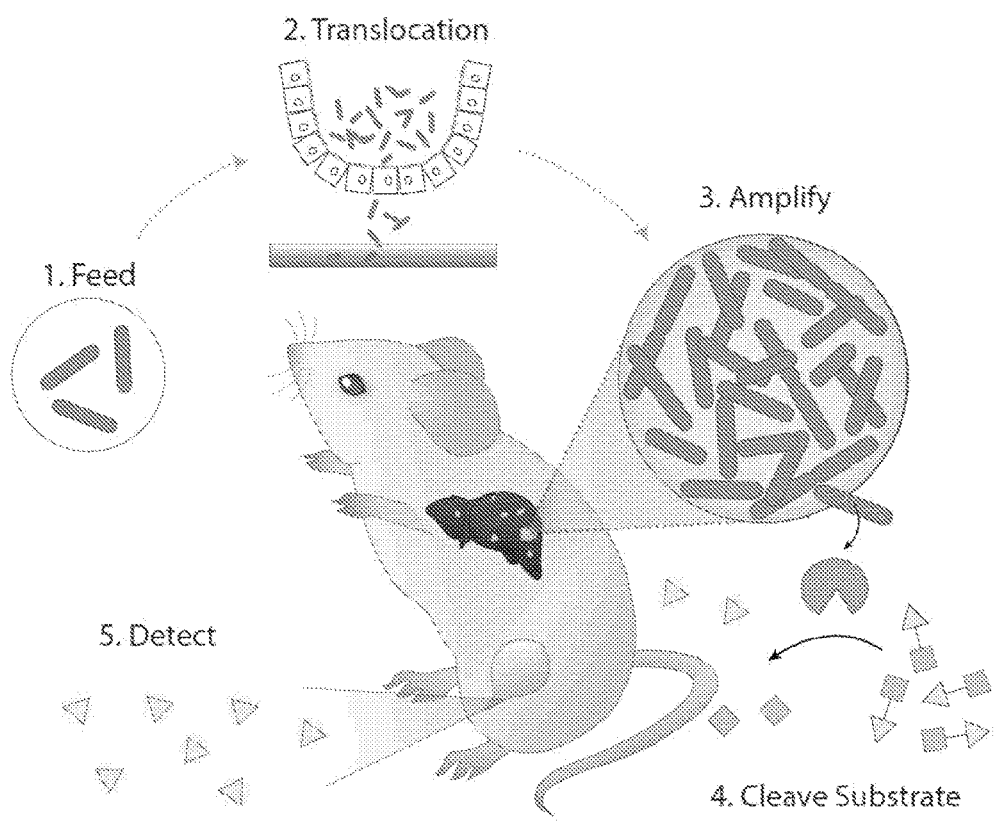
FIG. 8 depicts a schematic of the function of the PROP-Z diagnostic platform. The PROP-Z diagnostic platform is made up of probiotic *E. coli* Nissle 1917 (EcN) bacteria transformed with a dual-stabilized, high expression lacZ vector. (1) PROP-Z is delivered orally. (2) Bacteria rapidly (24 hours) translocate across the GI Tract and (3) specifically amplify within metastatic tumors in the liver. (4) PROP-Z express high levels of the lacZ enzymatic marker, enabling urinary detection via injected cleavable substrates.

The ability of certain strains of bacteria to undergo tumor-specific growth has been explored for use as a potential cancer therapy and the growing ability to engineer genetic circuits with synthetic biology now enables the design of novel therapies and diagnostics with programmed behavior. We develop a simple and noninvasive method for delivering gene circuits to systemic tumors via oral delivery of the probiotic bacterium *E. coli* Nissle 1917 (EcN) resulting in execution of EcN's genetic program within the tumor microenvironment (FIG. 8). Our platform (PROP, for programmable probiotics) merges the safe and proven delivery characteristics of probiotics such as EcN with sophisticated programmed sensing and delivery capabilities drawn from synthetic biology. To illustrate the potential of this platform to develop next-generation diagnostics by integrating with existing clinical paradigms, we describe an implementation of the platform, PROP-Z, that uses dynamic plasmid-based expression of a reporter enzyme to identify and report the presence of tumors via urinalysis, one of the most common methods of medical diagnosis.

Figure 9B:
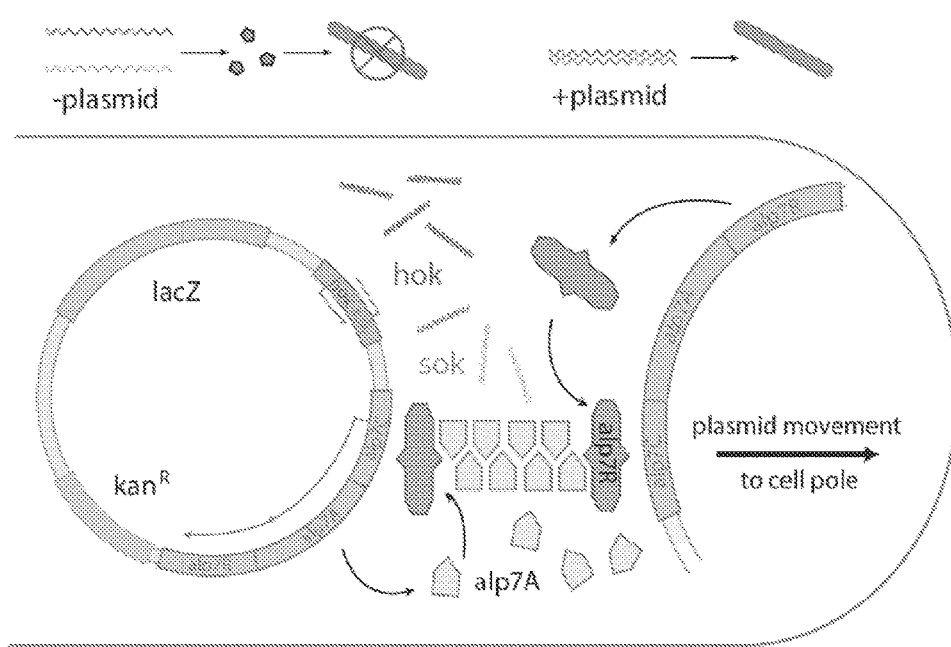
Figure 9C:
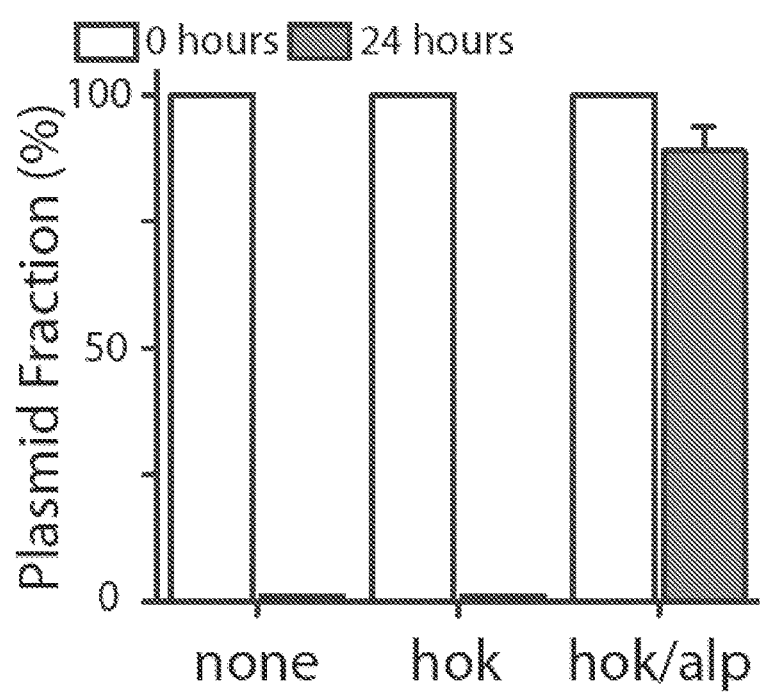
Figure 9D:
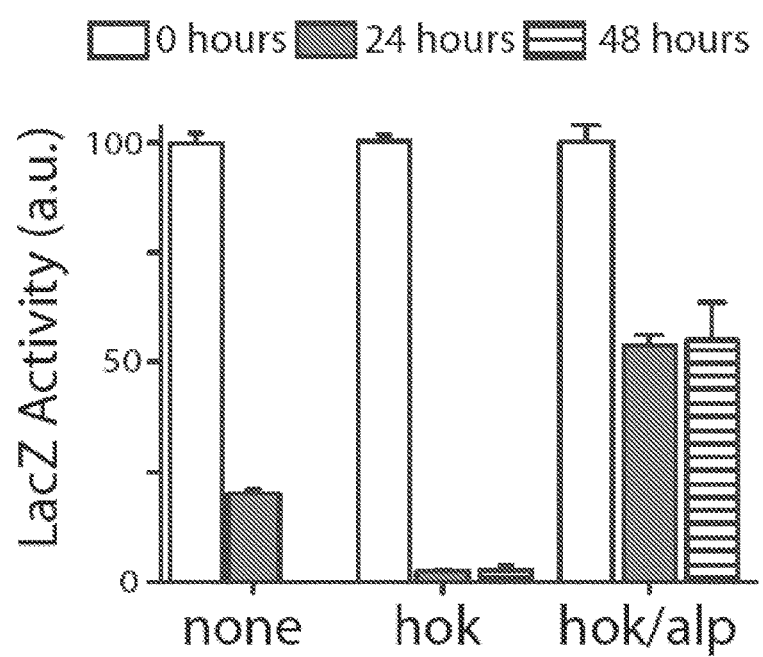
Figure 9E:
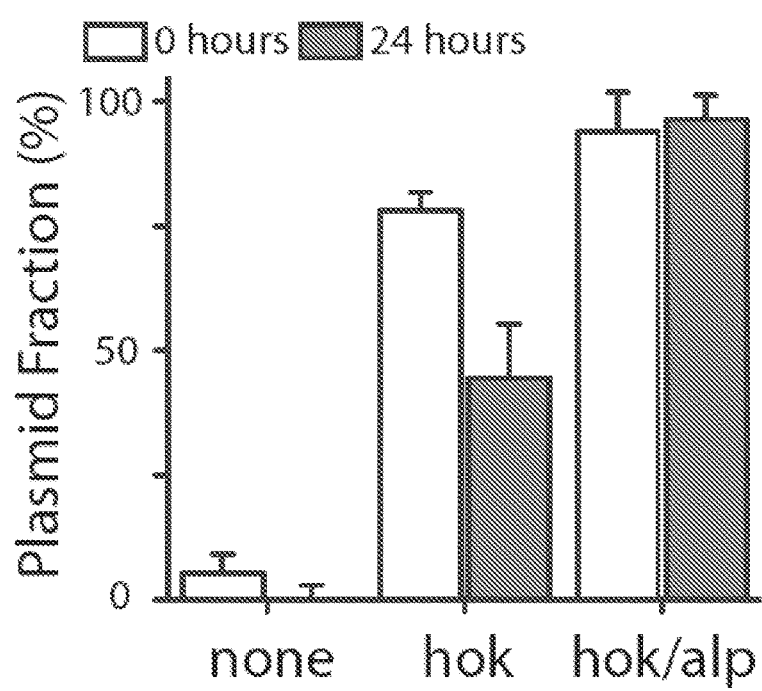
Figure 9F:
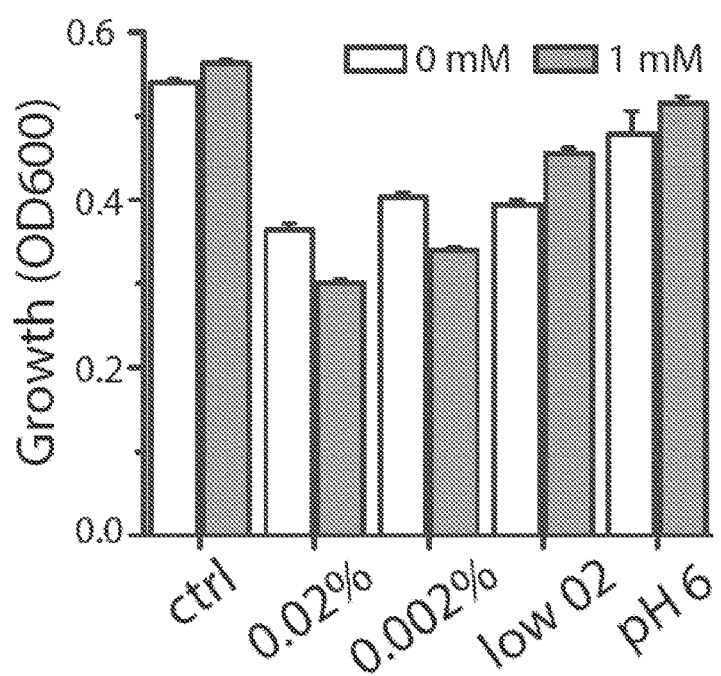
Figure 9G:
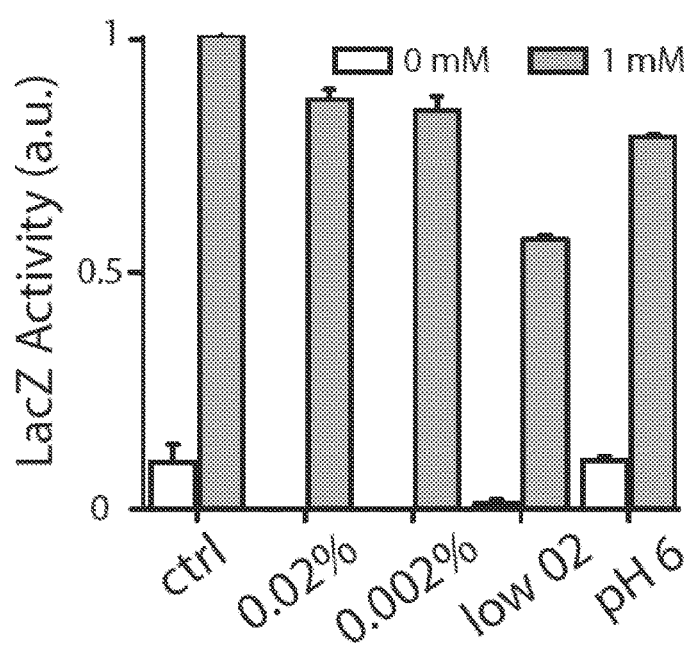

Since synthetic genetic circuits have generally been engineered using plasmids that enable high signal, low noise, and modularity, we used our PROP platform to test three different circuit architectures (constitutive, inducible, and quorum sensing) using a subcutaneous xenograft model of colorectal cancer (FIG. 9A). Here, systemically administered PROP bacteria localize in tumors and execute their programmed behavior in the tumor microenvironment following intravenous injection. Since plasmids are often unstable in nutrient-poor conditions like the tumor microenvironment[8], we engineered a dual-maintenance vector to ensure long-term stability for our PROP platform (FIG. 9B). The first maintenance device is an R1-derived toxin-antitoxin system that simultaneously produces a toxin (hok) and a short-lived antitoxin (sok), killing the cell in the event of plasmid loss. The second device, alp7, comes from the *B. subtilis* plasmid pLS20 and produces filaments that dynamically push plasmids to the poles, ensuring equal segregation during cell division[9]. To measure the performance of our maintenance systems, we used a combination of in vitro and in vivo assays. First, we performed colony counts (+/−S-Gal) after successive subcultures, and observed virtually complete plasmid maintenance (FIG. 9C) and preserved enzymatic activity of lacZ (FIG. 9D) for at least 48 hours when the circuits included both hok/sok and alp7. Since the tumor microenvironment is characterized by low nutrient levels, pH, and oxygen content[10,11] we performed further in vitro experiments under related conditions to test the performance of our diagnostic (FIG. 9F,G). We observed that PROP-Z function was generally maintained with respect to bacterial growth and lacZ function, in that both measures were mildly reduced, proportional to the extent of the condition tested.

Figure 9H:
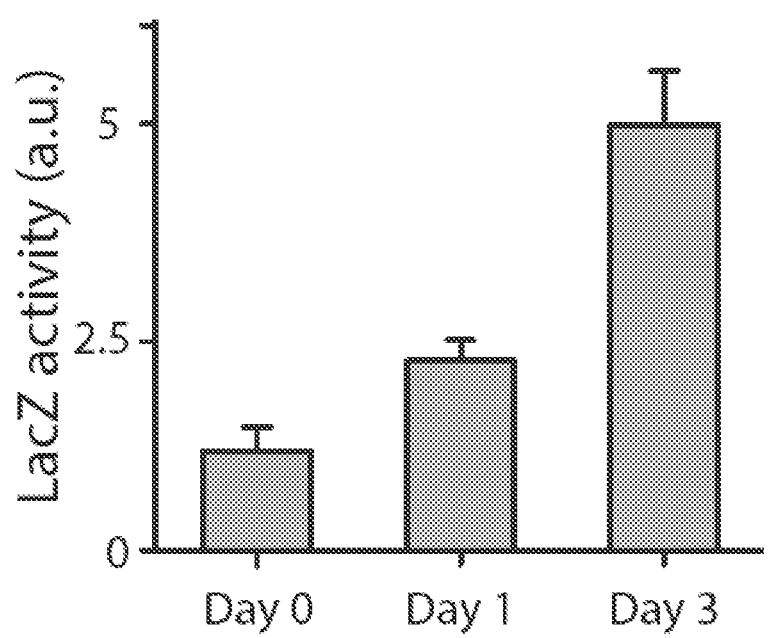

Since complex selective pressures such as those mediated by an intact immune system cannot be modeled in vitro, we performed further diagnostic testing in vivo using our subcutaneous cancer model. We found that less than 10% of bacteria remained in the tumors after 24 hours if no stabilization circuits were utilized (FIG. 9E). With the addition of the hok/sok system, 75% of the bacteria were retained for the first 24 hours, followed by a decline to 45% of the initial bacterial load after 72 hours (FIG. 9E). With the combination of hok and alp7, over 96% PROP-Z bacteria remained after 72 hours in vivo (FIG. 9E). This substantial improvement in stability likely results from the combination of pre- and post-division mechanisms that promote plasmid maintenance, mirroring natural strategies used to achieve this outcome[12]. The fully stabilized, high-copy expression vector may also be relevant for additional applications of synthetic biology in vivo. A notable advantage of our PROP-Z platform is its capacity for enhancing the signal to noise ratio via three modes of signal amplification—bacterial growth, enzyme production, and enzymatic turnover. While traditional diagnostics are limited by the small fraction of the injected dose that reaches the site of interest[13], the small number of PROP-Z bacteria that initially reach the tumor quickly expand to achieve a maximized signal. In addition, enzymatic turnover further multiplies signal gain since each enzyme can cleave many substrates. To quantify the degree of amplification achieved by our diagnostic, we excised and homogenized colonized subcutaneous tumors over the course of 3 days, performing colorimetric assays for lacZ activity at each time point. After subtracting background due to nonspecific cleavage, the combined signal amplification of bacterial exponential growth and enzymatic turnover produced signals nearly 5-fold greater than the initial injected dose (FIG. 9H). The multiple modes of amplification help generate signals that rise above the in vivo background, a significant challenge in point-of-care diagnostics[14].

Figure 10A:
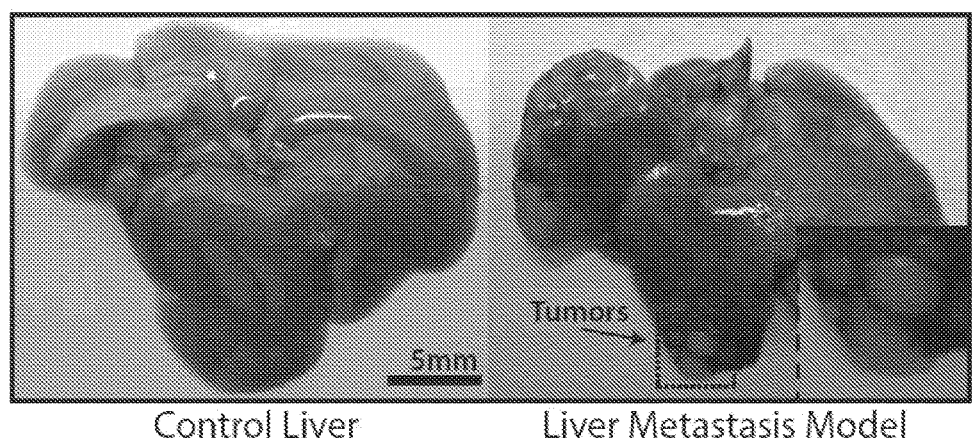
FIG. 10 depicts liver models of metastasis used to test the performance of the diagnostic on the early detection of small tumors difficult to detect using traditional methods. (10A) Healthy (left) and metastatic livers (right), showing small tumor nodules. (10B) 24 hours following oral administration, PROP-Z bacteria were detected in tumor nodules via IVIS measurement. (10C) PROP-Z bacteria colonize the inner core of metastatic nodules are often not visible from the exterior (left) but are revealed by cutting to the interior (right). Dashed line (left) indicates cut site. (10D) To determine safety and specificity, we colony counted PROP-Z in organs following oral administration. We observed $10^6$ bacteria colonize tumors after 24 hours with zero colonization (0 CFU/g) in off-target organs and no growth over time (means+−s.e.m, n=4 each). (10E) PROP-Z bacteria detect the presence of metastatic tumors via tumor specific growth leading to high-level expression of lacZ. We quantified enzymatic activity by injecting Lu-gal, a lacZ substrate that when cleaved produces luciferin, and assayed the urine for luminescence (means+−s.e.m, n=6 for each condition, 2 tail students t-test, $p<0.05$).
Figure 10B:
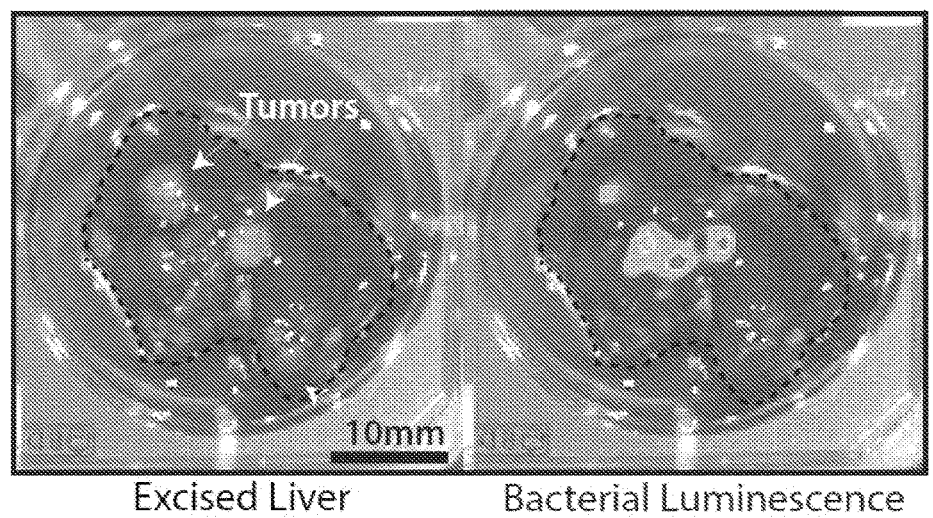
Figure 10C:
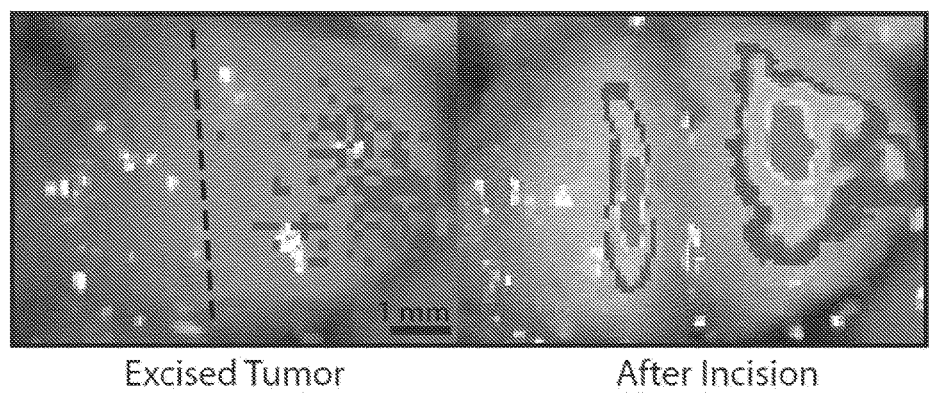
Figure 10D:
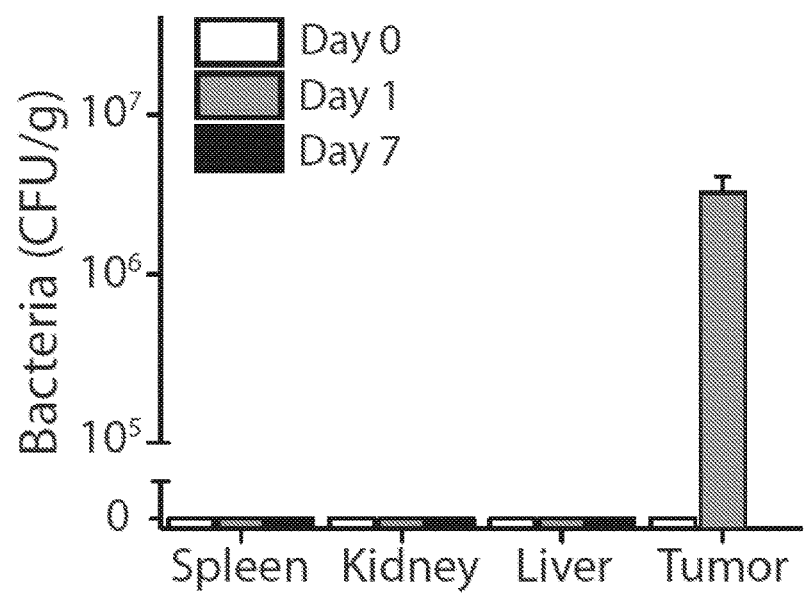
Figure 10E:
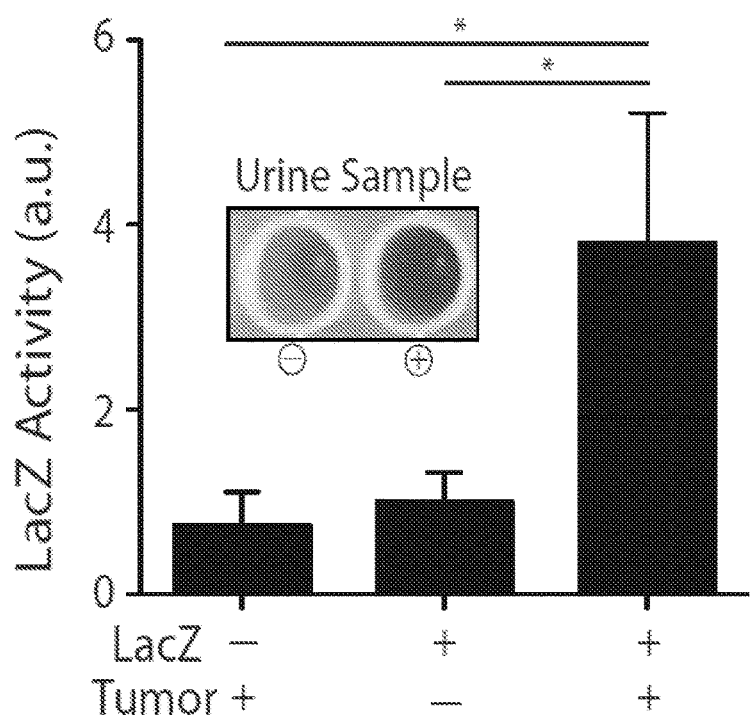
Figure 11A:
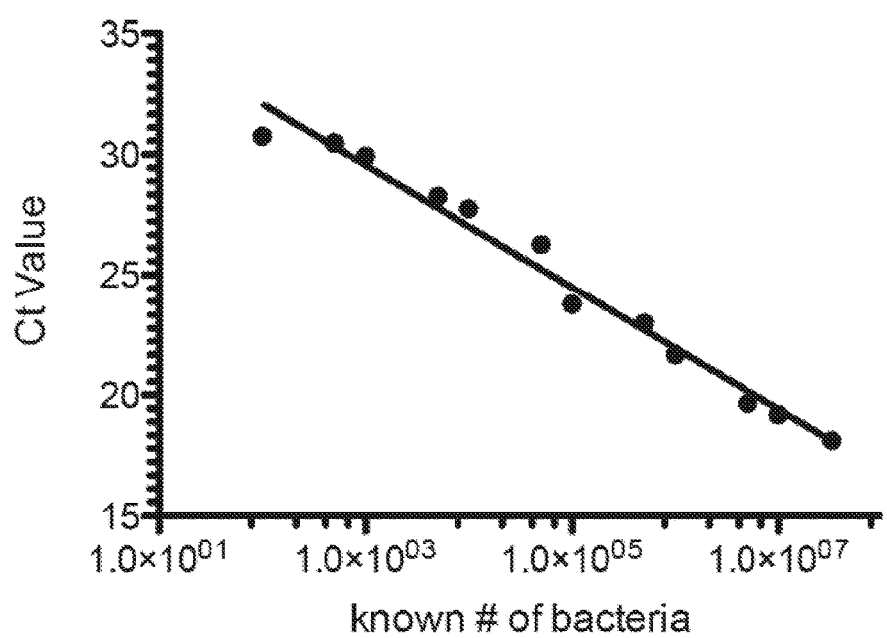
FIG. 11 depicts a qPCR calculation of the number of bacteria present in the tumor sample. (11A) *E. coli* Nissle DNA samples were DNA samples were diluted in DNA-free water and DNA was purified as above. Automated Ct values generated from a Bio-RAD iCycler machine showing a linear correlation with Ct value across several orders of magnitude. (11B) The number of bacteria were calculated using a semilog regression fit and the calculated # of bacteria is plotted in b, showing a sensitivity of detection of around ~100 bacteria per sample. Samples were repeated in quadruplicate, standard error shown is smaller than the points.
Figure 11B:
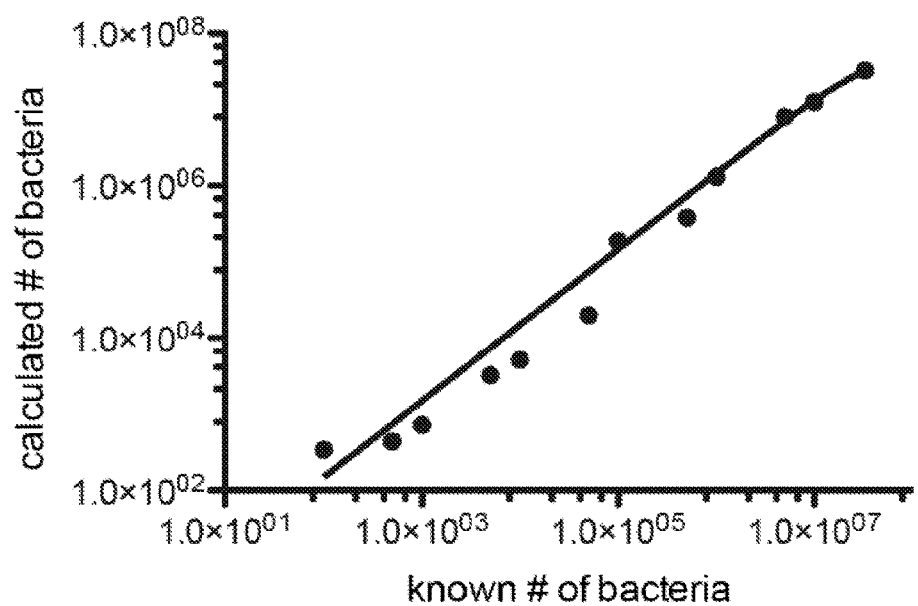
Figure 12:
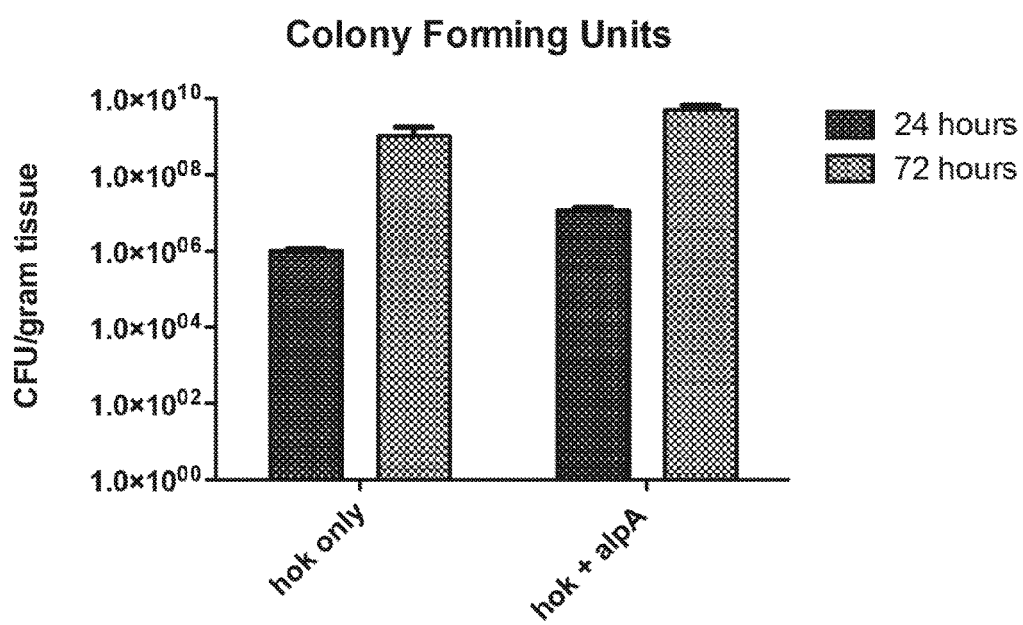
FIG. 12 depicts colony forming units with hok and hok+alpA stability systems. The absolute levels of bacteria in tumors in our athymic colorectal cancer model were measured using colony-counting methods. The growth rates of both strains appear similar, suggesting that the stability of the combined system is not due to slower growth (in fact it grows slightly faster and thus stability results would likely be underestimated).
Figure 13A:
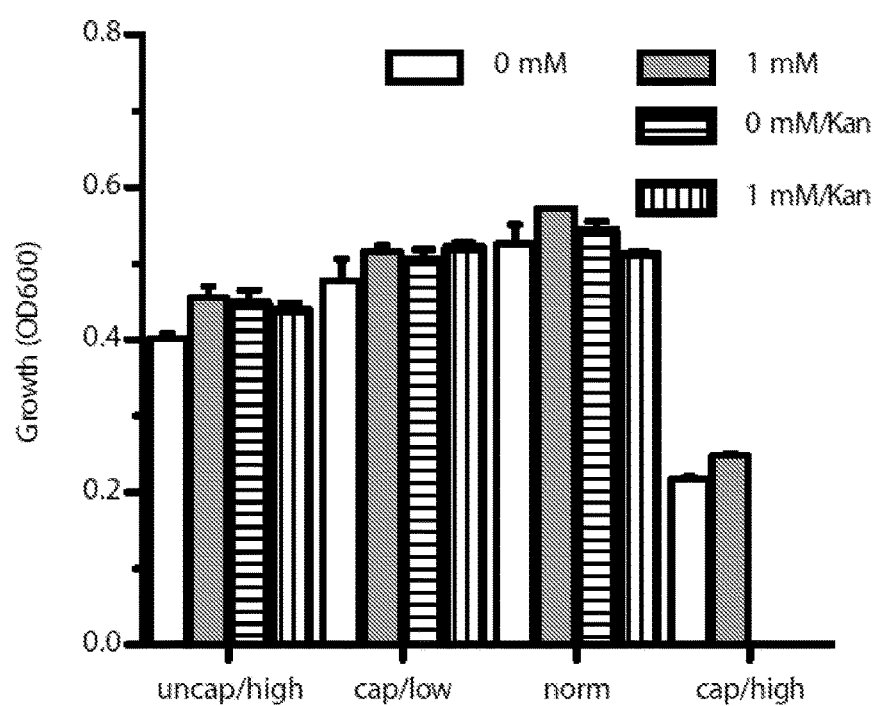
FIG. 13 depicts growth and activity of N-ColoniZe platform in different oxygen, inducer, and antibiotic conditions. (13A) $OD_{600}$ values are shown in varying oxygen conditions after 48 hours of growth (subcultured at 24 hours) in 14 mL Falcon tubes capped or uncapped with high level of media (14 mL) or low level of media (3 mL). (13B) Measured lacZ activity values in the same conditions. Norm indicates EZ-Rich media with 0.2% glucose, 3 mL of media, and uncapped. Kanamycin growth conditions for the cap/high case were not tested in either panel.
Figure 13B:
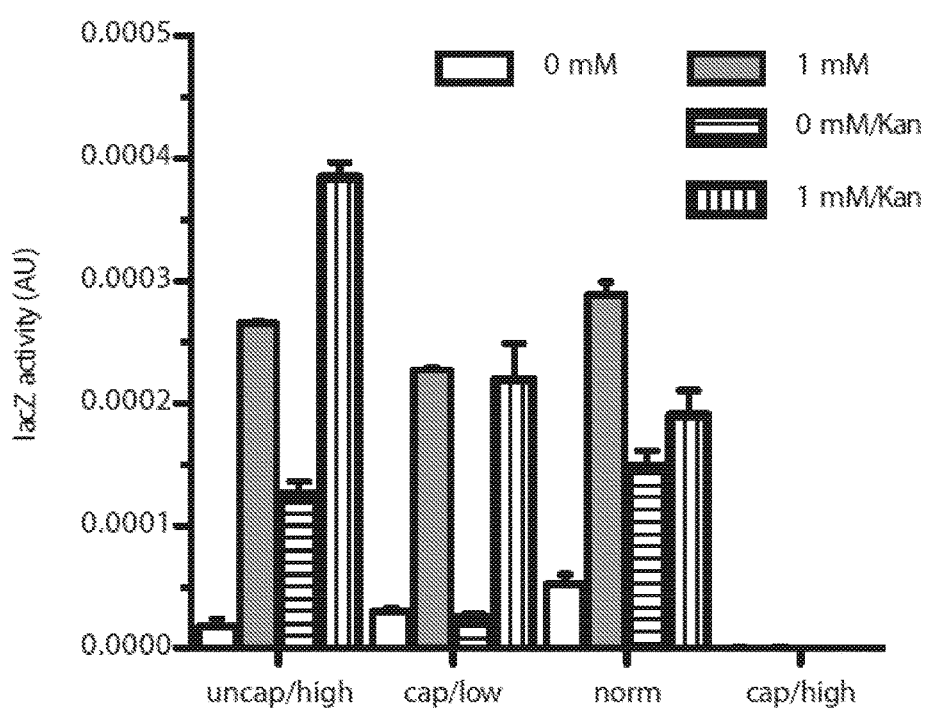

We next sought to apply PROP-Z probiotics in a preclinical assay to measure its capacity to overcome the clinical challenge of detecting cancer metastases, which are ultimately responsible for 90% of all cancer-related deaths but remain difficult to detect because of their small size and multiplicity[15]. The portal venous system flows from the GI tract to the liver, thus, we hypothesized that after oral administration, probiotics would follow blood flow patterns and directly colonize liver metastases. To test this prediction, we chose a syngeneic model of colorectal cancer liver metastases (FIG. 10A). To directly visualize probiotics within the liver metastases, we orally administered PROP-Z bacteria expressing a chromosomally-integrated luminescence cassette[16]. These small doses of bacterial were sufficient to detect luminescent signals in metastases as small as 1 mm, and we observed bacterial infiltration in virtually all tumor cores (FIG. 10B,C). To quantify the specificity of colonization, we developed a quantitative PCR-based assay to measure PROP-Z bacteria in various organs following oral administration. Over a period of 7 days, we measured the number of bacteria in liver metastases and found a striking colonization level of $10^6$ bacteria (FIG. 10D). In stark contrast, PROP-Z bacteria infiltration in control organs (spleen and kidneys) was below the limits of detection for our q-PCR assay (<500 bacteria/g). As confirmation of this negative result, we assayed for off-target colonization by performing colony counts of entire organs, and observed zero PROP-Z bacteria in any control organ tested. As a result of zero off-target colonization, PROP-Z treated mice survived without any noticeable adverse effects for at least 9 months. Collectively, these findings constitute the first demonstration of GI translocation and specific colonization of liver metastases by oral delivery of the probiotic EcN, setting the stage for chaperoned delivery of gene circuits to systemic tumors via oral delivery.

What is claimed is:

1. A composition comprising a non-pathogenic microorganism comprising: a first nucleic acid sequence encoding an enzyme, wherein the first nucleic acid sequence comprises a nucleic acid sequence having at least 90% sequence identity to the nucleic acid sequence of SEQ ID NO: 8;
    a second nucleic acid sequence encoding a polarization protein, wherein the second nucleic acid sequence comprises a nucleic acid sequence having at least 90% sequence identity to a nucleic acid sequence selected from the group consisting of SEQ ID NO: 5, SEQ ID NO: 6 and SEQ ID NO: 7; and
    a third nucleic acid sequence encoding a combination of a toxin and an antidote, wherein the third nucleic acid sequence comprises a nucleic acid sequence having at least 90% sequence identity to SEQ ID NO: 4.

2. The composition of claim 1, wherein the non-pathogenic microorganism is a bacterium.

3. The composition of claim 1, wherein the non-pathogenic microorganism is a Gram-negative bacterium.

4. The composition of claim 1, wherein the non-pathogenic microorganism is *Escherichia* spp., *Firmicutes* spp., *Bacteroidetes* spp., *Lactobacillus* spp., *Bifidobacteria* spp., or *Acidopholus* spp.

5. The composition of claim 1, wherein the non-pathogenic microorganism is *E. coli* Nissle 1917 (EcN).

6. The composition of claim 1, wherein the non-pathogenic microorganism is harvested from a human or animal sample.

7. A kit comprising: (i) the non-pathogenic microorganism composition of claim 1; (ii) at least a first container comprising a rehydration solution; and, optionally, (iii) a syringe and/or needle.

8. A method of diagnosing a subject as having a tumor comprising:
    i) administering a composition of claim 1 to a subject;
    ii) administering a substrate for the enzyme to the subject;
    iii) detecting the presence or absence of a released or excited portion of the substrate in the urine of the subject.

9. The method of claim 8, wherein the presence or absence of the released or excited portion of the substrate is determined by identifying a change in the color of the urine.

10. The method of claim 8, wherein the substrate is chosen from S-Gal, Ch-Red, and LuGal.

11. The method of claim 8 further comprising allowing a period of time to elapse after step i) sufficient for colonization of the microorganism in a tumor cell, tumor tissue, or a cell associated with a hyperproliferative disorder.

12. The method of claim 8, wherein, when the substrate is SGal, the presence or absence of the released or excited portion of the substrate is determined by contacting a urine sample from the subject to iron ions.

13. The method of claim 8, wherein when the substrate is LuGal, the presence or absence of the released or excited portion of the substrate is determined by quantifying the amount of luciferin in the urine sample of the subject.

14. The method of claim 8, wherein the tumor is derived from the gastrointestinal tract or urinary system of the subject.

15. A method of quantifying the number of cancer cells in a cell sample comprising:
    i) contacting the cell sample with a composition of claim 1 to form a mixture;
    ii) exposing the mixture to a substrate for the enzyme; and
    iii) measuring the amount of a released or an excited portion of the substrate in the mixture.

16. A method of detecting a cancer cell, cancer tissue, or cell associated with a hyperproliferative disorder in a subject comprising:
    i) administering a composition of claim 1 to the subject;
    i) administering a substrate for the enzyme to the subject;
    iii) detecting the presence or absence of a released portion of the substrate.

17. The method of claim 16, wherein the composition of claim 1 is administered to the subject per os.

18. The method of claim 16, wherein the substrate is administered to the subject per intravenous injection.

19. The method of claim 16, wherein the presence or absence of the released or excited portion of the substrate is determined by quantifying the amount of released or excited portion of the substrate present in the subject at one or a plurality of sites in the subject.

20. The method of claim 16 further comprising allowing a period of time to elapse after step i) sufficient for colonization of the microorganism in a cancer cell, cancer tissue, or a cell associated with hyperproliferative disorder.

21. The method of claim 16, wherein the presence or absence of a released or excited portion of the substrate is determined by quantifying the amount of released or excited portion of the substrate present in a urine sample of the subject.

22. A food product comprising the nonpathogenic microorganism of claim 1.

23. The composition of claim 1, wherein the first nucleic acid sequence encodes beta-galactosidase and comprises the nucleic acid sequence of SEQ ID NO: 8.

24. The composition of claim 1, wherein the second nucleic acid sequence encoding a polarization protein comprises a nucleic acid sequence selected from the group consisting of SEQ ID NO: 5, SEQ ID NO: 6, and SEQ ID NO: 7.

25. The composition of claim 1, wherein the third nucleic acid sequence encoding a combination of a toxin and an antidote comprises the nucleic acid sequence of SEQ ID NO: 4.

26. The composition of claim 1, wherein:
    (a) the first nucleic acid sequence comprises a nucleic acid sequence having at least 95% sequence identity to the nucleic acid sequence of SEQ ID NO: 8;
    (b) the second nucleic acid sequence comprises a nucleic acid sequence having at least 95% sequence identity to a nucleic acid sequence selected from the group consisting of SEQ ID NO: 5, SEQ ID NO: 6, and SEQ ID NO: 7; and
    (c) the third nucleic acid sequence comprises a nucleic acid sequence having at least 95% sequence identity to the nucleic acid sequence of SEQ ID NO: 4.

\* \* \* \* \*

SEQUENCE LISTING

<160> NUMBER OF SEQ ID NOS: 18

<210> SEQ ID NO 1
<211> LENGTH: 10768
<212> TYPE: DNA
<213> ORGANISM: Artificial Sequence
<220> FEATURE:
<223> OTHER INFORMATION: pTKW-alpA plasmid sequence

<400> SEQUENCE: 1

| | | | | | |
|---|---|---|---|---|---|
| gaatactgtt | tcctgtgtga | aattgttatc | cgctcacaat | tccacacatt | atacgagccg | 60 |
| atgattaatt | gtcatatcca | gaacgggagt | gcgccttgag | cgacacgaat | tatgcagtga | 120 |
| tttacgacct | gcacagccat | accacagctt | ccgatggctg | cctgacgcca | gaagcattgg | 180 |
| tgcaccgtgc | agtcgatgat | aagctgtcaa | acatgagaat | taattctgca | ttaatgaatc | 240 |
| ggccaacgcg | cggggagagg | cggtttgcgt | attgggcgct | cttccgcttc | ctcgctcact | 300 |
| gactcgctgc | gctcggtcgt | tcggctgcgg | cgagcggtat | cagctcactc | aaaggcggta | 360 |
| atacggttat | ccacagaatc | aggggataac | gcaggaaaga | acatgtgagc | aaaaggccag | 420 |
| caaaaggcca | ggaaccgtaa | aaaggccgcg | ttgctggcgt | ttttccatag | gctccgcccc | 480 |
| cctgacgagc | atcacaaaaa | tcgacgctca | agtcagaggt | ggcgaaaccc | gacaggacta | 540 |
| taaagatacc | aggcgtttcc | ccctggaagc | tccctcgtgc | gctctcctgt | tccgaccctg | 600 |
| ccgcttaccg | gatacctgtc | cgcctttctc | ccttcgggaa | gcgtggcgct | ttctcaatgc | 660 |
| tcacgctgta | ggtatctcag | ttcggtgtag | gtcgttcgct | ccaagctggg | ctgtgtgcac | 720 |
| gaaccccccg | ttcagcccga | ccgctgcgcc | ttatccggta | actatcgtct | tgagtccaac | 780 |
| ccggtaagac | acgacttatc | gccactggca | gcagccactg | gtaacaggat | tagcagagcg | 840 |
| aggtatgtag | gcggtgctac | agagttcttg | aagtggtggc | ctaactacgg | ctacactaga | 900 |
| aggacagtat | ttggtatctg | cgctctgctg | aagccagtta | ccttcggaaa | aagagttggt | 960 |
| agctcttgat | ccggcaaaca | aaccaccgct | ggtagcggtg | gtttttttgt | ttgcaagcag | 1020 |
| cagattacgc | gcagaaaaaa | aggatctcaa | gaagatcctt | tgatcttttc | tacgggtct | 1080 |
| gacgctcagt | ggaacgaaat | cagaagaact | cgtcaagaag | gcgatagaag | gcgatgcgct | 1140 |
| gcgaatcggg | agcggcgata | ccgtaaagca | cgaggaagcg | gtcagcccat | tcgccgccaa | 1200 |
| gctcttcagc | aatatcacgg | gtagccaacg | ctatgtcctg | atagcggtcc | gccacaccca | 1260 |
| gccggccaca | gtcgatgaat | ccagaaaagc | ggccattttc | caccatgata | ttcggcaagc | 1320 |
| aggcatcgcc | atgggtcacg | acgagatcct | cgccgtcggg | catgcgcgcc | ttgagcctgg | 1380 |
| cgaacagttc | ggctggcgcg | agcccctgat | gctcttcgtc | cagatcatcc | tgatcgacaa | 1440 |
| gaccggcttc | catccgagta | cgtgctcgct | cgatgcgatg | tttcgcttgg | tggtcgaatg | 1500 |
| ggcaggtagc | cggatcaagc | gtatgcagcc | gccgcattgc | atcagccatg | atggatactt | 1560 |
| tctcggcagg | agcaaggtga | gatgacagga | gatcctgccc | cggcacttcg | cccaatagca | 1620 |
| gccagtccct | tcccgcttca | gtgacaacgt | cgagcacagc | tgcgcaagga | acgcccgtcg | 1680 |
| tggccagcca | cgatagccgc | gctgcctcgt | cctgcagttc | attcagggca | ccggacaggt | 1740 |
| cggtcttgac | aaaaagaacc | gggcgcccct | gcgctgacag | ccggaacacg | gcggcatcag | 1800 |
| agcagccgat | tgtctgttgt | gcccagtcat | agccgaatag | cctctccacc | caagcggccg | 1860 |
| gagaacctgc | gtgcaatcca | tcttgttcaa | tcataacaaa | ctcgggagg | cagcgtgatg | 1920 |
| cggcaacaat | cacacggatt | tcccgtgaac | ggtctgaatg | agcggattat | ttcagggaa | 1980 |
| agtgagtgtg | gtcagcgtgc | aggtatatgg | gctatgatgt | gcccggcgct | tgaggctttc | 2040 |

```
tgcctcatga cgtgaaggtg gtttgttgcc gtgttgtgtg gcagaaagaa gatagccccg    2100
tagtaagtta atttcatta accaccacga ggcatccta tgtctagtcc acatcaggat    2160
agcctcttac cgcgctttgc gcaaggagaa gaaggccatg aaactaccac gaagttccct    2220
tgtctggtgt gtgttgatcg tgtgtctcac actgttgata ttcacttatc tgacacgaaa    2280
atcgctgtgc gagattcgtt acagagacgg acacagggag gtggcggctt tcatggctta    2340
cgaatccggt aagtagcaac ctggaggcgg gcgcaggccc gccttttcag gactgatgct    2400
ggtctgacta ctgaagcgcc tttataaagg ggctgctggt tcgccggtag ccccttcctc    2460
cttgctgatg ttgtgtcaat acgggataat accgcgccac atagcagaac tttaaaagtg    2520
ctcatcattg gaaaacgttc ttcggggcga aaactctcaa ggatcttacc gctgttgaga    2580
tccagttcga tgtaacccac tcgtgcaccc aactgatctt cagcatcttt tactttcacc    2640
agcgtttctg ggtgagcaaa aacaggaagg caaaatgccg caaaaaggg aataagggcg    2700
acacggaaat gttgaatact catactcttc cttttcaat attattgaag catttatcag    2760
ggttattgtc tcatgagcgg atacatattt gaatgtattt agaaaaataa acaaataggg    2820
gttccgcgca catttccccg aaaagtgcca cctgacgtga ggttcttgca ggtcggaagc    2880
ataaagtgta aagcctgggg tgcctaatga gtgagctaac ttacattaat tgcgttgcgc    2940
tcactgcccg ctttccagtc gggaaacctg tcgtgccagc tgcattaatg aatcggccaa    3000
cgcgcgggga gaggcggttt gcgtattggg cgccagggtg ttttctttt caccagtga    3060
gacgggcaac agctgattgc ccttcaccgc ctggccctga gagagttgca gcaagcggtc    3120
cacgctggtt tgccccagca ggcgaaaatc ctgtttgatg gtggttaacg gcgggatata    3180
acatgagctg tcttcggtat cgtcgtatcc cactaccgag atatccgcac caacgcgcag    3240
cccggactcg gtaatggcgc gcattgcgcc cagcgccatc tgatcgttgg caaccagcat    3300
cgcagtggga acgatgccct cattcagcat ttgcatggtt tgttgaaaac cggacatggc    3360
actccagtcg ccttcccgtt ccgctatcgg ctgaatttga ttgcgagtga gatatttatg    3420
ccagccagcc agacgcagac gcgccgagac agaacttaat gggcccgcta acagcgcgat    3480
ttgctggtga cccaatgcga ccagatgctc cacgcccagt cgcgtaccgt cttcatggga    3540
gaaaataata ctgttgatgg gtgtctggtc agagacatca agaaataacg ccggaacatt    3600
agtgcaggca gcttccacag caatggcatc ctggtcatcc agcggatagt taatgatcag    3660
cccactgacg cgttgcgcga agattgtg caccgccgct ttacaggctt cgacgccgct    3720
tcgttctacc atcgacacca ccacgctggc acccagttga tcggcgcgag atttaatcgc    3780
cgcgacaatt tgcgacggcg cgtgcagggc cagactggag gtggcaacgc caatcagcaa    3840
cgactgtttg cccgccagtt gttgtgccac gcggttggga atgtaattca gctccgccat    3900
cgccgcttcc actttttccc gcgttttcgc agaaacgtgg ctggcctggt tcaccacgcg    3960
ggaaacggtc tgataagaga caccggcata ctctgcgaca tcgtataacg ttactggttt    4020
catcctgaat tgactctctt ccgggcgcta tcatgccata ccgcgaaagg ttttgcacca    4080
cctaggtcat tagcctccaa tcttatagtg aaactccgca aacttcgttt cctcaatatt    4140
gggaatactc gataactttt gttcagcttt tcataaaaa gaaattgctt taacataatt    4200
tttttaaaa aactcataat ccctgcaaa caattcaaaa taaaattta ttaaaagatc    4260
atgacttccc ttacttaaca tattaacgac atcacccata gatgcctctt gatcaaaaca    4320
aaggctatga cgatgatcca gtagaataaa ataatcaacc aggtccttat tatcttcagc    4380
ctgacttaac aattgcttta tttcagttct tttctctata gactcatgaa ccttctcctg    4440
```

```
cataatatag tcatgccatt tattcaacag attgcctaca tagggagacg gtactttttt    4500
tactttggac aacatacact tccctccagc tattcaaaaa tcaaaactag tcctaatact    4560
tatcggcatc atcaaacatt ttaaaacaca gaacatttag tacatagtgc ttaatgttca    4620
aatctcattt tgatgctctg aacccaagca tgtactgata tcatactaaa cggctcaaac    4680
acaatctata caagttttta agataggcca aagggaataa cagtatacgt tagtgaaatc    4740
ccacaggaaa aatatattaa aatactaatg ttctatcaaa cgaacaaccc ttaaaaagga    4800
acttaaaacc tctgggtttt aaggaaattc gcattttatt tagtgttttt ctcttgactt    4860
tgagaacttg aaactagcag aatagctgac tgttctagga aacagggcga atttcgattg    4920
cctatgtctg tcgcgcaaaa aataaaaacg gacagacata ggcaatcgat caggatttga    4980
aactagcgtc atagagacgt ctgaggtttc cagctctgcc ttgctatcgc caggcttttcg   5040 cctgccatga ccttttttaca tacaatgctt gtcctgtatg caacttctat ggggtttgtc   5100
tcgtgttctc tcacacggtc acactcaatt gtgtgccgct gcatagaagc ttggccatag    5160
ttgcccgcac cgtagtgcgc caagcaacct agtggtttat ccacattctc cggaccgtta    5220
atggccgtcc tcgccattca ccacaagcgc agcaaggaac gcttattgtg gtatatcccc    5280
gggtttgcgg tggacggggc aactcctgac gtcagtttat tttacacccc ttaacggcag    5340
ctgggtgaca acaaaaaac gacagaaaac cacggtttga taccctccaa acagtggttt     5400
tctgtcgtcc aaaaatagcc gaaagtgtt gacgtataca cttgttttcg gtaaaatgaa     5460
gacataactt aaacattgta agtgagggct tacaaaccaa gtgttcgatg ctgcaacatc    5520
ggacactttt tatttgtcat tctttatttg tattcaattt tgcaaatagc tcgcaaacaa    5580
aatatgtatc atcaaatcta ttaaccttgt tgtctgcaaa caacagggtt ttttgttgtt    5640
tatttagaat aactagaacc agaattcaat gccaaaactt tcacattgac ttaacttgac    5700
tttatcttac acgattttt ttttgacgta aagccccggg cctgaaatca cttttctcta     5760
ctgatttcac tgatttcatt tttattatat aatcctcaaa tagcctgtat tcactgattt    5820
taaatgtgat ttcatttttat tgactttagt gatataagat gctagtattg aggaaagtga   5880
aatcaaagga gagaataaaa atatgaatat ttctcgtatg aacgtggact ttggaaacag    5940
tatgtacatg aatttaattg atggttattt ttttgaattg cctacaaatg tagtagagat    6000
atctaaagaa gctgctgaag gaaaatttac gagtatcgtt gaagatccgg cagatttaaa    6060
ggaccggtta ttagtttcta cagttattga tgaaacagag agatattttc tagttggtga    6120
acttgctgaa ccagaagtgt taggcaacca acacatcaag aagttacata ataaagtaga    6180
gtcacatatt ccatacgtaa cattttttagc tgcaactgct tattaccaag cgctaaaagg    6240
caaacgtgaa gataatgaag ttactattga atactttcaa acaatgctac caatttggct    6300
tcttaaaaaa ttggataagt tcagtgaaat gcagaaaagg atggcatcta aatttttggg   6360
cactcaccaa gtaaaggtgc tgacattagg attagaaaaa gagcttacta taaaagtgga    6420
agatgcagcg tgcaggatcg aatctgaagt agcaagatgg gcaataaaga aaaactttga    6480
cctagaagat aaagactatg ccgaacaatt taaaaattat gacgtagttt tttgtgatttt  6540 aggtggcgga acagatgatc tagtattact accagctgga ttaaaaccgc caaaaagtcg    6600
tgattctttt gtttctaata ccgaagcacc gttttttagcg cacttagaaa aattgagaaa    6660
agaaaaactc ctagagcact tgatagcgt tagggagctt gaaaagttta tatactcaaa    6720
tattggaaaa actaagatgg aacgaagaga cgggaatacc ggtcagaaat tgatttaac    6780 tgatatcatc aaaaaatctc ttaaagaata cacagaaatc aaaatagccc aagctgaaaa    6840
```

```
tacgttccct gcaccaaaag ataaggttta caaatacctt tattttggcg gtgttggcga   6900
ggtgcttgaa gaatcaatta gtgtggttac tgaagagaga tatggccgtg atatttctga   6960
atcaaatcat atagttgctg aggatgcaag actgctcaac ttatatggcc ttgaagtttt   7020
aagccgcgct gaacaagtaa agaaacaggc aaatgaaaaa gaggcacaat caatttaggt   7080
gattagaaat ggggaaaaac aaaagaattc cactctttaa tgtccgaaca acacaaatgt   7140
ctgatgaaat gtacgatttt gttttagagc agattagtac attcagtaaa ggtaagagta   7200
agggtacctt tagagagtat gcctttcagc tcatagaaag ggacatgcaa caacagaaag   7260
aggaacagca aaatagagaa aaagatcgtc atgttcatga tgaattaatt gccatgagag   7320
aagaaatgaa aaagaatttt cgtgatttga ggaaaaaaat tgatcaggga tcgatctacg   7380
tagaacacaa acagctgat ccaaagtcag cttcaaaaac gattgaagaa ggtcagttaa   7440
tcactgaaaa aatcactgga actattgaag aagaatacga ctatgatttt taagagcctg   7500
gattaatcta ggctcttttt ttatgccatt taagggagga ttgcatgaca aactttttt   7560 agttgcaaca cagacgccct gagcaaccgg cggatttgtc ctactcagga gagcgttcac   7620
cgacaaacaa cagataaaac gaaaggccca gtctttcgac tgagcctttc gttttatttg   7680
atgcctctag cacttagact cgagcggccg cttttttgaca ccagaccaac tggtaatggt   7740
agcgaccggc gctcagctgg aattccgccg atactgacgg gctccaggag tcgtcgccac   7800
caatccccat atggaaaccg tcgatattca gccatgtgcc ttcttccgcg tgcagcagat   7860
ggcgatggct ggtttccatc agttgctgtt gactgtagcg gctgatgttg aactggaagt   7920
cgccgcgcca ctggtgtggg ccataattca attcgcgcgt cccgcagcgc agaccgtttt   7980
cgctcgggaa gacgtacggg gtatacatgt ctgacaatgg cagatcccag cggtcaaaac   8040
aggcggcagt aaggcggtcg ggatagtttt cttgcggccc taatccgagc cagtttaccc   8100
gctctgctac ctgcgccagc tggcagttca ggccaatccg cgccggatgc ggtgtatcgc   8160
tcgccacttc aacatcaacg gtaatcgcca tttgaccact accatcaatc cggtaggttt   8220
tccggctgat aaataaggtt ttcccctgat gctgccacgc gtgagcggtc gtaatcagca   8280
ccgcatcagc aagtgtatct gccgtgcact gcaacaacgc tgcttcggcc tggtaatggc   8340
ccgccgcctt ccagcgttcg acccaggcgt tagggtcaat gcgggtcgct tcacttacgc   8400
caatgtcgtt atccagcggt gcacgggtga actgatcgcg cagcggcgtc agcagttggt   8460
ttttatcgcc aatccacatc tgtgaaagag agcctgactg gcggttaaat tgccaacgct   8520
tattacccag ctcgatgcaa aaatccattt cgctggtggt cagatgcggg atggcgtggg   8580
acgcggcggg gagcgtcaca ctgaggtttt ccgccagacg ccactgctgc caggcgctga   8640
tgtgcccggc ttctgaccat gcggtcgcgt tcggttgcac tacgcgtact gtgagccaga   8700
gttgcccggc gctctccggc tgcggtagtt caggcagttc aatcaactgt ttaccttgtg   8760
gagcgacatc cagaggcact tcaccgcttg ccagcggctt accatccagc gccaccatcc   8820
agtgcaggag ctcgttatcg ctatgacgga acaggtattc gctggtcact tcgatggttt   8880
gcccggataa acgaactgg aaaaactgct gctggtgttt tgcttccgtc agcgctggat   8940
gcggcgtgcg gtcggcaaag accagaccgt tcatacagaa ctggcgatcg ttcggcgtat   9000
cgccaaaatc accgccgtaa gccgaccacg ggttgccgtt ttcatcatat ttaatcagcg   9060
actgatccac ccagtcccag acgaagccgc cctgtaaacg gggatactga cgaaacgcct   9120
gccagtattt agcgaaaccg ccaagactgt tacccatcgc gtgggcgtat cgcaaagga   9180 tcagcgggcg cgtctctcca ggtagcgaaa gccattttt gatggaccat tcggcacag   9240
```

```
ccgggaaggg ctggtcttca tccacgcgcg cgtacatcgg gcaaataata tcggtggccg      9300
tggtgtcggc tccgccgcct tcatactgca ccgggcggga aggatcgaca gatttgatcc      9360
agcgatacag cgcgtcgtga ttagcgccgt ggcctgattc attccccagc gaccagatga      9420
tcacactcgg gtgattacga tcgcgctgca ccattcgcgt tacgcgttcg ctcatcgccg      9480
gtagccagcg cggatcatcg gtcagacgat tcattggcac catgccgtgg gtttcaatat      9540
tggcttcatc caccacatac aggccgtagc ggtcgcacag cgtgtaccac agcggatggt      9600
tcggataatg cgaacagcgc acggcgttaa agttgttctg cttcatcagc aggatatcct      9660
gcaccatcgt ctgctcatcc atgacctgac catgcagagg atgatgctcg tgacggttaa      9720
cgcctcgaat cagcaacggc ttgccgttca gcagcagcag accattttca atccgcacct      9780
cgcggaaacc gacatcgcag gcttctgctt caatcagcgt gccgtcggcg gtgtgcagtt      9840
caaccaccgc acgatagaga ttcgggattt cggcgctcca cagtttcggg ttttcgacgt      9900
tcagacgtag tgtgacgcga tcggcataac caccacgctc atcgataatt tcaccgccga      9960
aaggcgcggt gccgctggcg acctgcgttt caccctgcca taaagaaact gttacccgta     10020
ggtagtcacg caactcgccg cacatctgaa cttcagcctc cagtacagcg cggctgaaat     10080
catcattaaa gcgagtggca acatggaaat cgctgatttg tgtagtcggt ttatgcagca     10140
acgagacgtc acggaaaatg ccgctcatcc gccacatatc ctgatcttcc agataactgc     10200
cgtcactcca gcgcagcacc atccgcgca ggcggttttc tccggcgcgt aaaaatgcgc      10260
tcaggtcaaa ttcagacggc aaacgactgt cctggccgta accgacccag cgcccgttgc     10320
accacagatg aaacgccgag ttaacgccat caaaaataat tcgcgtctgg ccttcctgta     10380
gccagctttc atcaacatta aatgtgagcg agtaacaacc cgtcggattc tccgtgggaa     10440
caaacggcgg attgaccgta atgggatagg tcacgttggt gtagatgggc gcatcgtaac     10500
cgtgcatctg ccagtttgag gggacgacga cagtatcggc ctcaggaaga tcgcactcca     10560
gccagctttc cggcaccgct tctggtgccg gaaaccaggc aaagcgccat cgccattca      10620 ggctgcgcaa ctgttgggaa gggcgatcgg tgcgggcctc ttcgctatta cgccagctgg     10680 cgaaagggg atgtgctgca aggcgattaa gttgggtaac gccagggttt tcccagtcac      10740
gacgttgtaa aacgacggga tctatcat                                         10768
```

<210> SEQ ID NO 2
<211> LENGTH: 783
<212> TYPE: DNA
<213> ORGANISM: Artificial Sequence
<220> FEATURE:
<223> OTHER INFORMATION: colE1 sequence plasmid component

<400> SEQUENCE: 2

```
gcgttcggct gcggcgagcg gtatcagctc actcaaaggc ggtaatacgg ttatccacag        60
aatcagggga taacgcagga agaacatgt gagcaaaagg ccagcaaaag gccaggaacc       120
gtaaaaaggc cgcgttgctg gcgtttttcc ataggctccg ccccctgac gagcatcaca       180 aaaatcgacg ctcaagtcag aggtggcgaa acccgacagg actataaaga taccaggcgt       240
ttccccctgg aagctccctc gtgcgctctc ctgttccgac cctgccgctt accggatacc       300
tgtccgcctt tctcccttcg ggaagcgtgg cgctttctca tagctcacgc tgtaggtatc       360
tcagttcggt gtaggtcgtt cgctccaagc tgggctgtgt gcacgaaccc cccgttcagc       420
ccgaccgctg cgccttatcc ggtaactatc gtcttgagtc aacccggta agacacgact       480
```

```
tatcgccact ggcagcagcc actggtaaca ggattagcag agcgaggtat gtaggcggtg    540
ctacagagtt cttgaagtgg tggcctaact acggctacac tagaaggaca gtatttggta    600
tctgcgctct gctgaagcca gttaccttcg aaaaagagt tggtagctct tgatccggca     660
aacaaaccac cgctggtagc ggtggttttt tgtttgcaa gcagcagatt acgcgcagaa     720
aaaaaggatc tcaagaagat cctttgatct tttctacggg gtctgacgct cagtggaacg    780
aaa                                                                  783

<210> SEQ ID NO 3
<211> LENGTH: 792
<212> TYPE: DNA
<213> ORGANISM: Artificial Sequence
<220> FEATURE:
<223> OTHER INFORMATION: KanR sequence plasmid component

<400> SEQUENCE: 3
gaagaactcg tcaagaaggc gatagaaggc gatgcgctgc gaatcgggag cggcgatacc     60
gtaaagcacg aggaagcggt cagcccattc gccgccaagc tcttcagcaa tatcacgggt    120
agccaacgct atgtcctgat agcggtccgc cacacccagc cggccacagt cgatgaatcc    180
agaaaagcgg ccattttcca ccatgatatt cggcaagcag gcatcgccat gggtcacgac    240
gagatcctcg ccgtcgggca tgcgcgcctt gagcctggcg aacagttcgg ctggcgcgag    300
cccctgatgc tcttcgtcca gatcatcctg atcgacaaga ccggcttcca tccgagtacg    360
tgctcgctcg atgcgatgtt tcgcttggtg gtcgaatggg caggtagccg gatcaagcgt    420
atgcagccgc cgcattgcat cagccatgat ggatactttc tcggcaggag caaggtgaga    480
tgacaggaga tcctgccccg gcacttcgcc caatagcagc cagtcccttc ccgcttcagt    540
gacaacgtcg agcacagctg cgcaaggaac gcccgtcgtg gccagccacg atagccgcgc    600
tgcctcgtcc tgcagttcat tcagggcacc ggacaggtcg gtcttgacaa aaagaaccgg    660
gcgcccctgc gctgacagcc ggaacacggc ggcatcagag cagccgattg tctgttgtgc    720
ccagtcatag ccgaatagcc tctccaccca gcggccgga gaacctgcgt gcaatccatc     780
ttgttcaatc at                                                        792

<210> SEQ ID NO 4
<211> LENGTH: 580
<212> TYPE: DNA
<213> ORGANISM: Escherichia coli

<400> SEQUENCE: 4
aacaaactcc gggaggcagc gtgatgcggc aacaatcaca cggatttccc gtgaacggtc     60
tgaatgagcg gattattttc agggaaagtg agtgtggtca gcgtgcaggt atatgggcta    120
tgatgtgccc ggcgcttgag gctttctgcc tcatgacgtg aaggtggttt gttgccgtgt    180
tgtgtggcag aaagaagata gccccgtagt aagttaattt tcattaacca ccacgaggca    240
tccctatgtc tagtccacat caggatagcc tcttaccgcg ctttgcgcaa ggagaagaag    300
gccatgaaac taccacgaag ttcccttgtc tggtgtgtgt tgatcgtgtg tctcacactg    360
ttgatattca cttatctgac acgaaaatcg ctgtgcgaga ttcgttacag agacggacac    420
agggaggtgg cggctttcat ggcttacgaa tccggtaagt agcaacctgg aggcgggcgc    480
aggcccgcct tttcaggact gatgctggtc tgactactga agcgccttta taagggggct    540
gctggttcgc cggtagcccc tttctccttg ctgatgttgt                          580
```

<210> SEQ ID NO 5
<211> LENGTH: 3501
<212> TYPE: DNA
<213> ORGANISM: Artificial Sequence
<220> FEATURE:
<223> OTHER INFORMATION: alp7 plasmid component with A and R

<400> SEQUENCE: 5

```
tcattagcct ccaatcttat agtgaaactc cgcaaacttc gtttcctcaa tattgggaat      60
actcgataac ttttgttcag cttttttcata aaagaaatt gctttaacat aattttttt     120
aaaaaactca taatcccctg caaacaattc aaaataaaaa tttattaaaa gatcatgact    180
tcccttactt aacatattaa cgacatcacc catagatgcc tcttgatcaa aacaaaggct    240
atgacgatga tccagtagaa taaaataatc aaccaggtcc ttattatctt cagcctgact    300
taacaattgc tttatttcag ttcttttctc tatagactca tgaaccttct cctgcataat    360
atagtcatgc catttattca acagattgcc tacataggga gacggtactt ttttttacttt   420
ggacaacata cacttccctc cagctattca aaaatcaaaa ctagtcctaa tacttatcgg    480
catcatcaaa cattttaaaa cacagaacat ttagtacata gtgcttaatg ttcaaatctc    540
attttgatgc tctgaaccca agcatgtact gatatcatac taaacggctc aaacacaatc    600
tatacaagtt tttaagatag gccaaaggga ataacagtat acgttagtga atcccacag     660
gaaaatata ttaaaatact aatgttctat caaacgaaca acccttaaaa aggaacttaa     720
aacctctggg ttttaaggaa attcgcattt tatttagtgt ttttctcttg actttgagaa    780
cttgaaacta gcagaatagc tgactgttct aggaaacagg gcgaatttcg attgcctatg    840
tctgtcgcgc aaaaaataaa aacggacaga cataggcaat cgatcaggat ttgaaactag    900
cgtcatagag acgtctgagg tttccagctc tgccttgcta cgccaggct ttcgcctgcc     960
atgacctttt tacatacaat gcttgtcctg tatgcaactt ctatggggtt tgtctcgtgt   1020
tctctcacac ggtcacactc aattgtgtgc cgctgcatag aagcttggcc atagttgccc   1080
gcaccgtagt gcgccaagca acctagtggt ttatccacat tctccggacc gttaatggcc   1140
gtcctcgcca ttcaccacaa gcgcagcaag gaacgcttat tgtggtatat ccccgggttt   1200
gcggtggacg gggcaactcc tgacgtcagt ttattttaca cccctaaacg gcagctgggt   1260
gacaaacaaa aaacgacaga aaaccacggt ttgataccct ccaaacagtg gttttctgtc   1320
gtccaaaaat agccgaaaag tgttgacgta tacacttgtt ttcggtaaaa tgaagacata   1380
acttaaacat tgtaagtgag ggcttacaaa ccaagtgttc gatgctgcaa catcggacac   1440
tttttatttg tcattcttta tttgtattca attttgcaaa tagctcgcaa acaaaatatg   1500
tatcatcaaa tctattaacc ttgttgtctg caaacaacag ggtttttgt tgtttattta    1560
gaataactag aaccagaatt caatgccaaa actttcacat tgacttaact tgactttatc   1620
ttacacgatt tttttttga cgtaaagccc cgggcctgaa atcacttttc tctactgatt    1680
tcactgattt catttttatt atataatcct caaatagcct gtattcactg attttaaatg   1740
tgatttcatt ttattgactt tagtgatata agatgctagt attgaggaaa gtgaaatcaa   1800
aggagagaat aaaaatatga atatttctcg tatgaacgtg gactttggaa acagtatgta   1860
catgaattta attgatggtt attttttga attgcctaca aatgtagtag agatatctaa    1920
agaagctgct gaaggaaaat ttacgagtat cgttgaagat ccggcagatt taaaggaccg   1980
gttattagtt tctacagtta ttgatgaaac agagagatat tttctagttg gtgaacttgc   2040
tgaaccagaa gtgttaggca accaacacat caagaagtta cataataaag tagagtcaca   2100
```

```
tattccatac gtaacatttt tagctgcaac tgcttattac caagcgctaa aaggcaaacg    2160
tgaagataat gaagttacta ttgaatactt tcaaacaatg ctaccaattt ggcttcttaa    2220
aaaattggat aagttcagtg aaatgcagaa aaggatggca tctaaatttt tgggcactca    2280
ccaagtaaag gtgctgacat taggattaga aaaagagctt actataaaag tggaagatgc    2340
agcgtgcagg atcgaatctg aagtagcaag atgggcaata agaaaaact tgacctaga     2400 agataaagac tatgccgaac aatttaaaaa ttatgacgta gttttttgtg atttaggtgg    2460
cggaacagat gatctagtat tactaccagc tggattaaaa ccgccaaaaa gtcgtgattc    2520 tttttgtttct aataccgaag caccgttttt agcgcactta gaaaaattga aaaagaaaa    2580 actcctagag cactttgata gcgttaggga gcttgaaaag tttatatact caaatattgg    2640
aaaaactaag atggaacgaa gagacgggaa taccggtcag aaatttgatt taactgatat    2700
catcaaaaaa tctcttaaag aatacacaga atcaaaata gcccaagctg aaaatacgtt    2760
ccctgcacca aaagataagg tttacaaata cctttatttt ggcggtgttg gcgaggtgct    2820
tgaagaatca attagtgtgg ttactgaaga gagatatggc cgtgatatt ctgaatcaaa     2880 tcatatagtt gctgaggatg caagactgct caacttatat ggccttgaag tttttaagccg   2940 cgctgaacaa gtaaagaaac aggcaaatga aaaagaggca caatcaattt aggtgattag    3000
aaatggggaa aaacaaaaga attccactct ttaatgtccg aacaacacaa atgtctgatg    3060
aaatgtcgca ttttgttta gagcagatta gtacattcag taaaggtaag agtaagggta     3120
cctttagaga gtatgccttt cagctcatag aaagggacat gcaacaacag aaagaggaac    3180
agcaaaatag agaaaagat cgtcatgttc atgatgaatt aattgccatg agagaagaaa     3240
tgaaaaaaga atttcgtgat ttgaggaaaa aaattgatca gggatcgatc tacgtagaac    3300 acaaacagc tgatccaaag tcagcttcaa aaacgattga agaaggtcag ttaatcactg     3360
aaaaaatcac tggaactatt gaagaagaat acgactatga ttttttaagag cctggattaa   3420 tctaggctct ttttttatgc catttaaggg aggattgcat gacaaacttt ttttagttgc    3480
aacacagacg ccctgagcaa c                                              3501

<210> SEQ ID NO 6
<211> LENGTH: 1176
<212> TYPE: DNA
<213> ORGANISM: Artificial Sequence
<220> FEATURE:
<223> OTHER INFORMATION: Alp7A plasmid component

<400> SEQUENCE: 6
atgaatattt ctcgtatgaa cgtggacttt ggaaacagta tgtacatgaa tttaattgat      60
ggttattttt ttgaattgcc tacaaatgta gtagagatat ctaaagaagc tgctgaagga    120
aaatttacga gtatcgttga agatccggca gatttaaagg accggttatt agtttctaca    180
gttattgatg aaacagagag atattttcta gttggtgaac ttgctgaacc agaagtgtta    240
ggcaaccaac acatcaagaa gttacataat aaagtagagt cacatattcc atacgtaaca    300 ttttttagctg caactgctta ttaccaagcg ctaaaaggca aacgtgaaga taatgaagtt    360
actattgaat actttcaaac aatgctacca atttggcttc ttaaaaaatt ggataagttc    420
agtgaaatgc agaaaaggat ggcatctaaa ttttttgggca ctcaccaagt aaaggtgctg    480
acattaggat tagaaaaaga gcttactata aaagtggaag atgcagcgtg caggatcgaa    540
tctgaagtag caagatgggc aataaagaaa aactttgacc tagaagataa agactatgcc    600
gaacaattta aaaattatga cgtagttttt tgtgatttag gtggcggaac agatgatcta    660
```

| | |
|---|---|
| gtattactac cagctggatt aaaaccgcca aaaagtcgtg attcttttgt ttctaatacc | 720 |
| gaagcaccgt ttttagcgca cttagaaaaa ttgagaaaag aaaaactcct agagcacttt | 780 |
| gatagcgtta gggagcttga aaagtttata tactcaaata ttggaaaaac taagatggaa | 840 |
| cgaagagacg ggaataccgg tcagaaattt gatttaactg atatcatcaa aaatctctt | 900 |
| aaagaataca cagaaatcaa aatagcccaa gctgaaaata cgttccctgc accaaaagat | 960 |
| aaggtttaca aataccttta ttttggcggt gttggcgagg tgcttgaaga atcaattagt | 1020 |
| gtggttactg aagagagata tggccgtgat atttctgaat caaatcatat agttgctgag | 1080 |
| gatgcaagac tgctcaactt atatggcctt gaagttttaa ccgcgctga acaagtaaag | 1140 |
| aaacaggcaa atgaaaaaga ggcacaatca atttag | 1176 |

<210> SEQ ID NO 7
<211> LENGTH: 407
<212> TYPE: DNA
<213> ORGANISM: Artificial Sequence
<220> FEATURE:
<223> OTHER INFORMATION: Alp7R

<400> SEQUENCE: 7

| | |
|---|---|
| atggggaaaa acaaaagaat tccactcttt aatgtccgaa caacacaaat gtctgatgaa | 60 |
| atgtacgatt ttgttttaga gcagattagt acattcagta aaggtaagag taagggtacc | 120 |
| tttagagagt atgcctttca gctcatagaa agggacatgc aacaacagaa agaggaacag | 180 |
| caaaatagag aaaaagatcg tcatgttcat gatgaattaa ttgccatgag agaagaaatg | 240 |
| aaaaaagaat tcgtgatttt gaggaaaaaa attgatcagg gatcgatcta cgtagaacac | 300 |
| aaaacagctg atccaaagtc agcttcaaaa acgattgaag aaggtcagtt aatcactgaa | 360 |
| aaaatcactg gaactattga agaagaatac gactatgatt tttaaga | 407 |

<210> SEQ ID NO 8
<211> LENGTH: 3075
<212> TYPE: DNA
<213> ORGANISM: Escherichia coli

<400> SEQUENCE: 8

| | |
|---|---|
| atgatagatc ccgtcgtttt acaacgtcgt gactgggaaa accctggcgt tacccaactt | 60 |
| aatcgccttg cagcacatcc ccctttcgcc agctggcgta atagcgaaga ggcccgcacc | 120 |
| gatcgccctt cccaacagtt gcgcagcctg aatggcgaat ggcgctttgc ctggtttccg | 180 |
| gcaccagaag cggtgccgga aagctggctg gagtgcgatc ttcctgaggc cgatactgtc | 240 |
| gtcgtcccct caaactggca gatgcacggt tacgatgcgc ccatctacac caacgtgacc | 300 |
| tatcccatta cggtcaatcc gccgtttgtt cccacggaga tccgacgggt tgttactcg | 360 |
| ctcacattta tgttgatga aagctggcta caggaaggcc agacgcgaat tatttttgat | 420 |
| ggcgttaact cggcgtttca tctgtggtgc aacgggcgct gggtcggtta cggccaggac | 480 |
| agtcgtttgc cgtctgaatt tgacctgagc gcatttttac gcgccggaga aaaccgcctc | 540 |
| gcggtgatgg tgctgcgctg gagtgacggc agttatctgg aagatcagga tatgtggcgg | 600 |
| atgagcggca ttttccgtga cgtctcgttg ctgcataaac cgactacaca aatcagcgat | 660 |
| ttccatgttg ccactcgctt taatgatgat ttcagccgcg ctgtactgga ggctgaagtt | 720 |
| cagatgtgcg gcgagttgcg tgactaccta cgggtaacag tttctttatg cagggtgaa | 780 |
| acgcaggtcg ccagcggcac cgcgcctttc ggcggtgaaa ttatcgatga gcgtggtggt | 840 |
| tatgccgatc gcgtcacact acgtctgaac gtcgaaaacc cgaaactgtg gagcgccgaa | 900 |

| | | |
|---|---|---|
| atcccgaatc tctatcgtgc ggtggttgaa ctgcacaccg ccgacggcac gctgattgaa | 960 |
| gcagaagcct gcgatgtcgg tttccgcgag gtgcggattg aaaatggtct gctgctgctg | 1020 |
| aacggcaagc cgttgctgat tcgaggcgtt aaccgtcacg agcatcatcc tctgcatggt | 1080 |
| caggtcatgg atgagcagac gatggtgcag gatatcctgc tgatgaagca gaacaacttt | 1140 |
| aacgccgtgc gctgttcgca ttatccgaac catccgctgt ggtacacgct gtgcgaccgc | 1200 |
| tacggcctgt atgtggtgga tgaagccaat attgaaaccc acggcatggt gccaatgaat | 1260 |
| cgtctgaccg atgatccgcg ctggctaccg gcgatgagcg aacgcgtaac gcgaatggtg | 1320 |
| cagcgcgatc gtaatcaccc gagtgtgatc atctggtcgc tggggaatga atcaggccac | 1380 |
| ggcgctaatc acgacgcgct gtatcgctgg atcaaatctg tcgatccttc ccgcccggtg | 1440 |
| cagtatgaag gcggcggagc cgacaccacg gccaccgata ttatttgccc gatgtacgcg | 1500 |
| cgcgtggatg aagaccagcc cttcccggct gtgccgaaat ggtccatcaa aaaatggctt | 1560 |
| tcgctacctg gagagacgcg cccgctgatc ctttgcgaat acgcccacgc gatgggtaac | 1620 |
| agtcttggcg gtttcgctaa atactggcag gcgtttcgtc agtatccccg tttacagggc | 1680 |
| ggcttcgtct gggactgggt ggatcagtcg ctgattaaat atgatgaaaa cggcaacccg | 1740 |
| tggtcggctt acgcggtga ttttggcgat acgccgaacg atcgccagtt ctgtatgaac | 1800 |
| ggtctggtct ttgccgaccg cacgccgcat ccagcgctga cggaagcaaa acaccagcag | 1860 |
| cagttttttcc agttccgttt atccgggcaa accatcgaag tgaccagcga atacctgttc | 1920 |
| cgtcatagcg ataacgagct cctgcactgg atggtggcgc tggatggtaa gccgctggca | 1980 |
| agcggtgaag tgcctctgga tgtcgctcca caaggtaaac agttgattga actgcctgaa | 2040 |
| ctaccgcagc cggagagcgc cgggcaactc tggctcacag tacgcgtagt gcaaccgaac | 2100 |
| gcgaccgcat ggtcagaagc cgggcacatc agcgcctggc agcagtggcg tctggcggaa | 2160 |
| aacctcagtg tgacgctccc cgccgcgtcc cacgccatcc gcatctgac caccagcgaa | 2220 |
| atggattttt gcatcgagct gggtaataag cgttggcaat taaccgcca gtcaggctct | 2280 |
| ctttcacaga tgtggattgg cgataaaaac caactgctga cgccgctgcg cgatcagttc | 2340 |
| acccgtgcac cgctggataa cgacattggc gtaagtgaag cgacccgcat tgaccctaac | 2400 |
| gcctgggtcg aacgctggaa ggcggcgggc cattaccagg ccgaagcagc gttgttgcag | 2460 |
| tgcacggcag atacttgc tgatgcgtg ctgattacga ccgctcacgc gtggcagcat | 2520 |
| caggggaaaa ccttatttat cagccggaaa acctaccgga ttgatggtag tggtcaaatg | 2580 |
| gcgattaccg ttgatgttga agtggcgagc gatacaccgc atccggcgcg gattggcctg | 2640 |
| aactgccagc tggcgcaggt agcagagcgg gtaaactggc tcggattagg gccgcaagaa | 2700 |
| aactatcccg accgcttac tgccgcctgt tttgaccgct gggatctgcc attgtcagac | 2760 |
| atgtataccc cgtacgtctt cccgagcgaa aacggtctgc gctgcgggac gcgcgaattg | 2820 |
| aattatggcc cacaccagtg gcgcggcgac ttccagttca acatcagccg ctacagtcaa | 2880 |
| cagcaactga tggaaaccag ccatcgccat ctgctgcacg cggaagaagg cacatggctg | 2940 |
| aatatcgacg gtttccatat ggggattggt ggcgacgact cctggagccc gtcagtatcg | 3000 |
| gcggaattcc agctgagcgc cggtcgctac cattaccagt tggtctggtg tcaaaaagcg | 3060 |
| gccgctcgag tctaa | 3075 |

<210> SEQ ID NO 9
<211> LENGTH: 106
<212> TYPE: DNA
<213> ORGANISM: Artificial Sequence

```
<220> FEATURE:
<223> OTHER INFORMATION: T1 terminator plasmid component

<400> SEQUENCE: 9
cggcggattt gtcctactca ggagagcgtt caccgacaaa caacagataa aacgaaaggc      60
ccagtctttc gactgagcct ttcgttttat ttgatgcctc tagcac                    106

<210> SEQ ID NO 10
<211> LENGTH: 1083
<212> TYPE: DNA
<213> ORGANISM: Escherichia coli

<400> SEQUENCE: 10
atgaaaccag taacgttata cgatgtcgca gagtatgccg gtgtctctta tcagaccgtt      60
tcccgcgtgg tgaaccaggc cagccacgtt tctgcgaaaa cgcgggaaaa agtggaagcg     120
gcgatggcgg agctgaatta cattcccaac gcgtggcac aacaactggc gggcaaacag     180
tcgttgctga ttggcgttgc cacctccagt ctggccctgc acgcgccgtc gcaaattgtc     240
gcggcgatta aatctcgcgc cgatcaactg ggtgccagcg tggtggtgtc gatggtagaa     300
cgaagcggcg tcgaagcctg taaagcggcg gtgcacaatc ttctcgcgca acgcgtcagt     360
gggctgatca ttaactatcc gctggatgac caggatgcca ttgctgtgga agctgcctgc     420
actaatgttc cggcgttatt tcttgatgtc tctgaccaga cacccatcaa cagtattatt     480
ttctcccatg aagacggtac gcgactgggc gtggagcatc tggtcgcatt gggtcaccag     540
caaatcgcgc tgttagcggg cccattaagt tctgtctcgg cgcgtctgcg tctggctggc     600
tggcataaat atctcactcg caatcaaatt cagccgatag cggaacggga aggcgactgg     660
agtgccatgt ccggttttca acaaaccatg caaatgctga atgagggcat cgttcccact     720
gcgatgctgg ttgccaacga tcagatggcg ctgggcgcaa tgcgcgccat taccgagtcc     780
gggctgcgcg ttggtgcgga tatctcggta gtgggatacg acgataccga agacagctca     840
tgttatatcc cgccgttaac caccatcaaa caggattttc gcctgctggg gcaaaccagc     900
gtggaccgct tgctgcaact ctctcagggc caggcggtga agggcaatca gctgttgccc     960
gtctcactgg tgaaaagaaa aaccaccctg gcgcccaata cgcaaaccgc ctctccccgc    1020
gcgttggccg attcattaat gcagctggca cgacaggttt cccgactgga aagcgggcag    1080
tga                                                                  1083

<210> SEQ ID NO 11
<211> LENGTH: 57
<212> TYPE: DNA
<213> ORGANISM: Artificial Sequence
<220> FEATURE:
<223> OTHER INFORMATION: placIq component

<400> SEQUENCE: 11
cctgaattga ctctcttccg ggcgctatca tgccataccg cgaaaggttt tgcacca             57

<210> SEQ ID NO 12
<211> LENGTH: 36
<212> TYPE: DNA
<213> ORGANISM: Artificial Sequence
<220> FEATURE:
<223> OTHER INFORMATION: primer P1

<400> SEQUENCE: 12
ccaccaccta ggtcattagc ctccaatctt atagtg                                    36
```

-continued

```
<210> SEQ ID NO 13
<211> LENGTH: 28
<212> TYPE: DNA
<213> ORGANISM: Artificial Sequence
<220> FEATURE:
<223> OTHER INFORMATION: primer P2

<400> SEQUENCE: 13
ccaccagcta gcgttgctca gggcgtct                                          28

<210> SEQ ID NO 14
<211> LENGTH: 26
<212> TYPE: DNA
<213> ORGANISM: Artificial Sequence
<220> FEATURE:
<223> OTHER INFORMATION: primer P3

<400> SEQUENCE: 14
ccaccaccta ggcggcggat ttgtcc                                            26

<210> SEQ ID NO 15
<211> LENGTH: 639
<212> TYPE: DNA
<213> ORGANISM: Artificial Sequence
<220> FEATURE:
<223> OTHER INFORMATION: parR plasmid component

<400> SEQUENCE: 15
atggctaaaa accctatctc aaataaggca gataacgacc ggattcagat ccggtctttc        60
tggatatccg aaagaaaagc accctatgtt tatagtttct tgaaaaaaac agaactttct      120 catagggggtg accaactgga tttaattagg tcggctatta gtaccgggtt ggtattgaat     180
aatttatttc ctgacttggc aaattttata aatggtttaa acgaaagatt aacacttgca     240
gatcttaata ggtttctgaa tgatggaaat actatagata ctgaacctaa gcctcctatt     300
aatgtattgc tagagaatgt cttagatcaa aagtttaagg agtatttaac acctctacaa     360
ttagataatt caaagcaaga ttctgttttct gtaaaagaaa ccttccttgt acaaaaggaa    420
catgcctgct ttggtgtgaa gattgaaaat gagggaagcg atacctctat accatctgaa     480
agcccacttt cttcagatgc atccaaaatt tcaaaagaaa agtccatttc cgctgtggtg     540
ccagtgctag aaaaagtatc ggatgaaaat caaaccgcct ccataagcat aaaatctaaa    600
gctaaggcaa acaagcgact ggcaactttg gcaagatag                            639

<210> SEQ ID NO 16
<211> LENGTH: 294
<212> TYPE: DNA
<213> ORGANISM: Artificial Sequence
<220> FEATURE:
<223> OTHER INFORMATION: parC plasmid component

<400> SEQUENCE: 16
tcatgcgtgg ccccattgct gatgatcggg gtacgccagg tgcagcactg catcgaaatt       60
ggccttgcag tagccgtcca gcgccacccg cgagccgaac gccggcgaaa ggtactcgac      120
caggccgggc cggtcgcgga cctcgcgccc caggacgtgg atgcgccggc gcgtgtgcc      180 gtcgggtcca ggcacgaagg ccagcgcctc gatgttgaag tcgatggata gaagttgtcg     240
gtagtgcttg gccgccctca tcgcgtcccc cttggtcaaa ttgggtatac ccat           294
```

<210> SEQ ID NO 17
<211> LENGTH: 828
<212> TYPE: DNA
<213> ORGANISM: Artificial Sequence
<220> FEATURE:
<223> OTHER INFORMATION: alfA plasmid component

<400> SEQUENCE: 17

```
ttgacactaa ctactgtaat tgatatcggg aattttagta cgaagtacgc ttataaggac      60
aaaaaacaaa ttaaggtcgg cagtttccct tctattctcc atagctacaa gcctttagaa     120
gattacgagg gaatggaaag agtagagtac aacggccttg attattatgt tggagaaacc     180
gttaagaact tctatttcgg ccgtgaagaa caaatgtatt tcggcaatac aagaaaaggc     240
catatggaag gtcaaattcg attagtatat gctctctata caatctttaa agagactgga     300
aagaaagaat ttaacttaat tctaacttgc ccatatgaaa gtatggttac agataaaaaa     360
tatttcgttc aacattttga aggagaaaga gaagttatcg ttgaaggaaa gtcattcaaa     420
ttcactgtac ataatatcgt gatggctgca gagggattag gagccctaaa cttctcagat     480
tcattaaact gcgtcattgt agatgctggt tctaagacat aaacgtcct ttatttaatc      540
aatgggtcta taagtaaaat ggatagccat actattaatg gtgggacgat cgacaattca     600
ataatggatt tggcgaagac ttttgctaag acttgcagca atatcgatta tgactaccct     660
attgtttgta caggtggtaa agcagaagaa atgaaagaat gcttagagaa tgttggatat     720
tccactgtaa gttctgccga actgggtgag gataaaccat cttactatgt taattcagtt     780
ggattgcttc taaaatacgg taggaagttt gaggagatgt ttgcgtga                   828
```

<210> SEQ ID NO 18
<211> LENGTH: 963
<212> TYPE: DNA
<213> ORGANISM: Artificial Sequence
<220> FEATURE:
<223> OTHER INFORMATION: parM plasmid component

<400> SEQUENCE: 18

```
atgttggtat tcattgatga cggttcaaca aacatcaaac tacagtggca ggaaagcgac      60
ggaacaatta acagcacat tagcccgaac agcttcaaac gcgagtgggc agtctctttt     120
ggtgataaaa aggtctttaa ctacacactg aacggcgaac agtattcatt tgatccaatc     180
agcccggatg ctgtagtcac aaccaatatc gcatggcaat acagcgacgt taatgtcgtt     240
gcagtgcatc acgccttact gaccagtggt ctgccggtaa gcgaagtgga tattgtttgc     300
acacttcctc tgacagagta ttacgacaga ataaccaac ccaatacgga aaatattgag      360
cgtaagaaag caaacttccg gaaaaaaatt acattaaatg gcggggatac attcacaata     420
aaagatgtaa aagtcatgcc tgaatctata ccggcaggtt atgaagttct acaagaactg     480
gatgagttag attctttatt aattatagat ctcgggggca ccacattaga tatttctcag     540
gtaatgggga aattatcggg gatcagtaaa atatacggag actcatctct tggtgtctct     600
ctggttacat ctgcagtaaa agatgccctt tctcttgcga gaacaaaagg aagtagctat     660
cttgctgacg atataatcat tcacagaaaa gataataact atctgaagca acgaattaat     720
gatgagaaca aaatatcaat agtcaccgaa gcaatgaatg aagcacttcg taaacttgag     780
caacgtgtat taaatacgct caatgaattt tctggttata ctcatgttat ggttataggc     840
ggtggcgcag aattaatatg cgatgcagta aaaaaaacaca cacagattcg tgatgaacgt     900
```

```
tttttcaaaa ccaataactc tcaatatgat ttagttaacg gtatgtatct cataggtaat    960
taa                                                                  963
```